(12) United States Patent
Pavlov et al.

(10) Patent No.: US 10,278,742 B2
(45) Date of Patent: May 7, 2019

(54) INTERBODY INTERFERENCE IMPLANT AND INSTRUMENTATION

(71) Applicants: DePuy Synthes Products, Inc., Raynham, MA (US); Paul Pavlov, Nijmegen (NL)

(72) Inventors: Paul Pavlov, Nijmegen (NL); Tom Overes, Langendorf (CH); Peter Brunner, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 1387 days.

(21) Appl. No.: 14/075,332

(22) Filed: Nov. 8, 2013

(65) Prior Publication Data

US 2014/0135927 A1 May 15, 2014

Related U.S. Application Data

(60) Provisional application No. 61/725,179, filed on Nov. 12, 2012.

(51) Int. Cl.
  *A61B 17/70* (2006.01)
  *A61F 2/46* (2006.01)
  (Continued)

(52) U.S. Cl.
  CPC .......... *A61B 17/7055* (2013.01); *A61F 2/447* (2013.01); *A61F 2/4455* (2013.01); *A61F 2/4611* (2013.01); *A61F 2/30744* (2013.01); *A61F 2/4405* (2013.01); *A61F 2002/3008* (2013.01); *A61F 2002/3082* (2013.01); *A61F 2002/30266* (2013.01); *A61F 2002/30578* (2013.01); *A61F 2002/30594* (2013.01); (Continued)

(58) Field of Classification Search
  CPC ........ A61F 2002/30995; A61F 2/30988; A61F 2/44; A61F 2/447; A61F 2/46; A61F 2/4611
  See application file for complete search history.

(56) References Cited

U.S. PATENT DOCUMENTS

| 5,716,415 A | 2/1998 | Steffee |
| 6,099,531 A | 8/2000 | Bonutti |

(Continued)

FOREIGN PATENT DOCUMENTS

| CN | 1076850 | 10/1993 |
| CN | 1838916 | 9/2006 |

(Continued)

OTHER PUBLICATIONS

U.S. Appl. No. 61/725,179, filed Nov. 12, 2012, Pavlov et al.
"Surgical Technique Manual", DePuy Spine, Inc., Jan. 2012, 25 sheets.

*Primary Examiner* — Anu Ramana
(74) *Attorney, Agent, or Firm* — BakerHostetler

(57) ABSTRACT

An implant includes an implant body sized and shaped for insertion into a sacro-iliac joint, the implant including a first bone fixation element receiving channel extending through a portion thereof along a first central axis oriented so that, when the implant body is received within the sacro-iliac joint in a desired configuration, a bone fixation element inserted into the first bone fixation element receiving channel will extend into a first one of the bones forming the joint.

22 Claims, 58 Drawing Sheets

(51) Int. Cl.
*A61F 2/44* (2006.01)
*A61F 2/30* (2006.01)

(52) U.S. Cl.
CPC ............ *A61F 2002/30774* (2013.01); *A61F 2002/30785* (2013.01); *A61F 2002/30787* (2013.01); *A61F 2002/30836* (2013.01); *A61F 2002/30878* (2013.01); *A61F 2002/30879* (2013.01); *A61F 2002/30891* (2013.01); *A61F 2002/30904* (2013.01); *A61F 2002/30995* (2013.01); *A61F 2002/4623* (2013.01); *A61F 2002/4627* (2013.01); *A61F 2002/4677* (2013.01)

(56) References Cited

U.S. PATENT DOCUMENTS

| | | | |
|---|---|---|---|
| 6,197,028 | B1 | 3/2001 | Ray et al. |
| 6,547,795 | B2 | 4/2003 | Schneiderman |
| 6,635,086 | B2 | 10/2003 | Lin |
| 6,972,019 | B2 * | 12/2005 | Michelson ............ A61F 2/4455 606/247 |
| 7,101,398 | B2 | 9/2006 | Dooris et al. |
| 7,163,561 | B2 * | 1/2007 | Michelson ............ A61F 2/442 606/307 |
| 7,326,248 | B2 | 2/2008 | Michelson |
| 7,369,360 | B2 | 5/2008 | Vas et al. |
| 7,655,044 | B2 | 2/2010 | Kwak |
| 7,695,514 | B2 | 4/2010 | Kwak |
| 7,744,630 | B2 | 6/2010 | Lancial |
| 7,799,054 | B2 | 9/2010 | Kwak et al. |
| 7,819,903 | B2 * | 10/2010 | Fraser ............... A61B 17/7059 606/286 |
| 7,828,824 | B2 | 11/2010 | Kwak et al. |
| 8,043,334 | B2 | 10/2011 | Fisher et al. |
| 8,070,783 | B2 | 12/2011 | Kwak et al. |
| 8,133,261 | B2 | 3/2012 | Fisher et al. |
| 8,142,503 | B2 | 3/2012 | Malone |
| 8,197,513 | B2 | 6/2012 | Fisher et al. |
| 8,287,597 | B1 | 10/2012 | Pimenta et al. |
| 8,349,017 | B2 | 1/2013 | Marnay et al. |
| 8,496,691 | B2 | 7/2013 | Blain |
| 9,265,546 | B2 | 2/2016 | Blain |
| 9,381,045 | B2 * | 7/2016 | Donner ............... A61F 2/30988 |
| 9,486,327 | B2 | 11/2016 | Martynova et al. |
| 2002/0116008 | A1 | 8/2002 | Lin et al. |
| 2004/0102774 | A1 | 5/2004 | Trieu |
| 2004/0192613 | A1 | 9/2004 | Jennings |
| 2005/0055096 | A1 | 3/2005 | Serhan et al. |
| 2005/0159746 | A1 | 7/2005 | Grob et al. |
| 2005/0240188 | A1 | 10/2005 | Chow et al. |
| 2006/0004448 | A1 | 1/2006 | Casey |
| 2006/0036323 | A1 | 2/2006 | Carl et al. |
| 2006/0064099 | A1 | 3/2006 | Pavlov et al. |
| 2006/0085071 | A1 * | 4/2006 | Lechmann ............ A61B 17/86 623/17.11 |
| 2006/0089717 | A1 | 4/2006 | Krishna et al. |
| 2006/0287729 | A1 | 12/2006 | Segal et al. |
| 2007/0016195 | A1 | 1/2007 | Winslow et al. |
| 2007/0016196 | A1 | 1/2007 | Winslow et al. |
| 2007/0135814 | A1 | 6/2007 | Farris |
| 2008/0140085 | A1 | 6/2008 | Gately et al. |
| 2008/0161810 | A1 | 7/2008 | Melkent |
| 2008/0172061 | A1 | 7/2008 | Ragbir |
| 2008/0177306 | A1 * | 7/2008 | Lamborne ........... A61B 17/7062 606/246 |
| 2008/0249569 | A1 | 10/2008 | Waugh et al. |
| 2008/0255622 | A1 | 10/2008 | Mickiewicz et al. |
| 2008/0262623 | A1 | 10/2008 | Bagga et al. |
| 2009/0024166 | A1 | 1/2009 | Carl et al. |
| 2009/0062921 | A1 | 3/2009 | Michelson |
| 2009/0192613 | A1 * | 7/2009 | Wing ................... A61F 2/4465 623/17.11 |
| 2009/0306671 | A1 | 12/2009 | McCormack et al. |
| 2010/0076493 | A1 | 3/2010 | Fauth et al. |
| 2010/0087925 | A1 | 4/2010 | Kostuik et al. |
| 2010/0145397 | A1 | 6/2010 | Overes et al. |
| 2011/0004247 | A1 | 1/2011 | Lechmann et al. |
| 2011/0098710 | A1 | 4/2011 | Spratt et al. |
| 2011/0172769 | A1 | 7/2011 | Ganem et al. |
| 2011/0264229 | A1 | 10/2011 | Jeffrey |
| 2012/0010662 | A1 | 1/2012 | O'Neil et al. |
| 2012/0083883 | A1 | 4/2012 | Ginn |
| 2012/0095560 | A1 | 4/2012 | Donner |
| 2012/0185049 | A1 | 7/2012 | Varela |
| 2013/0123793 | A1 | 5/2013 | Kehres et al. |
| 2013/0123923 | A1 | 5/2013 | Pavlov et al. |

FOREIGN PATENT DOCUMENTS

| | | |
|---|---|---|
| CN | 101296670 A | 10/2008 |
| CN | 201244104 | 5/2009 |
| CN | 102458278 | 5/2012 |
| DE | 10135771 A1 | 2/2003 |
| JP | 2002-508679 | 3/2002 |
| JP | 2004-209248 A | 7/2004 |
| JP | 2007-518524 | 7/2007 |
| JP | 2008-522787 | 7/2008 |
| JP | 2009-519113 | 5/2009 |
| JP | 2010-115477 A | 5/2010 |
| JP | 2010-523216 | 7/2010 |
| WO | 93/14721 A1 | 8/1993 |
| WO | 00/23015 A1 | 4/2000 |
| WO | 00/53126 A1 | 9/2000 |
| WO | WO 02/078514 | 10/2002 |
| WO | 2006/065774 A1 | 6/2006 |
| WO | 2006/101837 A2 | 9/2006 |
| WO | WO 2007/098288 | 8/2007 |
| WO | WO 2010/121028 | 10/2010 |
| WO | WO 2011/008864 A1 | 1/2011 |
| WO | WO 2014/074853 | 5/2014 |

\* cited by examiner

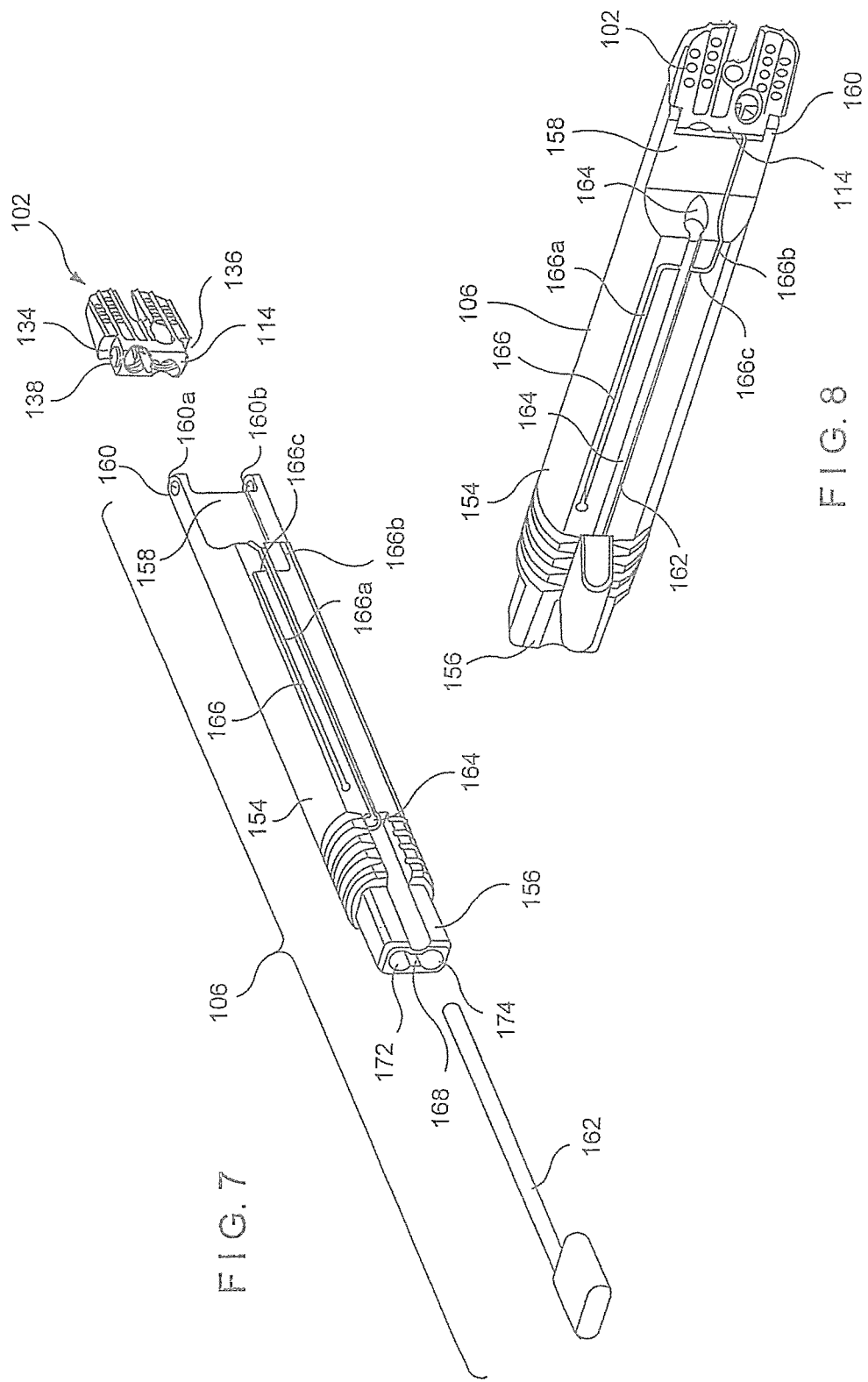

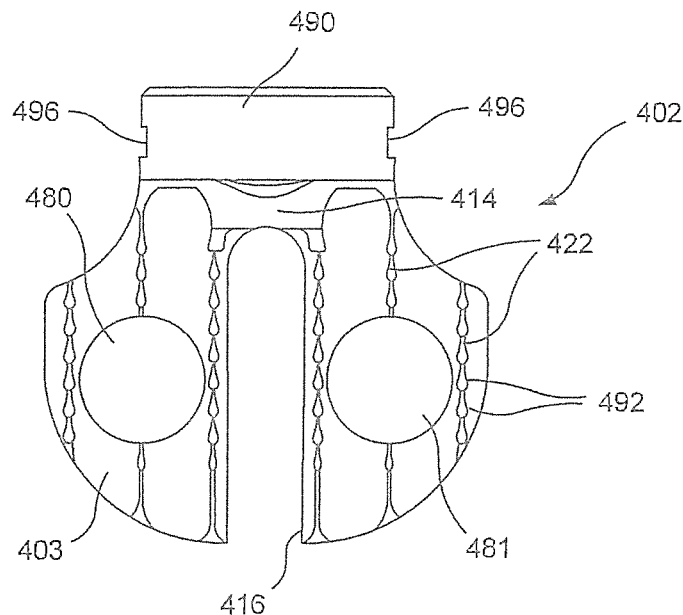
FIG. 23
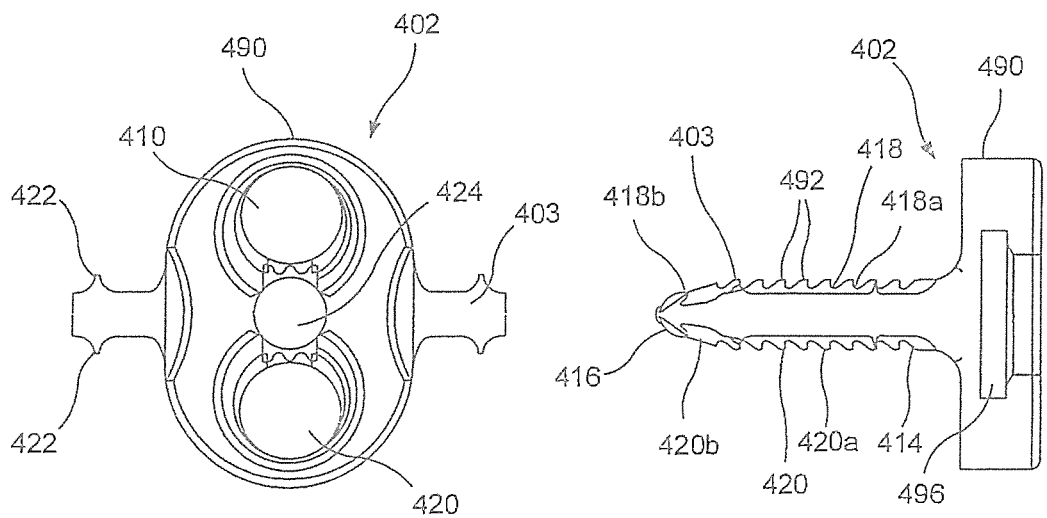
FIG. 24
FIG. 25

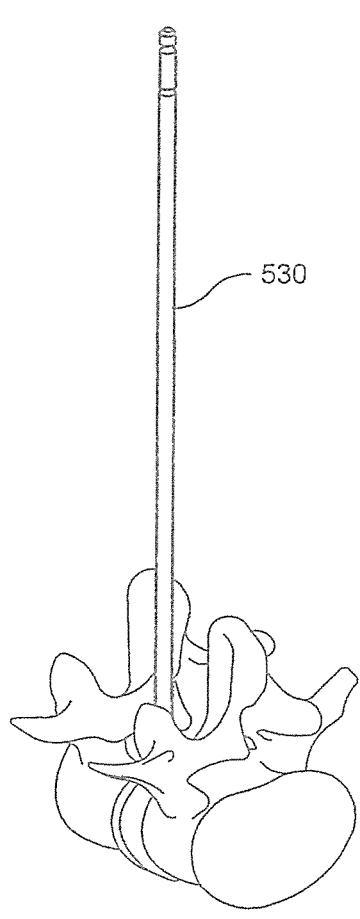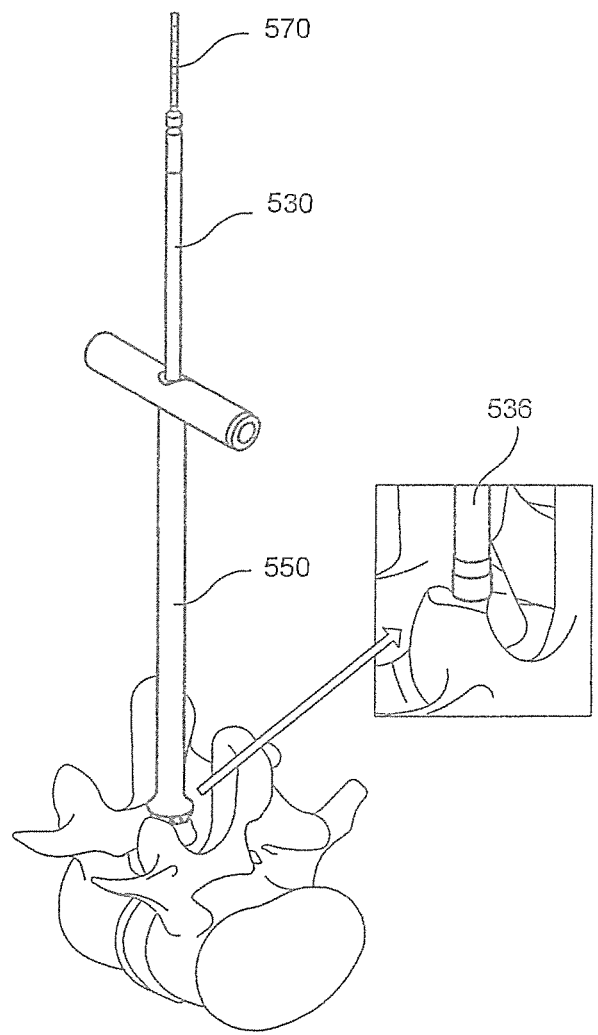
F I G. 39      F I G. 40

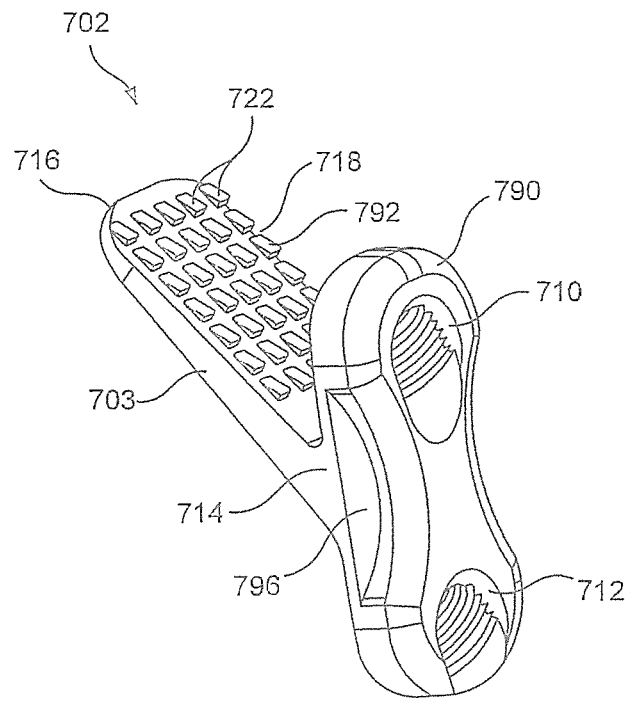
FIG. 45
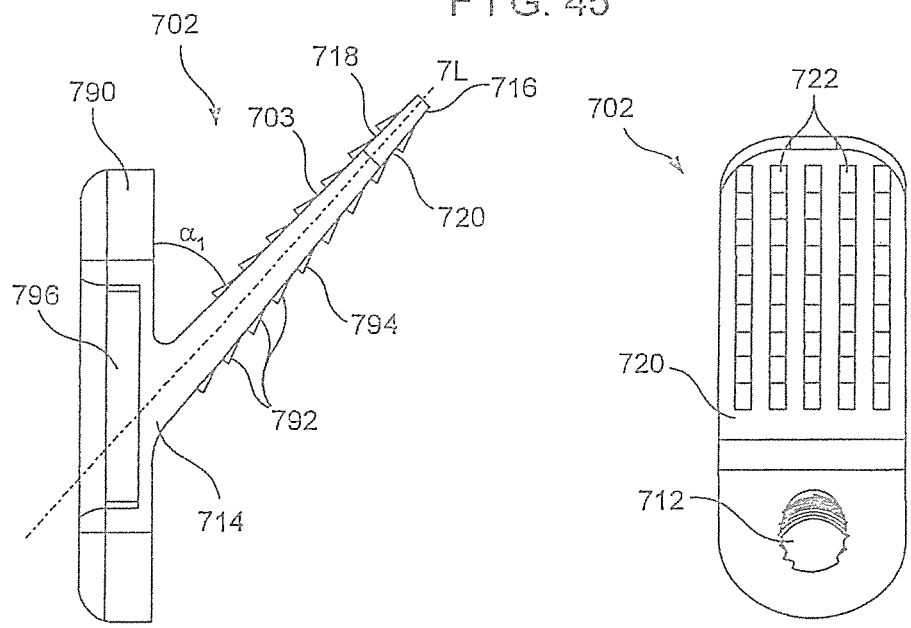
FIG. 46
FIG. 47

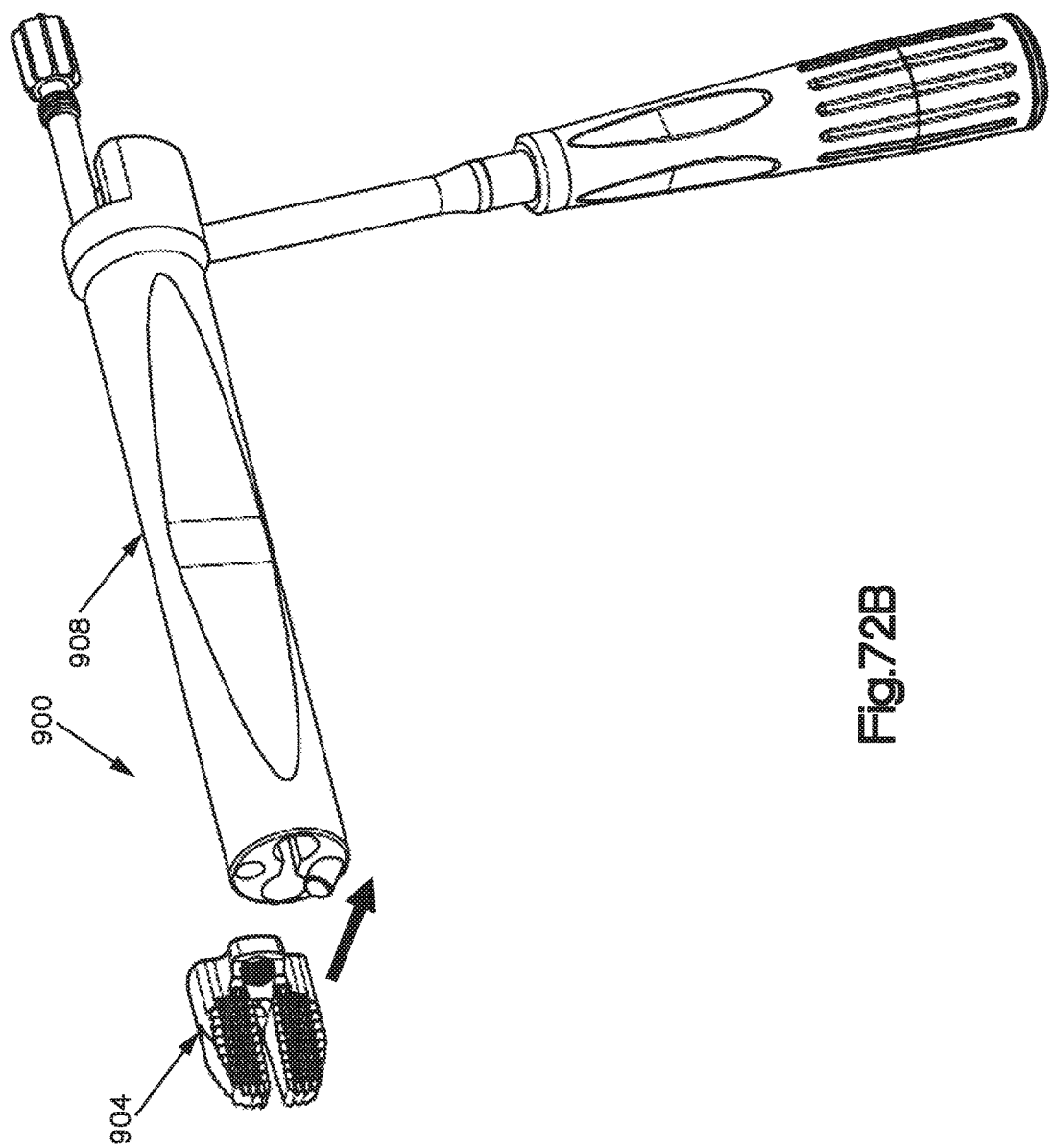

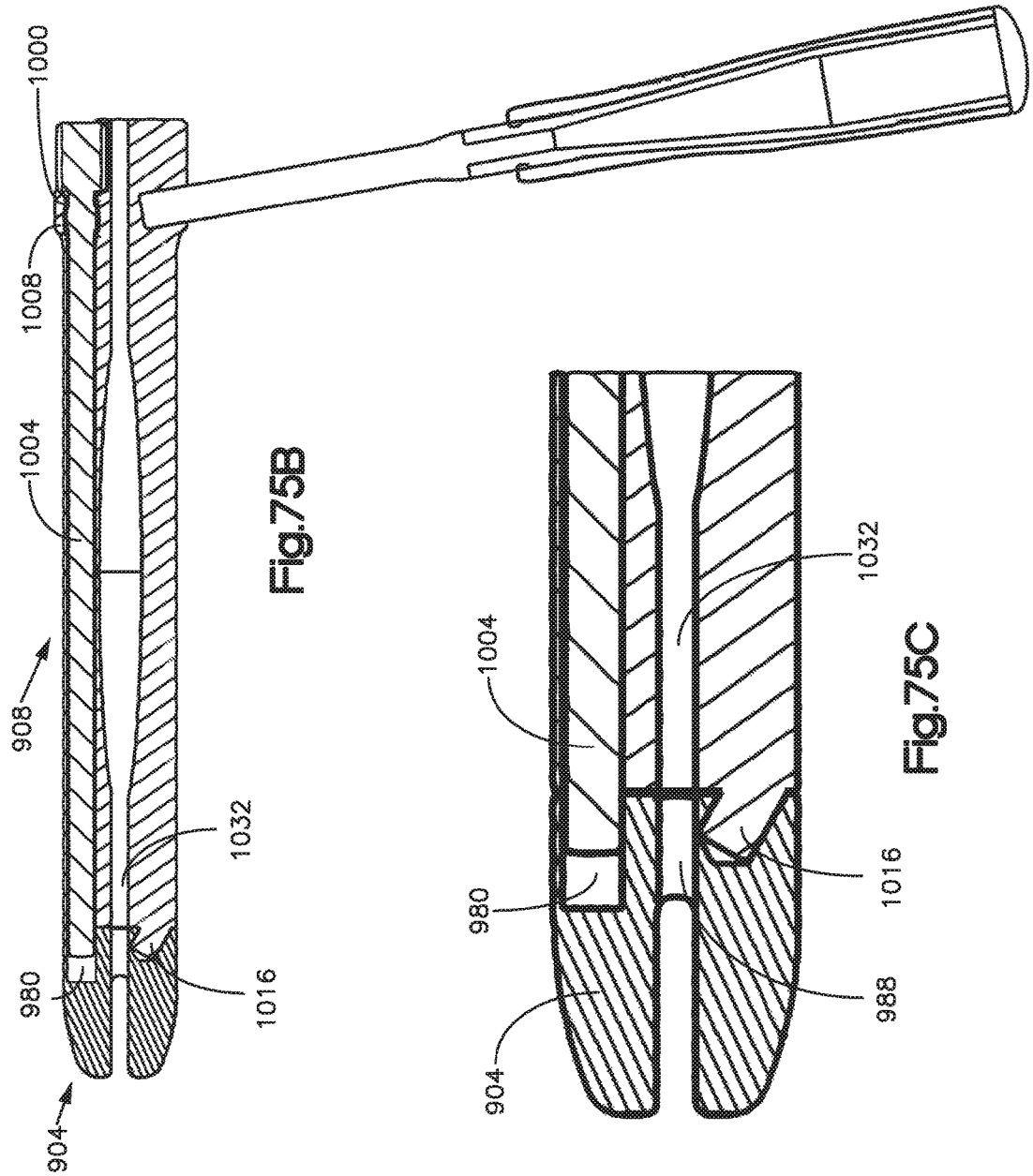

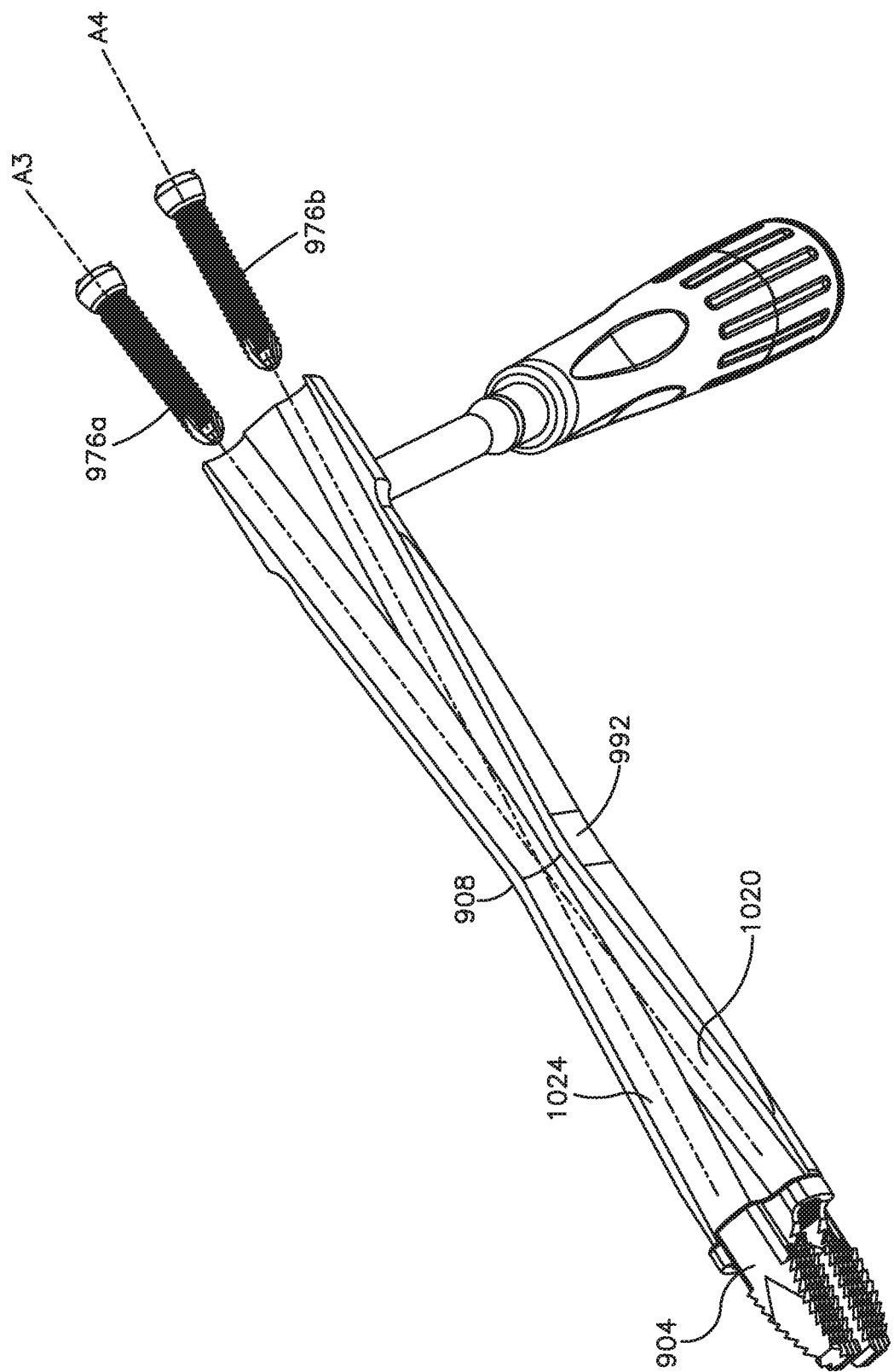

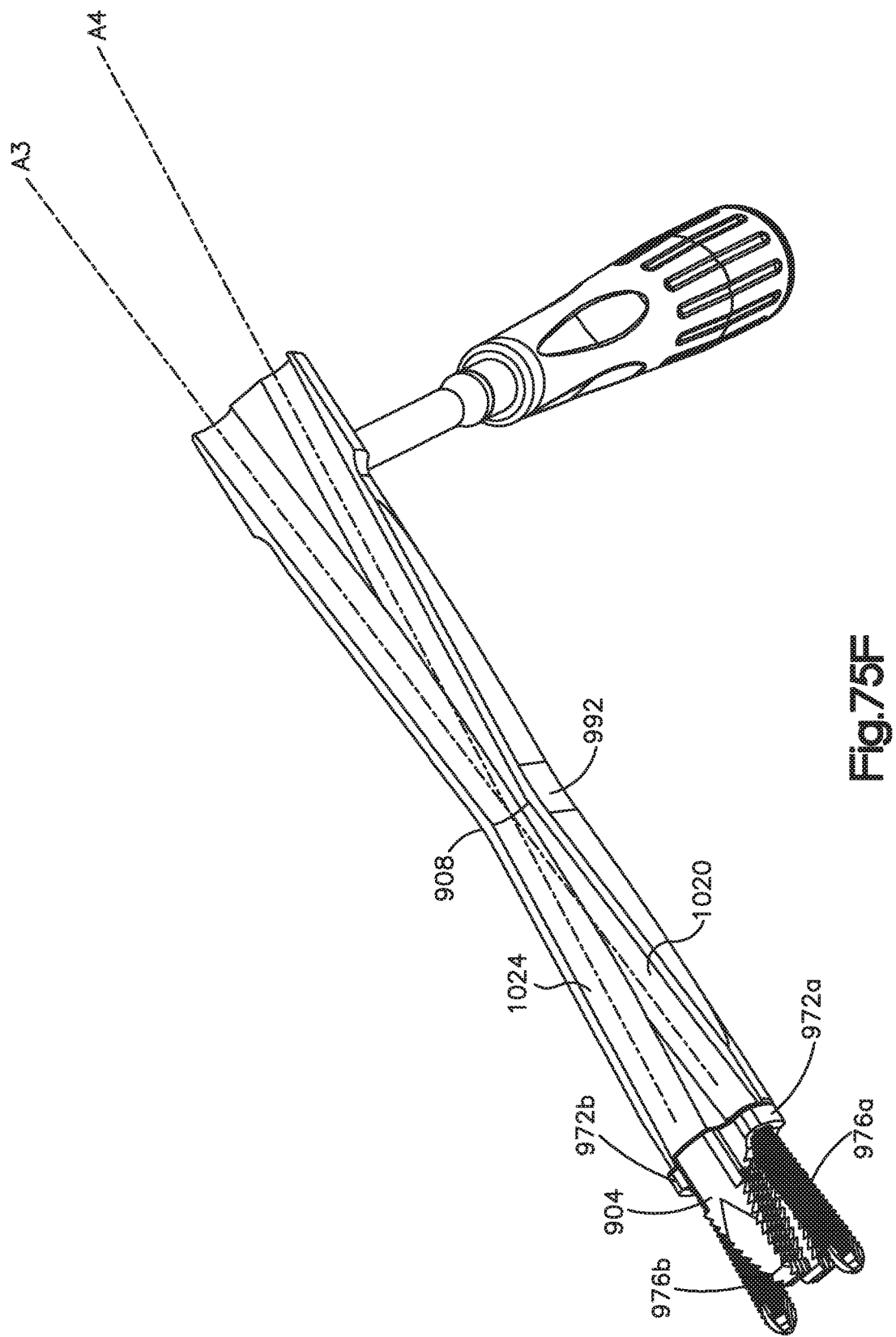

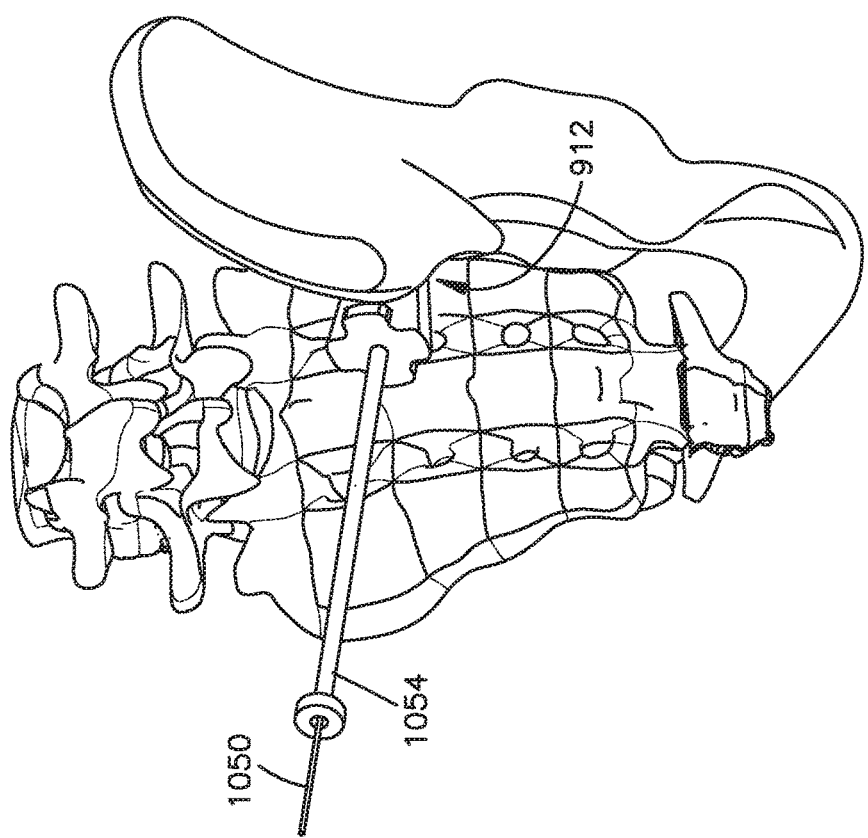
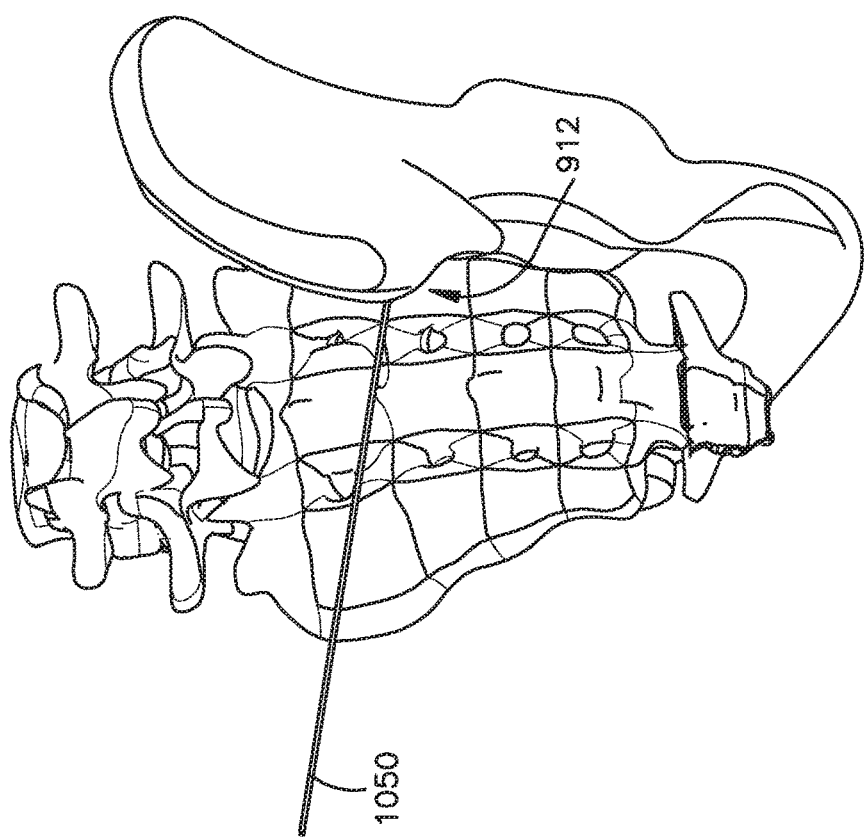

INTERBODY INTERFERENCE IMPLANT AND INSTRUMENTATION

CROSS REFERENCE TO RELATED APPLICATIONS

This application claims priority to U.S. Provisional Application Ser. No. 61/725,179, filed Nov. 12, 2012, the contents of which are hereby incorporated by reference as if set forth in their entirety herein.

BACKGROUND

Posterior spinal fusion may be achieved using, for example, screws, rods and/or plates to fix two or more adjacent vertebrae relative to one another and facilitate fusion. Pedicle screws are used to add extra support to prevent the vertebrae from moving while fusing. Further, fusion of the sacral bone and iliac bone may be desired. Known implants and/or fixation devices may be bulky, causing patient-discomfort and requiring time-consuming, invasive procedures.

SUMMARY

In one embodiment, an implant can be configured to be inserted into a sacro-iliac joint along an insertion direction. The implant can include an implant body having a proximal end and a distal end spaced from the proximal end along the insertion direction. The implant body can define an iliac engagement surface sized and configured to abut the iliac bone when the implant is inserted into the sacro-iliac joint, and a sacral engagement surface sized and configured to abut the sacral bone when the implant is inserted into the sacro-iliac joint. At least one of the iliac engagement surface and the sacral engagement surface converges toward the other of the iliac engagement surface and the sacral engagement surface as it extend along a direction from the proximal end to the distal end. The implant can further include a head portion that extends from the proximal end of the implant body. The head portion can include a head body and a first bone fixation element receiving aperture that extends through the head body along a first central axis such that when the implant body is received within the sacro-iliac joint, the first bone fixation element receiving aperture is configured to receive a bone fixation element along the first central axis so as to align the bone fixation element with one of the sacral bone or the iliac bone.

In another embodiment an implant can be configured to be inserted into a bone joint along an insertion direction. The implant can include an implant body having a proximal end and a distal end spaced from the proximal end along the insertion direction. The implant body can define a first bone engagement surface sized and configured to abut the first bone when the implant is inserted into the bone joint, and a second bone engagement surface sized and configured to abut the second bone when the implant is inserted into the bone joint. The implant can further include a head portion that extends from the proximal end of the implant body. The head portion can include a head body and at least one bone fixation element receiving aperture that extends through the head body along a central axis such that when the implant body is received within the bone joint, the receiving aperture is configured to receive a bone fixation element along the central axis so as to align the bone fixation element with one of the first bone or the second bone. The head portion can further include a first locking channel that extends into the head body along a first locking central axis, and a second locking channel that extends into the head body along a second locking central axis that is angularly offset with respect to the first locking central axis.

In another embodiment, an implant can be configured to be inserted along an insertion direction into a sacro-iliac joint defined between a sacral bone and an iliac bone. The implant can include an implant body having a proximal end and a distal end spaced from the proximal end along the insertion direction. The implant body can define an iliac engagement surface sized and configured to abut the iliac bone when the implant is inserted into the sacro-iliac joint, and a sacral engagement surface sized and configured to abut the sacral bone when the implant is inserted into the sacro-iliac joint. The implant can further include a head portion that extends from the proximal end of the implant body along a proximal direction. The head portion can include a head body and at least a first leg and a second leg that extend from the head body along the proximal direction. The first leg can be spaced from the second leg along a direction that is substantially perpendicular to the insertion direction such that a rod receiving channel is defined between the first and second legs.

Also disclosed is an embodiment of an insertion instrument can be configured to insert an implant into a joint defined between first and second bone parts, the implant defining first and second locking channels. The insertion instrument can include a guide body that defines a proximal end and a distal end that is spaced from the proximal end along a first direction. The guide body can have a channel that extends through at least a portion of the guide body along a central channel axis and extends out the distal end. The instrument can further include a first locking member movable within the channel of the guide body between an unlocked position and a locked position such that the first locking member extends further from the distal end when in the locked position than when in the unlocked position. The instrument further includes a second locking member that extends from the distal end of the guide body along a second member central axis that is angularly offset with respect to the central channel axis. The second locking member can be configured to be received by the second locking channel of the implant. When the second locking member is inserted into the second locking channel of the implant, the channel of the guide body is configured to be positioned coaxial with respect to the first locking channel of the implant such that movement of the first locking member from the unlocked position to the locked position causes the first locking member to be inserted into the first locking channel of the implant to thereby couple the implant to the insertion instrument.

In an embodiment the implant and the insertion instrument can be included in a system. In another embodiment, the system can include first and second implants that are configured to be inserted into respective sacro-iliac joints. The system can further include a rod configured as a bridge and having a first side and a second side. The first side can be configured to be received by the rod receiving channel of the first implant and the second side can be configured to be received by the rod receiving channel of the second implant.

Also disclosed is a method of coupling an interbody implant to an instrument. The method can include the steps of positioning an interbody implant proximate to a distal end of a guide body of an instrument having a first locking member movable within a channel of the guide body and a second locking member that extends from the distal end of the guide body along a central axis that is oblique to the central axis of the channel, the implant being positioned such that the second locking member of the instrument is aligned with a second locking channel of the interbody implant; inserting the second locking member of the instrument into the second locking channel of the implant such that the channel of the guide is aligned with a first locking channel of the interbody implant; and moving the first locking member within the channel so that a distal end of the first locking member engages the first locking channel of the interbody implant to thereby couple the interbody implant to the instrument.

Also disclosed is a method of inserting an implant into an interbody space. The method can include the steps of coupling an implant to an insertion instrument such that a first bone fixation receiving channel of the implant is coaxial with a first bone fixation receiving channel of the insertion instrument; inserting a guide wire into a sacro-iliac joint; guiding the insertion instrument and implant along the guide wire until at least a portion of the implant is inserted into the sacro-iliac joint; passing a first bone fixation element through the first bone fixation receiving channel of the insertion instrument and into the first bone fixation receiving channel of the implant so that the first bone fixation element engages a first bone that at least partially defines the sacro-iliac joint to thereby fix the implant to the first bone; and decoupling the insertion instrument from the implant.

The coupling step can include coupling the implant to the insertion instrument such that a second bone fixation receiving channel of the implant is coaxial with a second bone fixation receiving channel of the insertion instrument, and the method can further include passing a second bone fixation element through the second bone fixation receiving channel of the insertion instrument and into the second bone fixation receiving channel of the implant so that the second bone fixation element engages a second bone that at least partially defines the sacro-iliac joint to thereby fix the implant to the second bone.

The coupling step can include coupling the implant to the insertion instrument such that a third bone fixation receiving channel of the implant is coaxial with a third bone fixation receiving channel of the insertion instrument, and the method can further include passing a third bone fixation element through the third bone fixation receiving channel of the insertion instrument and into the third bone fixation receiving channel of the implant so that the third bone fixation element engages the first bone.

The coupling step can include coupling the implant to the insertion instrument such that a fourth bone fixation receiving channel of the implant is coaxial with a fourth bone fixation receiving channel of the insertion instrument, and the method step can further include passing a fourth bone fixation element through the fourth bone fixation receiving channel of the insertion instrument and into the fourth bone fixation receiving channel of the implant so that the fourth bone fixation element engages the second bone.

BRIEF DESCRIPTION OF THE DRAWINGS

FIG. 7 shows a perspective view of an aiming guide and implant of the system of FIG. 1;

FIG. 8 shows another perspective view of the aiming guide and implant of FIG. 7;

FIG. 23 shows another side view of the implant of FIG. 21;

FIG. 24 shows a top plan view of the implant of FIG. 21;

FIG. 25 shows yet another side view of the implant of FIG. 21;

FIG. 39 shows a perspective view of a guide wire inserted into a joint via a joint fording tool according to an alternate embodiment of the method of FIG. 36;

FIG. 40 shows a perspective view of a reamer slid over the joint finding tool of FIG. 39;

FIG. 45 shows a first perspective view of an implant according to yet another exemplary embodiment of the invention;

FIG. 46 shows a second perspective view of the implant of FIG. 45;

FIG. 47 shows a third perspective view of the implant of FIG. 45;

FIG. 72B is an exploded view of the implant system shown in FIG. 72A;

FIG. 75B is a side cross-sectional view of the insertion instrument and interbody implant of FIG. 75A coupled together;

FIG. 75C is a side detailed cross-sectional view of the interbody implant coupled to the insertion instrument;

FIG. 75D is a perspective cross sectional view of the insertion instrument coupled to the interbody implant such that first and second bone fixation receiving apertures of the insertion instrument are aligned with first and second bone fixation receiving apertures of the interbody implant;

FIG. 75F is a perspective view of the insertion instrument shown in FIG. 75D with a second bone fixation element inserted into the first bone fixation element receiving aperture of the interbody implant;

FIG. 76A is a perspective view of a guide wire inserted into a sacro-iliac joint defined between a sacral bone and an iliac bone;

FIG. 76B is a perspective view of a rasp being guided along the guide wire to prepare the joint to match the interbody implant geometry;

DETAILED DESCRIPTION

Figure 1:
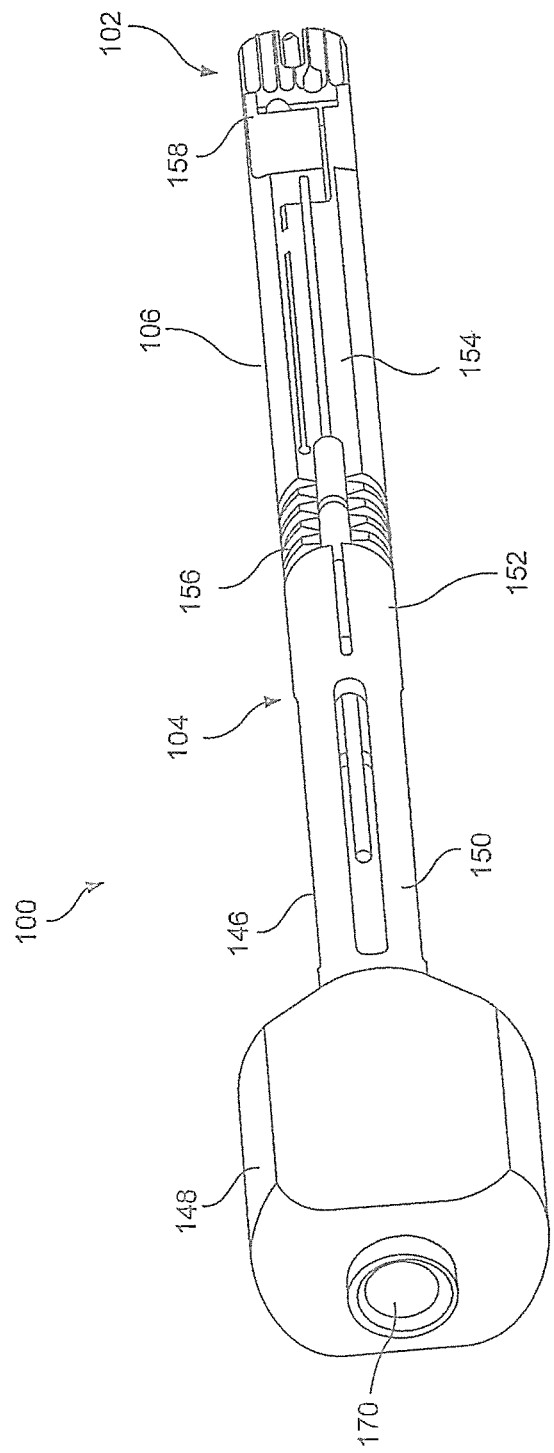
FIG. 1 shows a perspective view of a system according to an exemplary embodiment of the present invention.

The present invention may be further understood with reference to the following description and the appended drawings, wherein like elements are referred to with the same reference numerals. The present invention relates to bone treatment devices and, in particular, relates to a minimally invasive posterior fusion device. Exemplary embodiments of the present invention describe a system and method for posterior spinal fusion, including an implant shaped for insertion into a facet joint of adjacent vertebra along with an insertion tool to facilitate proper insertion and fixation thereof. It will be understood by those of skill in the art that the system and method of the present invention utilize a faster, less invasive technique which requires less muscle stripping and does not require the usage of pedicle screws for stabilization. It should be noted that the terms "proximal" and "distal" as used herein, are intended to refer to a direction toward (proximal) and away from (distal) a surgeon or other user of the device.

Figure 2:
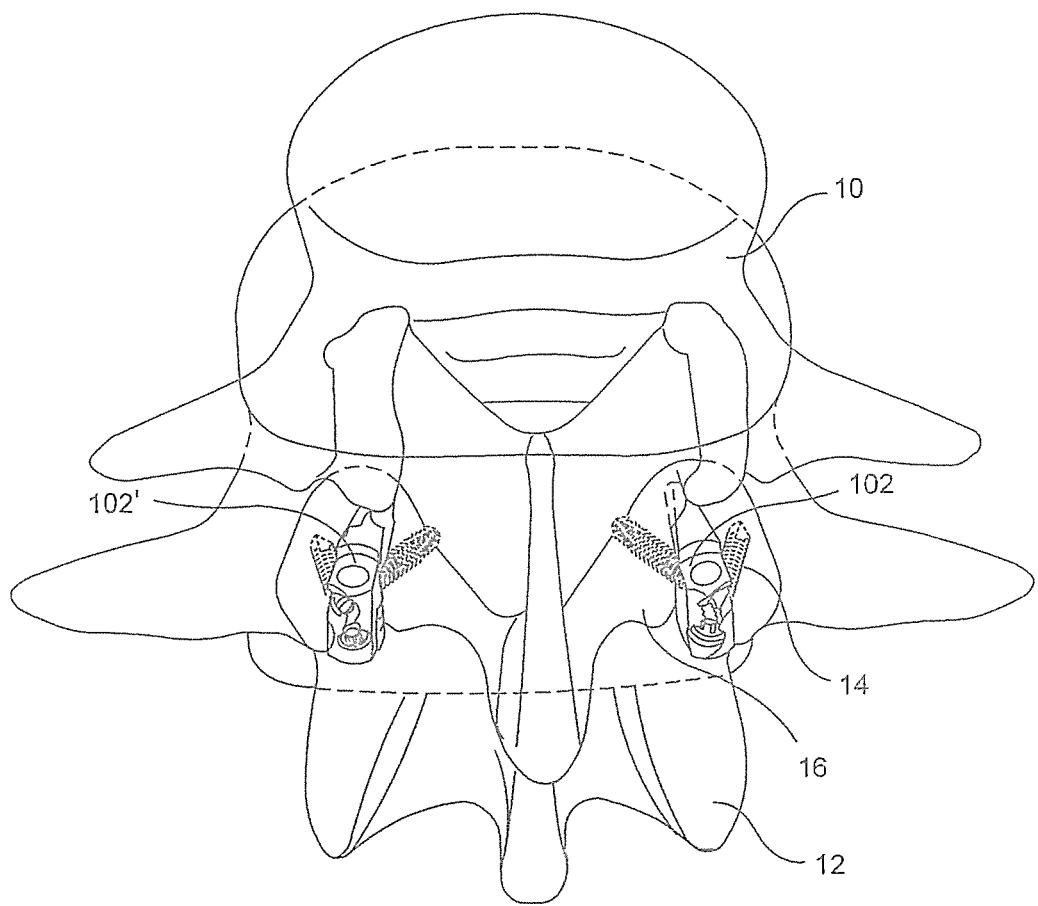
FIG. 2 shows a perspective view of an implant of the system of FIG. 1, implanted in a facet joint.
Figure 4:
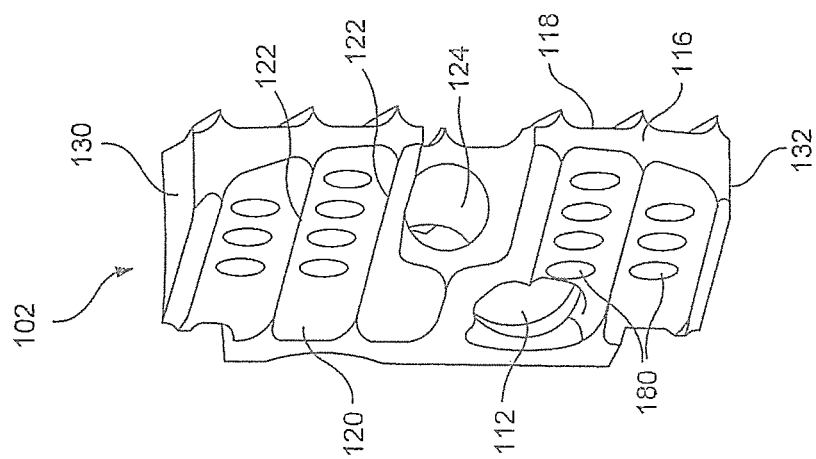
FIG. 4 shows another perspective view of the implant of FIG. 2.
Figure 3:
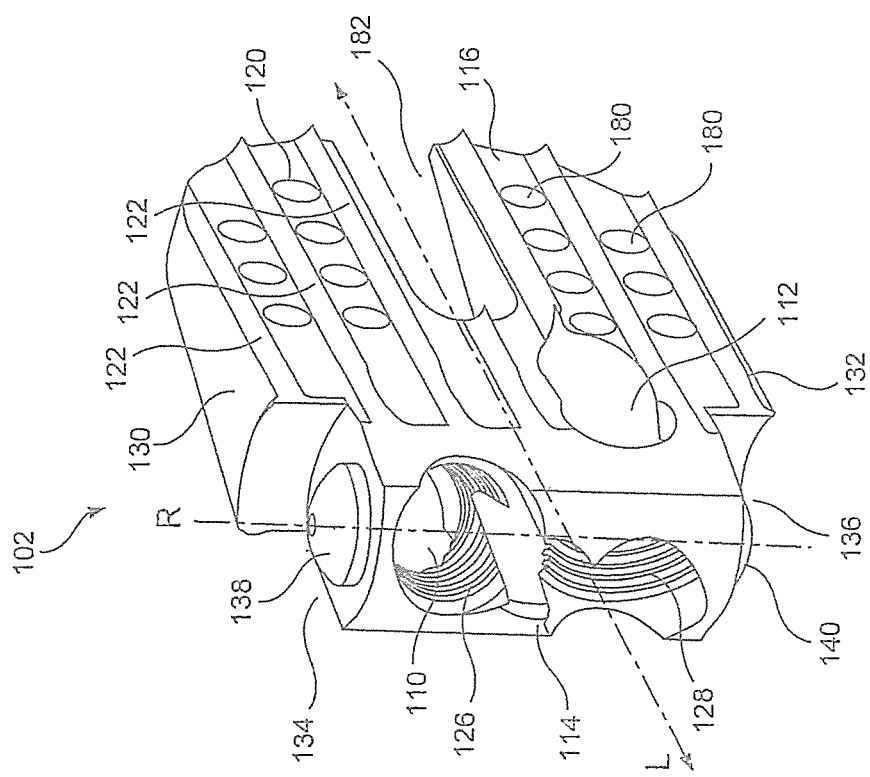
FIG. 3 shows a perspective view of the implant of FIG. 2.
Figure 5:
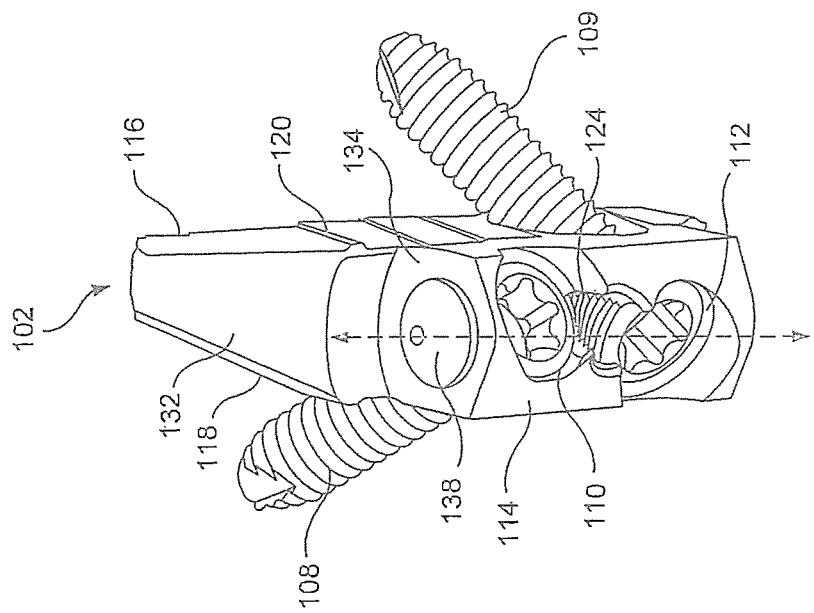
FIG. 5 shows a perspective view of the implant of FIG. 2 with bone fixation elements inserted through openings thereof.
Figure 6:
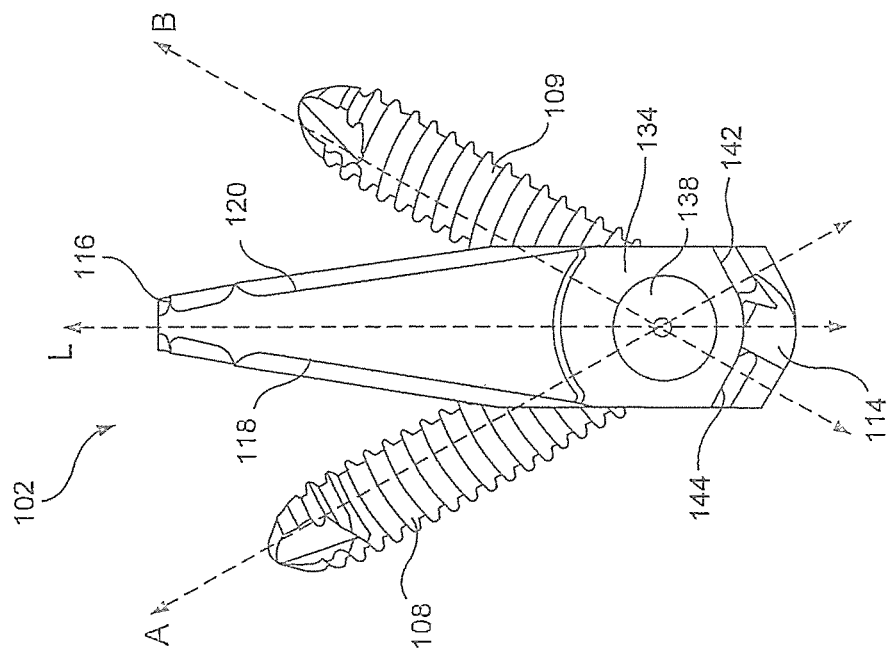
FIG. 6 shows a top plan view of the implant of FIG. 2 with bone fixation elements inserted through openings thereof.

As shown in FIGS. 1-9, a system 100 for posterior fusion comprises an implant 102 sized and shaped for insertion into a facet joint to facilitate fusion of first and second vertebrae 10, 12. As shown in FIGS. 1-2, the system 100 further comprises an insertion tool 104 including an impactor 146 for facilitating impaction of the implant 102 into the facet joint (i.e., the joint between a superior articular process 14 of the second vertebra 12 and an inferior articular process 16 of the first vertebra 10 directly above it) and an aiming guide 106 for guiding first and second bone fixation elements 108, 109 through first and second holes 110, 112, respectively, of the implant 102 to fix the implant 102 to the vertebrae 10, 12. It will be understood by those of skill in the art that each spinal motion segment (e.g., vertebra 10, 12) includes two facet joints (i.e., a right side and a left side) such that the system 100 may include a second implant 102. The implant 102, as described below, may be configured to be implanted into one of the two facet joints (e.g., the right facet joint) while the second implant 102' may be configured to be implanted into the other of the two facet joints (e.g., the left facet joint). Thus, although the second implant 102' is not described in detail, it will be understood by those of skill in the art that the second implant 102' may be substantially similar to the implant 102 and, in particular, may be a mirror image of the implant 102. Where the system 100 includes two implants 102, 102', the first and second implants 102, 102' may be color-coded and/or labeled to indicate whether the implants 102, 102' are configured for the right or left facet joint.

As shown in FIGS. 3-6, the implant 102 is substantially wedge-shaped extending along a longitudinal axis L and tapering from a first end 114 which, when implanted into the facet joint in a desired configuration, faces a posterior side of the spine, to a second end 116 which, when implanted into the facet joint faces a ventral side of the spine. The tapered second end 116 facilitates insertion of the implant 102 into the facet joint. The implant 102 is defined by first and second substantially planar surfaces 118, 120 which extend from the first end 114 to the second end 116 at an angle with respect to the longitudinal axis L to form the tapered wedge-shape, and third and fourth lateral surfaces 130, 132 which connect the first and second surfaces 118, 120. When implanted into the facet joint, the first surface 118 engages the inferior articular process 16 of the first vertebra 10 while the second surface 120 engages the superior articular process 14 of the second vertebra 12. The first and second surfaces 118, 120 each include a plurality of ribs 122 projecting therefrom and extending from the first end 114 to the second end 116 to guide the implant 102 into the joint and facilitate engagement with the first and second vertebra 10, 12. However, those skilled in the art will understand that the extent of some or all of the ribs 122 may be changed as desired. Furthermore, the first and second surfaces 118, 120 may be roughened and/or treated with a coating to facilitate bone ingrowth. The implant 102 also includes a plurality of openings 180 extending therethrough from the first surface 118 to the second surface 120 to promote bony growth therethrough, increasing stability after fusion. In a further embodiment, the implant 102 may also include a cut out 182 extending proximally from the second end 116 (i.e., toward the first end 114) and extending therethrough from the first surface 118 to the second surface 120. The cut out 182 minimizes sharp edges that may be present to accommodate a central opening 124 through which a K-wire or similar device may be positioned.

The implant 102 also includes a central opening 124 extending therethrough from the first end 114 to the second end 116 along the longitudinal axis L. The central opening 124 is sized and shaped to accommodate a guide wire therethrough such that the implant 102 may be slid along a guide wire inserted into the facet joint. The first and second holes 110, 112 of this embodiment extend through the implant 102 on opposing sides of the central opening 124. The first hole 110 extends therethrough from the first end 114 to the first surface 118 such that a first hole axis of the first hole 110 is angled with respect to the longitudinal axis L. As would be understood by those skilled in the art, the first hole 110 may include a threading 126 along all or a portion of an inner surface thereof for engaging a threading on a head of a first bone fixation element 108 inserted therethrough. The first bone fixation element 108 may be received in the first hole 110 along the first hole axis A such that a shaft thereof is inserted into the inferior articular process of the first vertebra 10. The second hole 112 extends therethrough from the first end 114 to the second surface 120 along a second hole axis B of the second hole 112 angled with respect to the longitudinal axis L in a direction opposite the first hole axis A. For example, the first axis A may be angled with respect to the longitudinal axis L at an angle between approximately 10° and 450 and, more particularly, between 250 and 30° while the second axis B may be angled with respect to the longitudinal axis L at an angle between approximately 100 and −45° and, more particularly, between −25° and 300. Similar to the first hole 110, the second hole 112 may include threading 128 along all or a portion of an inner surface thereof for engaging a threading on a head of a second bone fixation element 109 inserted therethrough.

The second bone fixation element 109 may be received within the second hole 112 along the second hole axis B such that a shaft thereof is inserted into the inferior articular process of the second vertebra 12. In one exemplary embodiment, a portion of the first and second holes 110, 112 at the first end 114 may be open to and overlap with the central opening 124, as shown. In this embodiment, a guide wire inserted through the central opening 124 prevents bone fixation elements 108, 109 from being inserted through the first and second openings 110, 112. In another embodiment, one or both of the first and second holes 110, 112 maybe formed as a distinct hole, separated from the central opening 124.

The first end 114 is configured for attachment to the aiming guide 106. For example, third and fourth surfaces 130, 132 of this embodiment include recesses 134, 136, respectively, at the first end 114 which permit a portion of the aiming guide 106 to be received therein. The recesses 134, 136 may also include protrusions 138, 140, respectively, which extend therefrom to engage a portion of the aiming guide 106 received therein. The protrusions 138, 140 may, for example, be dome shaped to facilitate engagement with the aiming guide 106 while also permitting the aiming guide 106 to pivot with respect to the implant 102 about an axis of rotation R. Thus, the protrusions 138, 140 may be coaxial with the axis of rotation R. The axis R may be substantially perpendicular to the third and fourth lateral surfaces 130, 132. Although the protrusions 138, 140 are described as dome-shaped, it will be understood by those of skill in the art that the protrusions 138, 140 maybe any of a variety of shapes so long as the protrusions 138, 140 permit engagement with the aiming guide 106 and pivoting of the implant 102 relative thereto. The first end 114 according to this embodiment of the invention also includes first and second abutting surfaces 142, 144, respectively, extending substantially parallel to the rotation axis R and at an angle with respect to the longitudinal axis L to define a maximum angle of pivot of the implant 102 relative to the aiming guide 106. The angles of the first and second abutting surfaces 142, 144 correspond to the angle of the first and second axes A, B of the first and second openings 110, 112, respectively.

As shown in FIG. 1, the impactor 146 and the aiming guide 106 of the insertion tool 104 are releasably coupled to one another via, for example, a friction fit. The impactor 146 includes a head 148 and a shaft 150 extending distally therefrom to a distal end 152 configured to be attached to the aiming guide 106. The distal end 152 may, for example, receive a portion of the aiming guide 106 therein. The impactor 146 also includes a channel 170 extending therethrough along a longitudinal axis for receiving a guide wire therethrough. The head 148 may have a larger cross-sectional area than the shaft 150, providing a surface on which a force may be exerted to impact the implant 102 into the facet joint.

As shown in FIGS. 7-8, the aiming guide 106 includes a body 154 extending along a longitudinal axis L' from a proximal end 156 configured to be attached to the distal end 152 of the impactor 146 to a distal end 158 configured to be coupled to the implant 102. The body 154 further includes a central channel 168 extending longitudinally therethrough from the proximal end 156 to the distal end 158 such that when the aiming guide 106 and/or impactor 146 is coupled to the implant 102, the central opening 124 of the implant 102 is aligned with the central channel 168 of the aiming guide 106 and the channel 170 of the impactor 146 to receive a guide wire therethrough. The body 154 also includes a first guide channel 172 and a second guide channel 174, each of which extend longitudinally therethrough from the proximal end 156 to the distal end 158 in a position corresponding to the first and second openings 110, 112, respectively, of the implant 102 such that when coupled thereto, drills and/or bone fixation elements 108, 109 may be guided therethrough into the first and second openings 110, 112. The first and second guide channels 172, 174 may overlap with the central channel 168 depending on a configuration of the first and second openings 110, 112 of the implant 102.

The proximal end 156 may, for example, have a reduced cross-section area sized and shaped to be received within the distal end 152 of the impactor 146 via a friction fit. The aiming guide 106 and the impactor 146 are coupled such that the longitudinal axes thereof are substantially coaxial with one another. The distal end 158 of the aiming guide 106 may include jaws 160 including first and second jaw members 160a, 160b extending distally therefrom on opposing sides of the longitudinal axis L'. The jaws 160 receive a portion of the first end 114 between the first and second jaw members 160a, 160b seated within the recesses 134, 136 of the implant 102. The jaw members 160a, 160b also include recesses along inner surfaces thereof sized and shaped to receive the protrusions 138, 140 therein to engage the implant 102. The body 154 may be at least partially formed of a compliant material and include a slot 166 extending along a portion thereof from an exterior surface to an interior surface of the body 154 to permit the jaw members 160a, 160b to be flexed apart from one another such that the first end 114 of the implant 102 may be received therebetween and the arms 160 extended over the protrusions 138, 140 to be "snapped" thereover. Upon coupling the aiming guide 106 to the implant 102, the arms 106 may revert to an initial, undeformed configuration to hold the first end 114 therebetween. The slot 166 may, for example, be substantially Z-shaped including first and second portion 166a, 166b extending substantially parallel to the longitudinal axis L' and a third portion 166c connecting the first and second portions 166a, 166b to form a continuous slot 166.

The aiming guide 106 according to this embodiment further includes a locking rod 162 which may be inserted into a locking channel 164 extending along an exterior of the body 154 to lock the arms 160 in the undeformed configuration, preventing the implant 102 from being inadvertently disengaged therefrom. The locking channel 164 extends along the body 154 and intersects with the slot 166 such that the when the locking rod 162 is inserted therethrough, the jaws 160 are prevented from moving apart from one another, thus locking the aiming guide 106 and the implant 102 together. The locking channel 164 may, for example, extend longitudinally along the body 154 to intersect with the third portion 166c of the slot 166. It will be understood by those of skill in the art that the system 100 may be utilized in a minimally invasive procedure via a small incision along a portion of the spine corresponding to a position of the vertebrae 10, 12. Thus, if the implant 102 were inadvertently disengaged from the aiming guide 106, the implant 102 would be difficult to locate via the small incision. To unlock the aiming guide 106 and the implant 102, the locking rod 162 may be removed from the locking channel 162 such that the jaws 160 may be flexed apart from one another by the slot 166.

Figure 9:
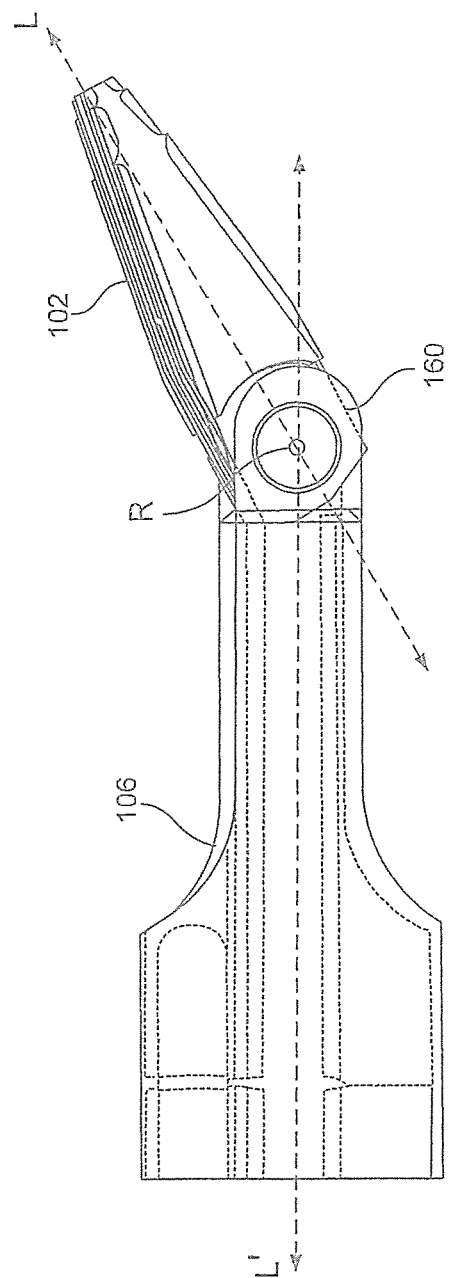
FIG. 9 shows an enlarged view of a distal portion of the aiming guide and implant of FIG. 7.

As shown in FIG. 9, once the aiming guide 106 and the implant 102 have been coupled to one another, the aiming guide 106 is pivotable with respect to the implant 102 about the rotation axis R such that the longitudinal axis L of the implant 102 may be angled with respect to the longitudinal axis L' of the aiming guide 106. The aiming guide 106 may be pivoted between a neutral position in which the central channel 168 is aligned with the central opening 124 of the implant 102 (i.e., the longitudinal axes L, L' are coaxial), a first position in which the first guide channel 172 is substantially coaxial and aligned with the first opening 110 and a second position in which the second guide channel 174 is substantially coaxial and aligned with the second opening 112. The first and second positions are defined by the first and second abutting surfaces 142, 144 of the implant 102. In particular, in the first position, the first abutting surface 142 abuts a portion of the distal end 158 of the body 154 of the aiming guide 106, preventing the aiming guide 106 from moving beyond a desired maximum angle of pivot relative to the implant 102 in a first direction. In the second position, the second abutting surface 144 abuts a portion of the distal end 158, preventing the aiming guide 106 from moving beyond a desired maximum angle of pivot relative to the implant 102 in a second direction.

Figure 10:
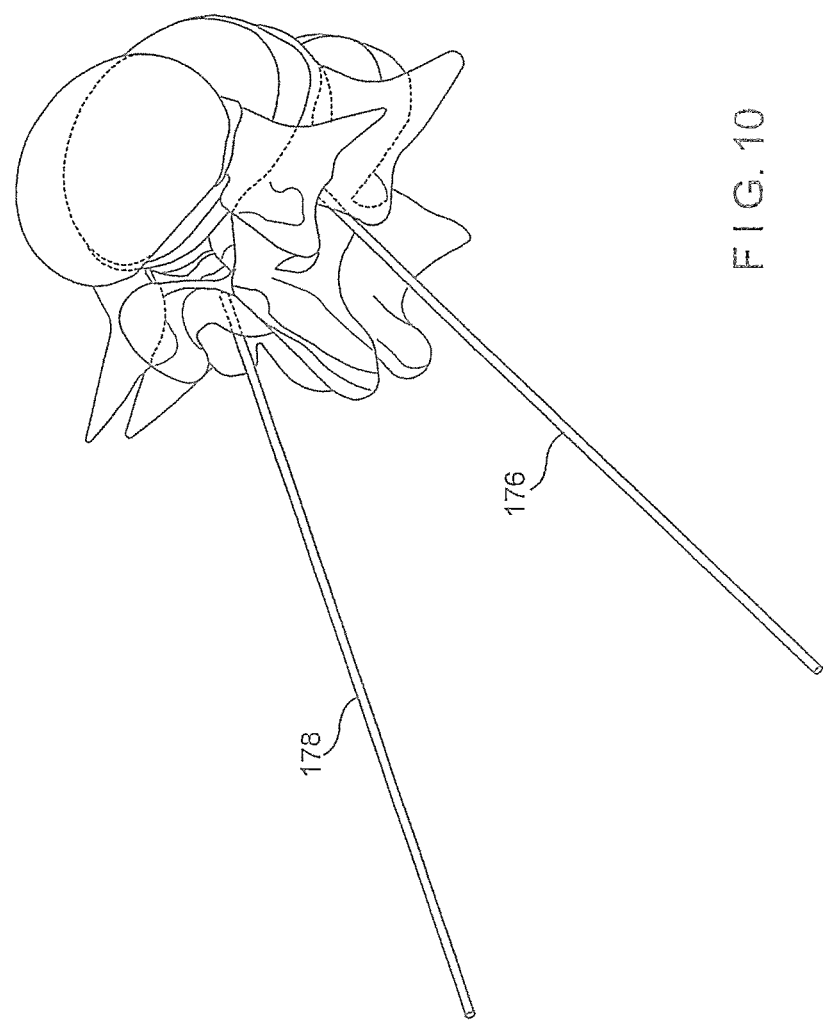
FIG. 10 shows a perspective view of guide wires inserted into a facet joint according to an exemplary method of the present invention.
Figure 11:
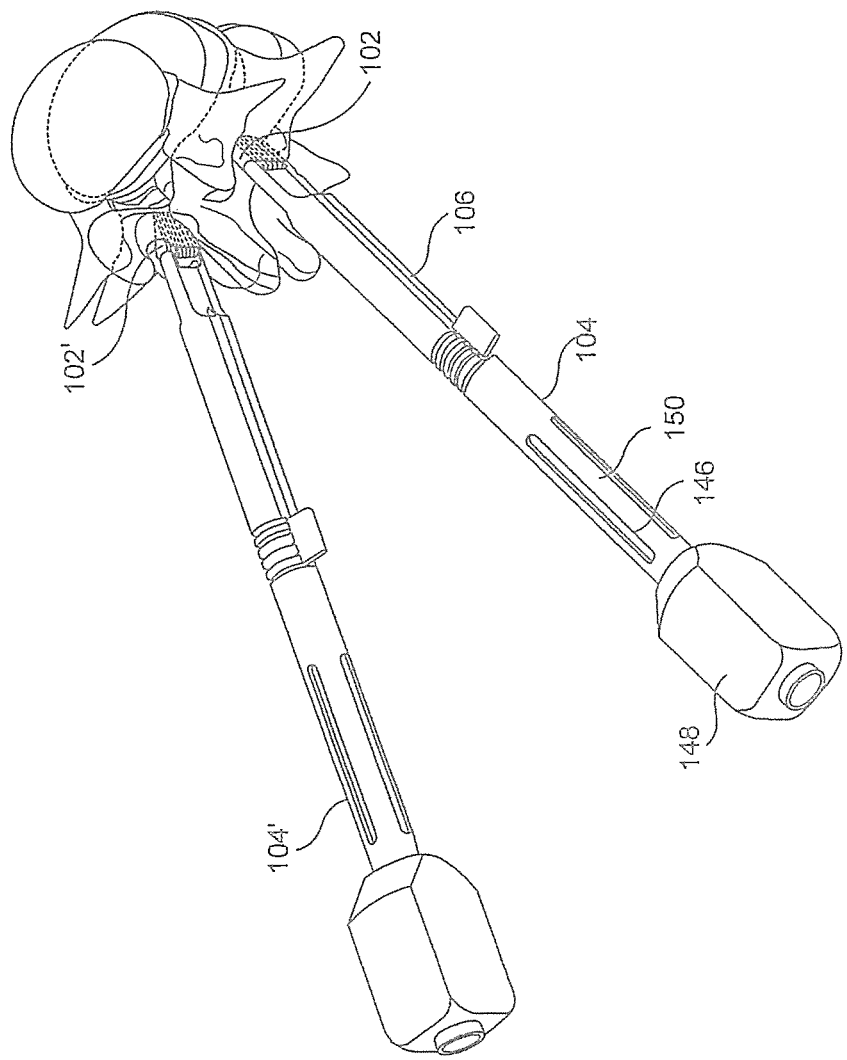
FIG. 11 shows a perspective view of an insertion tool and implant slid over the guide wires according to the method of FIG. 10.

FIGS. 10-16 show an exemplary surgical method using the system 100. As shown in FIG. 10, the method comprises inserting a first guide wire 176 into a facet joint between the first and second vertebrae 10, 12. For example, the first guide wire 176 may be inserted into a right facet joint. If it is desired to insert an implant in each of the right and left facet joints, a second guide wire 178 may be inserted into the other facet joint (e.g., left facet joint). The insertion tool 104 may be coupled to the implant 102, as described above, such that longitudinal axes of the impactor 146, the aiming guide 106 and the implant 102 are substantially coaxial with one another. The locking rod 162 may be inserted into the locking channel 164 to ensure that the aiming guide 106 and the implant 102 remain coupled during the entire surgical process. The coupled insertion tool 104 and the implant 102 may then be slid over the first guide wire 176, as shown in FIG. 11, such that the first guide wire 176 is received within the central openings 124 of the implant 102 and the central channels 170, 168 of the impactor 146 and the aiming guide 106 such that the implant 102 is in the neutral position relative to the aiming guide 106. The guide wire 176 ensures that the impactor 146 and the implant 102 are aligned such that an impacting tool may be used to impact the implant 102 by applying a force to the head 148 of the impactor 146 such that the implant 102 penetrates a capsule covering the facet joint and is inserted into the facet joint. The tapered second end 116 of the implant 102 facilitates penetration of the capsule. A second insertion tool 104', which is substantially similar to the insertion tool 104, may be coupled to the second implant 102 and similarly slid over the second guide wire 178. It will be understood by those of skill in the art that although they will not be discussed in detail, all of the steps described in regard to the insertion tool 104 and the implant 102 may be repeated for the second insertion tool 104' and the second implant 102'. It will also be understood by those of skill in the art that although the figures show the implant 102' and the insertion tool 104', it may be desired to implant only a single implant 102 in either the right or left facet joint.

Figure 12:
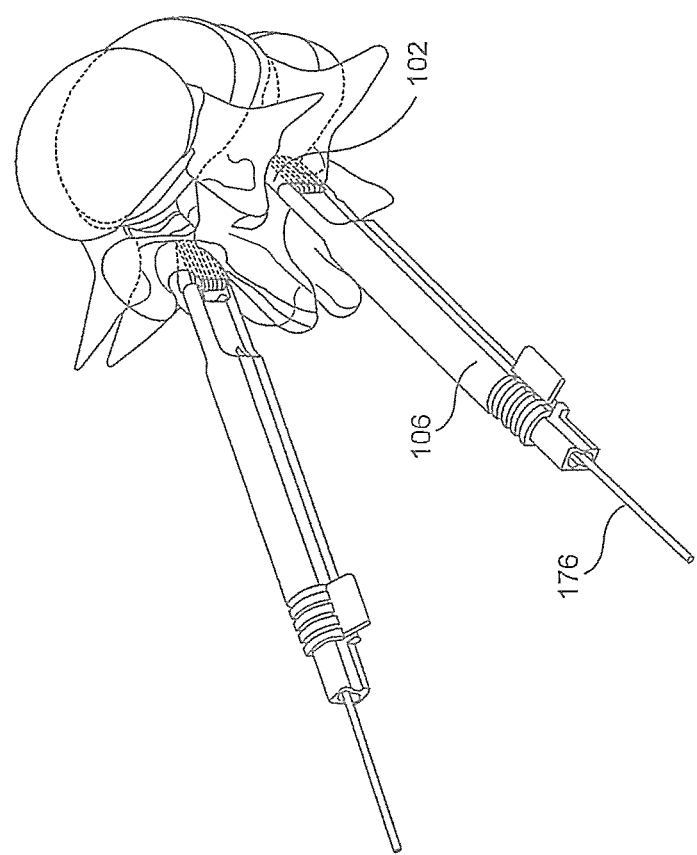
FIG. 12 shows a perspective view of the aiming guide attached to the implant according to the method of FIG. 10.
Figure 13:
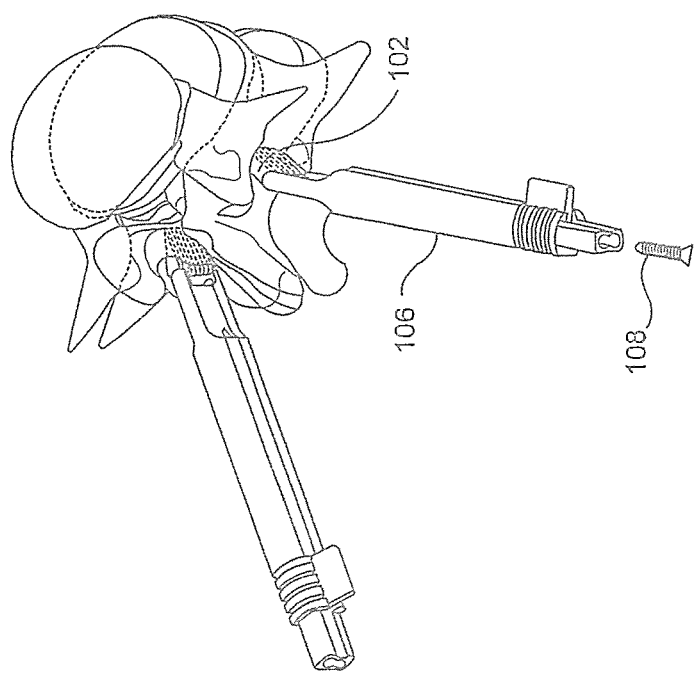
FIG. 13 shows a perspective view of the aiming guide in a first position relative to the implant according to the method of FIG. 10.

Once the implant 102 has been impacted into the facet joint, the impactor 146 maybe disengaged from the aiming guide 106 such that only the aiming guide 106 and the implant 102 remain mounted over the first guide wire 176, as shown in FIG. 12. The first guide wire 176 may then be removed such that the aiming guide 106 may be pivoted with respect to the implant 102. The aiming guide 106 is pivoted about the rotation axis R of the implant 102 until the aiming guide 106 is in the first position (i.e., the first abutting surface 142 of the implant 102 abuts a portion of the distal end 158 of the aiming guide 106), as shown in FIG. 13, and the first guide channel 172 is aligned with the first opening 110. A drill or awl may be inserted through the first guide channel 172 to drill a hole into inferior process 16 of the first vertebra 10 in alignment with the first axis A of the first opening 110. The bone fixation element 108 may be inserted through the first guide channel 172 and into the first opening 110 such that a head of the fixation element 108 engages the first opening 110 while a shaft extends into the inferior process 16 fixing the implant 102 to the first vertebra 10.

Figure 14:
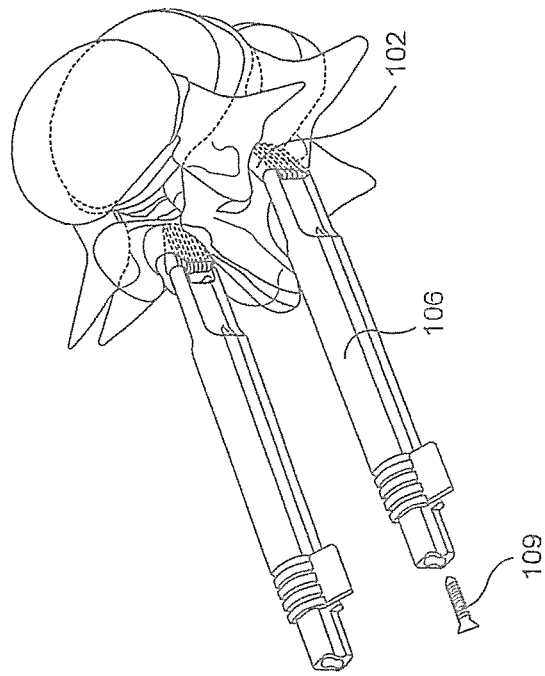
FIG. 14 shows a perspective view of the aiming guide in a second position relative to the implant according to the method of FIG. 10.
Figure 16:
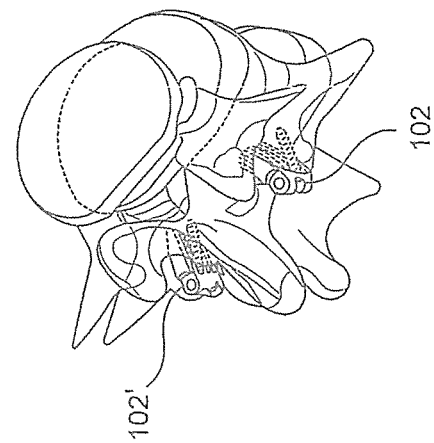
FIG. 16 shows a perspective view of an addition implant fixed within another facet joint according to the method of FIG. 10.
Figure 15:
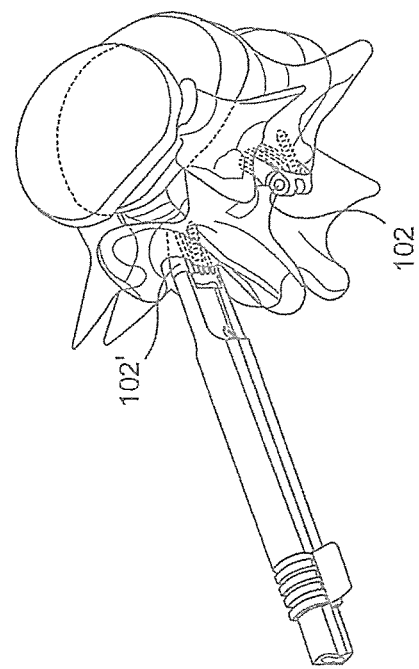
FIG. 15 shows a perspective view of the implant fixed within the facet joint according to the method of FIG. 10.

As shown in FIG. 14, the aiming guide 106 may then be pivoted to the second position relative to the implant 102 (i.e., the second abutting surface 144 of the implant 102 abuts a portion of the distal end 158 of the aiming guide 106) such that the second guide channel 174 is aligned with the second opening 112 of the implant 102. A hole may be drilled in the superior articular process 14 of the second vertebra 12 via the second guide channel 174 and the bone fixation element 109 inserted therethrough to engage the second opening 112. A head of the bone fixation element 109 engages the second opening while a shaft of the bone fixation element 109 extends into the superior articular process 14 such that the implant 102 is fixed to the second vertebra 12. It will be understood by those of skill in the art, however, that in an alternate embodiment, the second bone fixation element 109 may be inserted into the second opening 112 prior to insertion of the first bone fixation element 108 into the first opening 110. Once both the first and second bone fixation elements 108, 109 have been inserted into the first and second openings 110, 112, respectively, the aiming guide 106 is moved to the neutral position and the locking rod 162 removed therefrom so that the aiming guide 106 may be decoupled from the implanted implant 102, as shown in FIG. 15. The above-described steps may be similarly repeated for the implant 102' using an aiming guide 106' of the insertion tool 104', until the implant 102 is fixed within the second facet joint, as shown in FIG. 16. It will be understood by those of skill in the art that the implantation of both implants 102, 102' is not required. It may be desired to implant a single implant 102 in either of the right or left facet joint.

Figure 18:
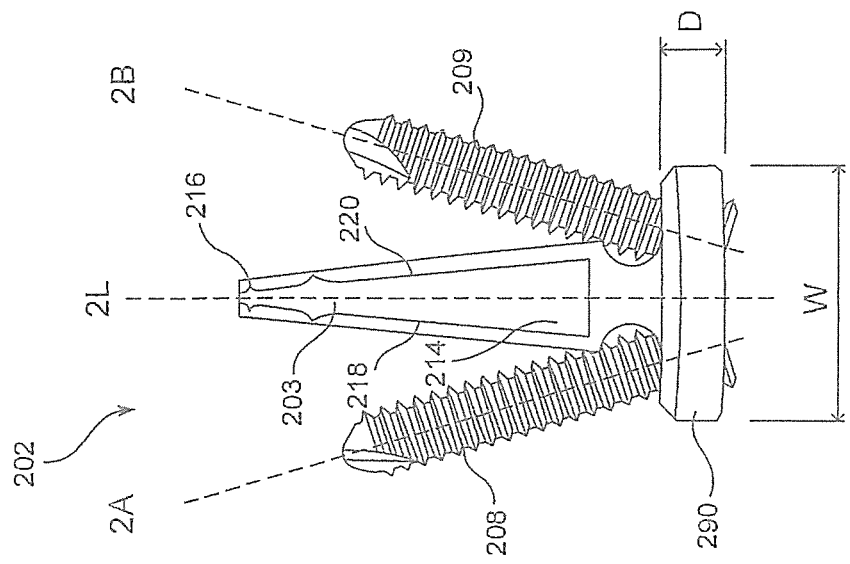
FIG. 18 shows a top plan view of the implant of FIG. 17.
Figure 17:
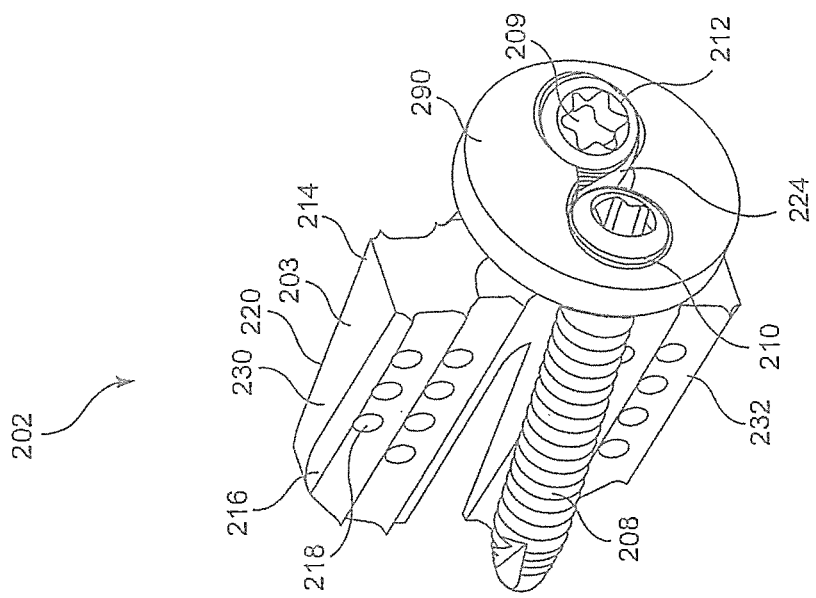
FIG. 17 shows a perspective view of an implant according to another exemplary embodiment of the present invention.

As shown in FIGS. 17-18, an implant 202 according to another exemplary embodiment may be substantially similar to the implant 102, described above in regard to the system 100. Similarly to the implant 102, the implant 202 may have a body 203 that is substantially wedge-shaped, tapering from a first end 214 to a second end 216 along a longitudinal axis 2L. The implant 202 is defined by first and second substantially planar surfaces 218, 220 which extend from the first end 214 to the second end 216 at an angle with respect to the longitudinal axis 2L to form the tapered wedge shape, and third and fourth lateral surfaces 230, 232 which connect the first and second surfaces 218, 220. The implant 202, however, further includes a head portion 290 attached to the first end 214 of the body 203 and having a width (i.e., a distance of the head portion 290 extending across the longitudinal axis 2L) greater than a width W of the first end 214 of the body 203 (i.e., a distance between the first and second surfaces 218, 220 at the first end 214). For example, the width may be approximately 10 mm. In one embodiment, the head portion 290 may be substantially circular such that width corresponds to a diameter of the head portion 290. It will be understood by those of skill in the art, however, that the head portion 290 may be any of a variety of shapes and sizes so long as the head portion 290 is wider than the first end 214 of the body 203. The larger width of the head portion 290 acts as a stop to prevent the head portion 290 from being inserted into the facet joint. Thus, the implant 202 may be easily removed, if so desired. The head portion 290 may also include a coupling feature configured for attachment to an insertion and/or removal instrument as would be understood by those skilled in the art.

Similarly to the implant 102, the implant 202 includes a central opening 224 extending through the head portion 290 and the body 203 along the longitudinal axis 2L to accommodate a guide wire therethrough along with first and second openings 210, 212 extending therethrough to accommodate bone fixation elements 208, 209. The first and second openings 210, 212, however, extend only through the head portion 290. In particular, the first opening 210 extends through the head portion 290 along a first axis 2A, which is angled with respect to the longitudinal axis 2L in a first direction such that the bone fixation element 208 may be inserted through the first opening 210 along the first axis 2A and into a first vertebra of the facet joint. The second opening 212 extends through the head portion 290 along a first axis 2B, which is angled with respect to the longitudinal axis 2L in a second direction opposite the first direction such that the bone fixation element 209 may be inserted through the second opening 212 along the first axis 2B and into a second vertebra of the facet joint. For example, the central axis, the first axis 2A may be angled with respect to the longitudinal axis 2L at an angle of between approximately 5° and 45° and, more particularly, between 10° and 20° while the second axis 2B may be angled with respect to the longitudinal axis 2L at an angle of between approximately 100 and 20°. In an exemplary embodiment, having an angle of approximately 15°, this angle permits a surgeon or other user to insert the bone fixation elements 208, 209 through the first and second holes 210, 212, respectively, without the use of an aiming guide, as discussed above in regard to the system 100. It will be understood by those of skill in the art, however, that the first and second axes 2A, 2B may be at any of a variety of angles with respect to the longitudinal axis 2L so long as the bone fixation elements 208, 209 received within the openings 210, 212 therealong are inserted into first and second vertebrae of the facet joint.

A depth D of the head portion 290 (i.e., a distance of the head portion 290 along the longitudinal axis 2L) may be between approximately 2.0 to 3.0 mm such that the first and second holes 210, 212 may receive heads of the first and second bone fixation elements 208, 209, respectively, therein. Inner surfaces of the holes 210, 212 may include threading to engage threads along the heads of the first and second bone fixation elements 208, 209 so that shafts thereof extend into the first and second vertebrae of the facet joint to fix the implant 202 thereto.

The implant 202 may also be substantially symmetrical about the longitudinal axis 2L such that the implant 202 may be utilized for either facet joint—i.e., a left side or a right side—and would not require a "left" and "right" side configuration. In particular, the body 203 may have a substantially symmetrical wedge shape, and the first and second axes 2A, 2B of the first and second openings 210, 212 may also be symmetrical about the longitudinal axis 2L. The implant 202 may be implanted into the facet joint by sliding the implant 202 over a guide wire received within the central opening 224 until the head portion 290 prevents further movement thereof. The guide wire may then be removed so that bone fixation elements 208, 209 may be inserted through the first and second openings 210, 212, respectively, and into the first and second vertebrae to fix the implant 202 thereto.

Figure 19:
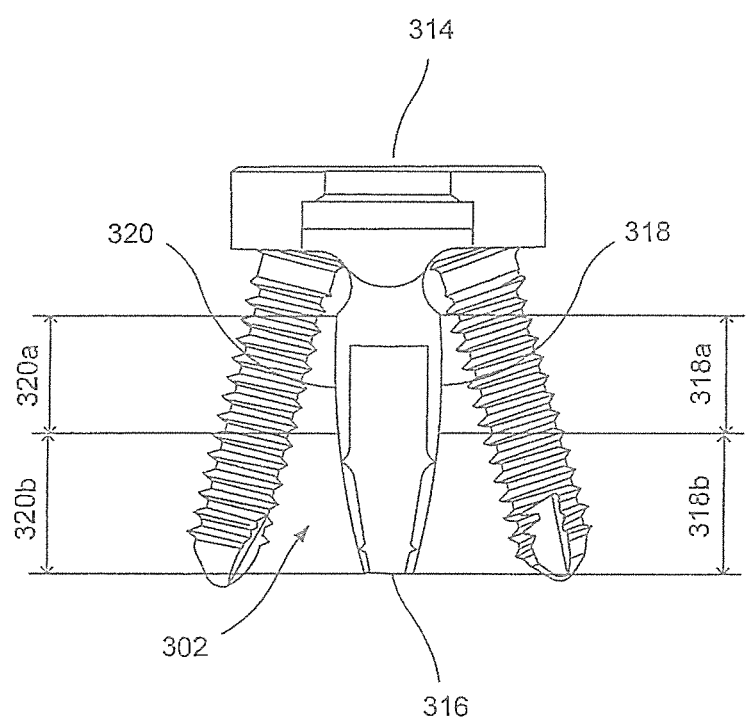
FIG. 19 shows a top plan view of an implant according to yet another embodiment of the invention.
Figure 20:
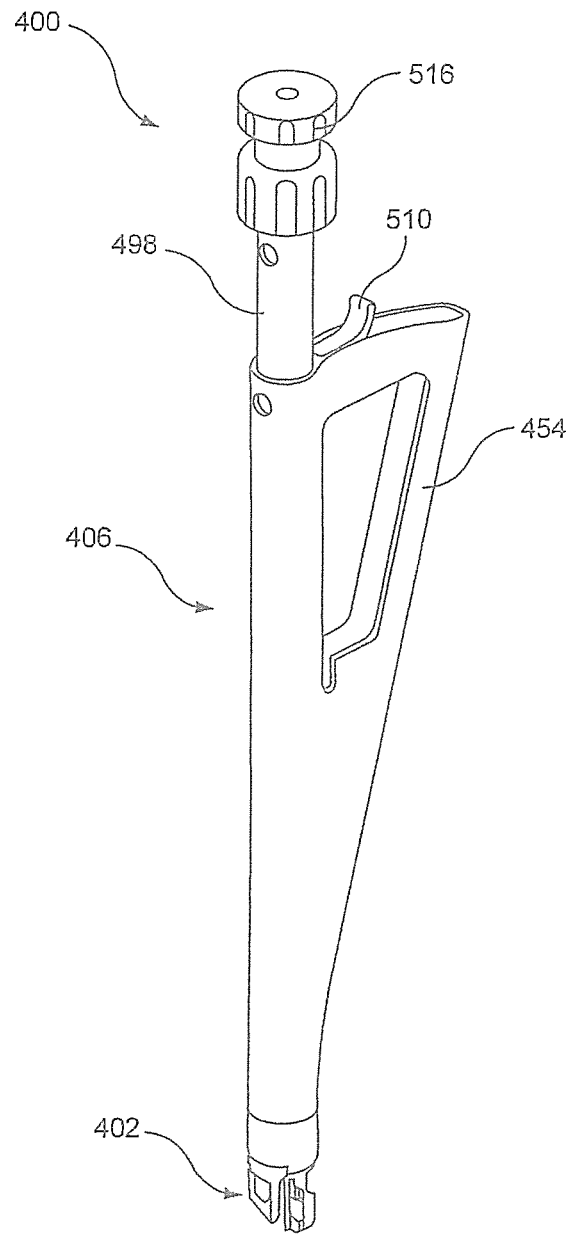
FIG. 20 shows a perspective view of a system according to another exemplary embodiment of the present invention.
Figure 21:
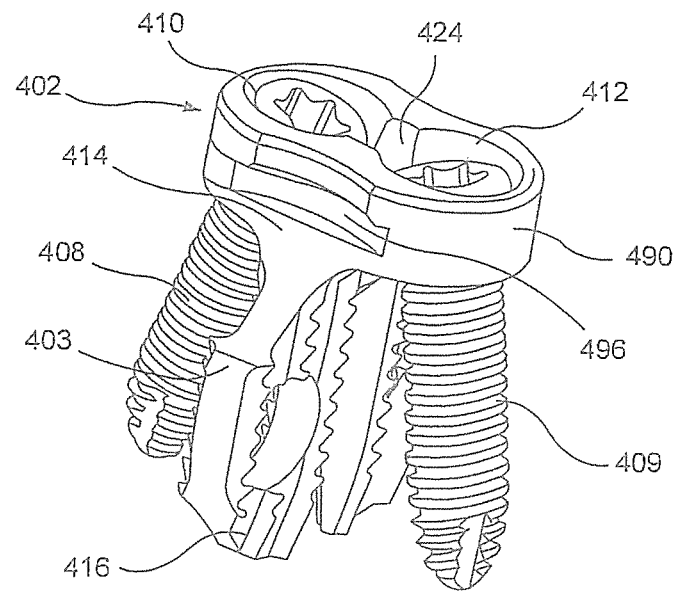
FIG. 21 shows a perspective view of an implant of the system of FIG. 20.
Figure 22:
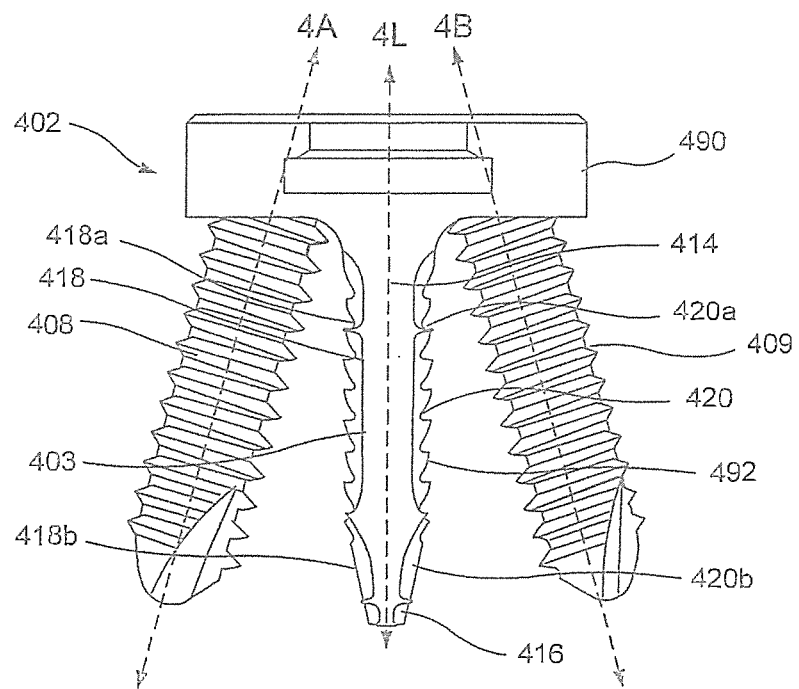
FIG. 22 shows a side view of an implant of the implant of FIG. 21.

The implants 102, 202 have been described as wedge-shaped. However, as those skilled in the art will understand, other implant shapes are possible. For example, as shown in FIG. 19 an implant 302 is similar to the implants 102, 202, with a first end 314 and a second end 316 along a longitudinal axis, and first and second surfaces 318, 320, respectively. The implant 302 is used substantially the same the manner described for implant 202. In contrast to the implants 102, 202, the surfaces 318, 320 define a more pronounced transition from a second end 316 to a first end 314 along the longitudinal axis. When compared with the gradual opening of the facet joint due to the wedge shape of the exemplary implants 102, 202, the opening of the facet joint with the implant 302 is more abrupt.

The relatively abrupt transition is provided by a shape of the implant 302 defined by the first and second surfaces 318, 320 and an insertion surface at the second end 316 that connects the first and second surfaces 318, 320. Each of the first and second surfaces 318, 320 has first regions 318a, 320a, respectively, and second regions 318b, 320b, respectively. The portions of the surfaces 318, 320 in the first regions 318a, 320a are substantially planar and substantially parallel to each other. In the second regions 318b, 320b, the first and second surfaces 318, 320 are shaped to provide a smooth insertion transition in an insertion direction from the second end 316 to the first end 314. The smooth transition maybe provided by portions of the surfaces 318, 320 in the second regions 318b, 320b defining curved or planar surfaces that widen from the second end 316 in a direction toward the first regions 318a, 320a.

The insertion surface defined at the second end 316 is, in normal use, the first part of the implant 302 that contacts the facet joint during insertion. The insertion surface provides the initial opening of the facet joint. To provide the relatively abrupt opening, the insertion surface could be described as having a blunt profile. The blunt profile may be defined by an insertion surface which is planar, arced, bullet-shaped, and other surface shapes as those skilled in the art would understand. In comparison with insertion surfaces of second ends 116, 216 of the other exemplary implants 102, 202, the insertion surface of the second end 316 is relatively wider to provide a more abrupt opening. Since the inferior and superior surfaces of facet joint are substantially parallel to one another the parallel planar portions 318a, 320b of the surfaces 318, 320 fit well anatomically to the facet joint.

Figure 33:
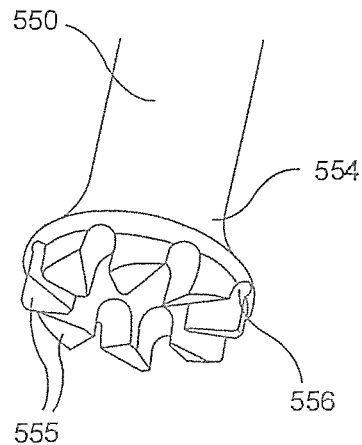
FIG. 33 shows an enlarged perspective view of a distal end of the reamer of FIG. 31.
Figure 35:
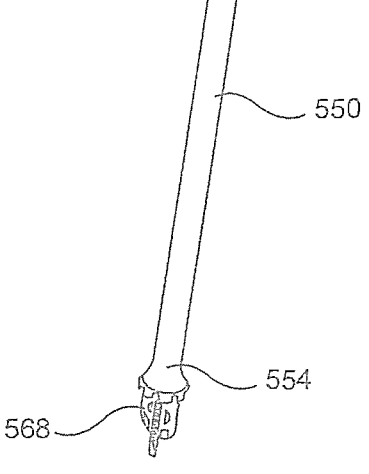
FIG. 35 shows an enlarged perspective view of a distal portion of the curette and reamer of FIG. 34.
Figure 34:
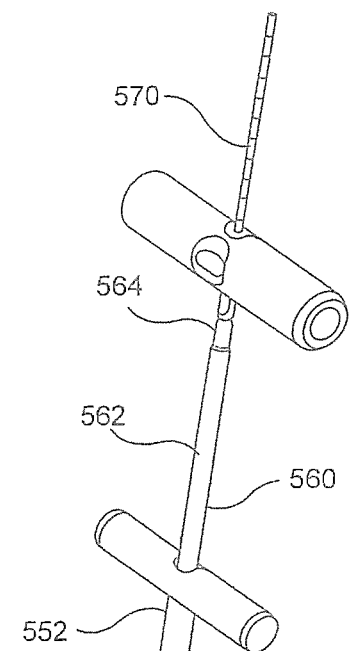
FIG. 34 shows a perspective view of a curette and reamer according to the system of FIG. 20.

As shown in FIGS. 20-35, system 400 according to another exemplary embodiment of the present invention comprises an implant 402 and an implant holder 406. The implant 402 may be substantially similar to the implant 302, described above, comprising a body 403 sized and shaped for insertion into a facet joint and extending from a first end 414 to a second end 416, and a head portion 490 attached to the first end 414. The system 400 may further comprise a facet joint finder 530, as shown in FIGS. 31-32, for locating the facet joint, a reamer 550, as shown in FIGS. 31 and 33, for removing soft tissue and creating a seating surface for the implant 402 and a curette 560, as shown in FIGS. 34-35, for removing cartilage from the facet joint to facilitate insertion of the implant 402 therein, as will be described in further detail below, As shown in FIGS. 21-25, the implant 402 includes a central opening 424 extending through the head portion 490 and the body 403 along a longitudinal axis 4L to accommodate a guide wire therethrough along with first and second openings 410, 412 extending through the head portion 490 to receive bone fixation elements 408, 409 therethrough. The first opening 410 extends along a first axis 4A, which is angled with respect to the longitudinal axis 4L, such that a first bone fixation element 408 be inserted through the first opening 410 extends along the first axis 4A which, when the implant 402 is in a desired position will aim the first bone fixation element 408 along a desired path into a first vertebra of a facet joint. The second opening 412 extends along a second axis 4B angled with respect to the longitudinal axis 4L in a second direction opposite the first axis 4A such that, when the implant 402 is in the desired position, a second bone fixation element 409 inserted through the second opening 412 extends along the second axis 4B into a second vertebra along a desired path. The angle between the first axis 4A and the longitudinal axis 4L and the angle between the first axis 4B and the longitudinal axis 4L in this embodiment are substantially equal to one another such that the implant 402 is substantially symmetrical with respect to the longitudinal axis 4L. The implant holder 406 is used to insert the implant 402 into the facet joint and guide the bone fixation elements 408, 409 into the first and second openings 410, 412, respectively. The head portion 490 of the implant 402 according to this embodiment also includes a recess 496 along opposing portions of a periphery thereof for engaging a portion of the implant holder 406.

Similarly to the implant 402, a shape of the body 403 transitions from the first end 414 to the second end 416 and is defined by first and second surfaces 418, 420 thereof. In particular, as described above in regard to the implant 302, each of the first and second surfaces 418, 420 has first regions 418a, 418b, respectively, and second regions 420a, 420b, respectively. The first regions 418a, 420a are substantially planar and parallel to one another while the second regions 418b, 420b taper toward the second end 416 to provide a smooth insertion transition. The body 403 also includes a plurality of ribs 422 projecting from each of the first and second surfaces 418, 420 to guide the implant 402 into the facet joint and facilitate engagement with the first and second vertebra. The ribs 422 extend along the surfaces 418, 420 from the first end 414 to the second end 416. The ribs 422, however, further include teeth 492 or a jagged edge extending therealong to enhance a grip between the implant and the surrounding tissue to prevent the implant 402 from being inadvertently pulled out of a facet joint into which it has been inserted. As would be understood by those skilled in the art, the teeth 492 are angled with peaks 494 thereof pointing toward the first end 414 to increase a pull-out resistance of the implant 402.

In addition, rather than a plurality of smaller holes extending through the body 403 to promote bone in-growth, as shown and described in regard to the implants 102-302, the implant 402 includes larger first and second holes 480, 481 extending through the body 403. The first hole 480 extends through a first portion of the body 403 from the first surface 418 to the second surface 420 on a first side of the central opening 424. The second hole 481 extends through a second portion of the body 403 from the first surface 418 to the second surface 420 on a second side of the central opening 424 opposite the first side. The first and second holes 480, 481 are sized and shaped to permit the holes 480, 481 to be filled with bone graft material to promote bone growth during the implantation process.

Figure 26:
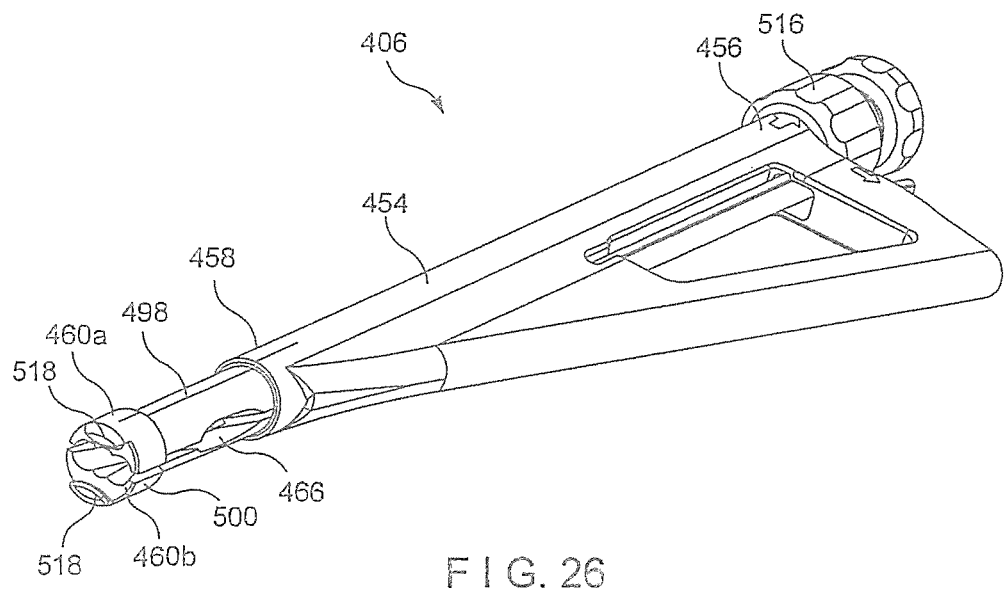
FIG. 26 shows a perspective view of an implant holder of the system of FIG. 20, in an implant receiving configuration.
Figure 27:
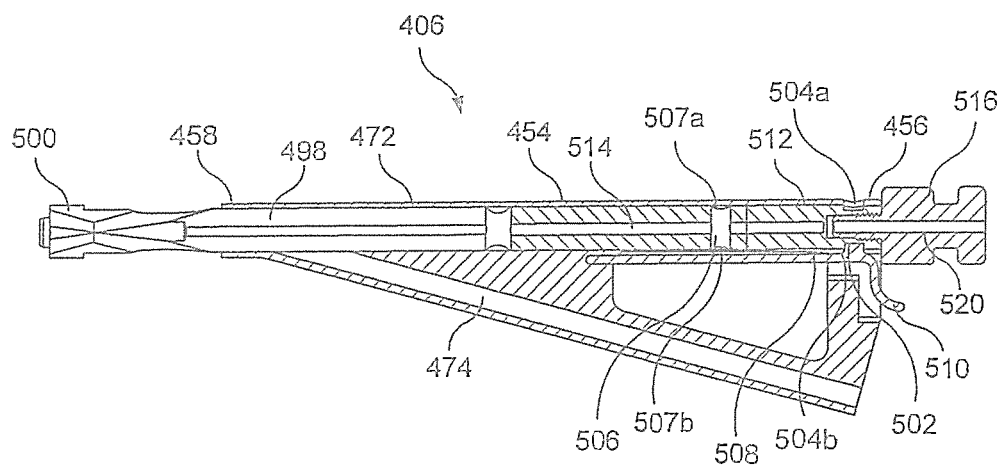
FIG. 27 shows a longitudinal cross-sectional view of the implant holder of FIG. 26, in the implant receiving configuration.
Figure 28:
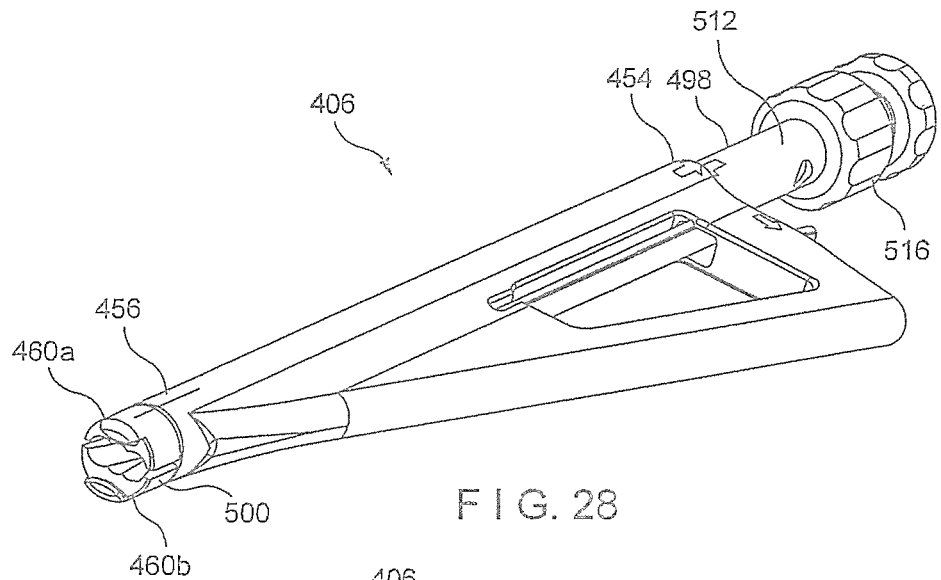
FIG. 28 shows a perspective view of the implant holder of FIG. 26, in a closed configuration.
Figure 29:
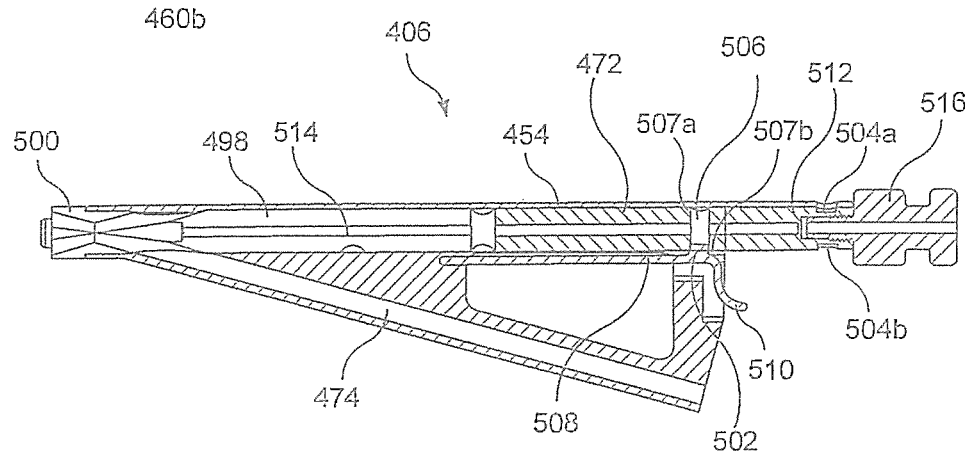
FIG. 29 shows a longitudinal cross-sectional view of the implant holder of FIG. 26, in the closed configuration.

As shown in FIGS. 26-30, the implant holder 406 includes a guide body 454 including a central channel 472 extending from a proximal end 456 to a distal end 458 and a shaft 498 slidably received within the central channel 472. The shaft 498 extends along a longitudinal axis to a distal end 500 which is configured to engage the head portion 490 of the implant 402. In particular the distal end 500 includes jaw members 460a, 460b extending distally therefrom on opposing sides of the shaft 498. The jaw members 460a, 460b are biased away from one another such that the head portion 490 may be received therebetween. The guide body 454 is slidable over the shaft 498 between an implant receiving configuration, as shown in FIGS. 26 and 27, in which the jaw members 460a, 460b receive the head portion 490 therebetween and a closed configuration, as shown in FIGS. 28 and 29, in which the jaw members 460a, 460b are moved toward one another to engage the recesses 496 to hold the implant 402 therebetween.

The guide body 454 includes a central channel 472 sized and shaped to slidably house the shaft 498 therein and a guide channel 474 extending through the guide body 454 at an angle relative to the central channel 472. The central channel 472 extends through the guide body 454 along a path oriented so that, when the shaft 498 engages the implant 402, the central channel 472 is aligned with the longitudinal axis 4L of central opening 424. The guide channel 474 extends through the guide body 472 such that when the shaft 498 engages the implant 402, the guide channel 474 is aligned with one of the first and second axes 4A, 4B of the first and second openings 410, 412, respectively. The guide body 454 is thus rotatable about the shaft 498 so that, when coupled to the implant 402, the guide channel 474 may be moved between a first hole configuration in which the guide channel 474 is aligned with the first opening 410 and a second hole configuration in which the guide channel 474 is aligned with the second opening 412. The guide body 454 also includes a locking mechanism 508 including a locking tab 502 biased toward a center of the central channel 472 to engage portions of the shaft 498 to fix the guide body 454 relative to the shaft 498 in one of the implant receiving or closed configuration and/or the first hole and second hole configurations. The locking mechanism 508 also includes a release lever 510 which may be used to draw the locking tab 502 out of engagement with the portions of the shaft 498 as will be described in further detail below.

Figure 30:
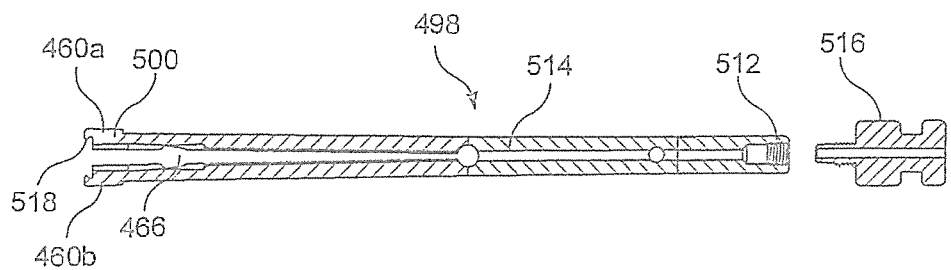
FIG. 30 shows a longitudinal cross-sectional view of a shaft of the implant holder of FIG. 26.
Figures 31, 32:
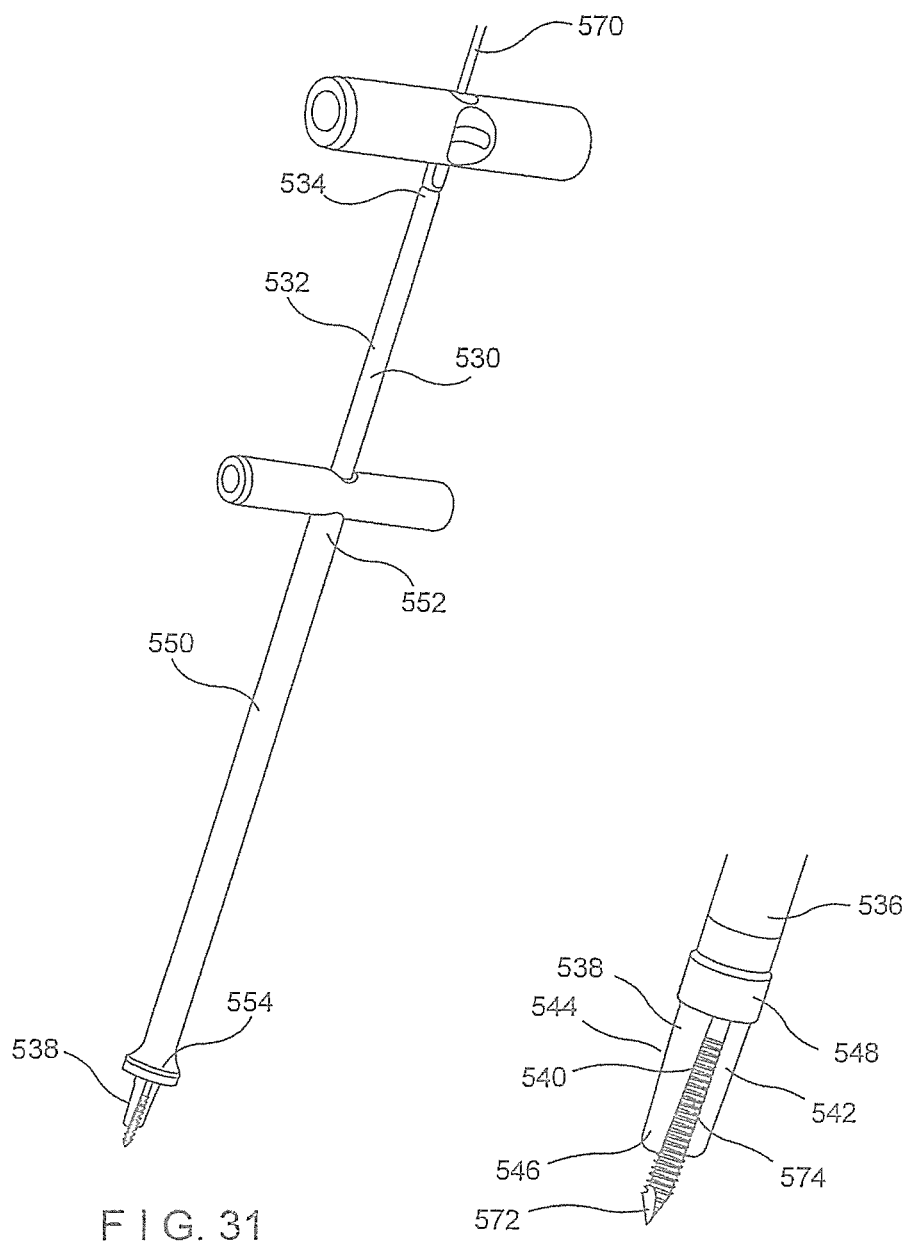
FIG. 31 shows a perspective view of a joint finding tool and a reamer according to the system of FIG. 20.
FIG. 32 shows an enlarged perspective view of a distal end of the joint finding tool of FIG. 31.

The shaft 498, as shown in FIG. 30, extends longitudinally from a proximal end 512 to the distal end 500 and includes a lumen 514 extending therethrough. The lumen 514 is sized and shaped to permit the implant holder 406 to be slid over a guide wire to insert the implant 402 into the facet joint. The proximal end 512 is configured to be coupled to an end cap 516 which may be used to hold the shaft 498 while the body 454 is moved between the implant receiving and closed configurations. The end cap 516 also includes a corresponding lumen 520 such that the guidewire may extend through both the end cap 516 and the shaft 498. As described above, the distal end 500 includes jaw members 460a, 460b for engaging the head portion 490 of the implant. The jaw members 460a, 460b may be formed via, for example, a slot 466 extending along a length of a distal portion of the shaft 498. The jaw members 460a, 460b may further include protrusions 518 extending radially inward from a portion thereof, the protrusions 518 sized and shaped to correspond to the recesses 496 in the head portion 490 of the implant 402.

The shaft 498 includes first and second locking recesses 504a, 504b extending along a proximal portion of the shaft 498 for engaging the locking tab 502 to lock the implant holder 406 in the implant receiving configuration. The first and second locking recesses 504a, 504b in this embodiment are substantially diametrically opposed from one another. The locking tab 502 may be received in either of the first and second locking recesses 504a, 504b to lock the implant holder in the implant receiving configuration. The shaft 498 also includes a locking hole 506 extending laterally therethrough distally of the first and second locking recesses 504a, 504b. The locking hole 506 is sized and shaped to engage the locking tab 502 to lock the implant holder 406 in the closed configuration and one of the first and second hole receiving configurations.

The locking hole 506 extends entirely through the shaft 498 from a first opening 507a to a second opening 507b substantially opposing the first opening 507a. The first opening 507a may be longitudinally aligned with the first locking recess 504a while the second opening 507b is longitudinally aligned with the second locking recess 504b. The locking hole 506 is positioned distally of the first and second locking recesses 504a, 504b such that when the locking tab 502 engages the second locking hole 506, the implant holder 406 is locked in the closed configuration. Thus, in the implant receiving configuration, the distal end 500 of the shaft 498 may be positioned over the head portion 490 of the implant 402. Once the head portion 490 has been positioned between the jaw members 460a, 460b, as desired, a user moves the release lever 510 to disengage the locking tab 502 from the first locking hole 504 and slides the guide body 454 distally over the jaw members 460a, 460b until the implant holder 406 is in the closed configuration and the locking tab 502 engages the second locking hole 506. In the closed configuration, the guide body 454 is moved longitudinally over the jaw members 460a, 460b such that the protrusions 518 engage the recesses 496 of the head portion 490.

The distal portion of the shaft 498 also includes a first guide channel 522 and a second guide channel 524 extending therethrough. The first guide channel 522 extends through the distal portion of the shaft 498 at an angle relative to the longitudinal axis of the shaft 498 corresponding to an angle between the first axis 4A of the first opening 410 and the longitudinal axis 4L of the implant 402. The second guide channel 524 extends through the distal portion of the shaft 498 at an angle relative to the longitudinal axis of the shaft 498 corresponding to an angle between the second axis 4B of the second opening 412 and the longitudinal axis 4L of the implant 402. When the implant holder 406 is in the closed configuration, the guide channel 474 of the body 454 is aligned with one of the first and second guide channels 522, 524 of the shaft 498 such that one of the bone fixation elements 408, 409 may be guided therethrough into one of the first and second openings 410, 412 of the implant 402. In particular, when the locking tab 502 engages the first opening 507a of the locking hole 506, the implant holder 406 is locked in the first hole configuration such that the guide channel 474 is aligned with the first guide channel 522 of the shaft 498. When the locking tab 502 engaging the second opening 507b of the locking hole 506, the implant holder 406 is locked in the second hole configuration such that the guide channel 474 is aligned with the second guide channel 524 of the shaft 498. As discussed above, the implant holder 406 may be moved between the first and second hole configurations by pulling the release lever 510 to disengage the locking tab 502 from one of the first and second openings 507a, 507b of the locking hole 506 and rotating the guide body 454 about the shaft 498 until the locking tab 502 engages the other of the first and second openings 507a, 507b.

As shown in FIGS. 31 and 32, the facet joint finder 530 includes a shaft 532 extending longitudinally from a proximal end 534 to a distal end 536 attached to a joint finding tip 538 and a lumen extending therethrough to receive a guide wire therein. The joint finding tip 538 is sized and shaped to be inserted into a facet joint of a patient and includes first and second planar surfaces 542, 544 which taper toward one another to a distal end 546 thereof to facilitate insertion into the facet joint. A length of the joint finding tip 538 is selected to correspond to a length of the implant 402. The joint finding tip may also include a longitudinal slot 540 extending therealong to accommodate a guide wire that is wider than a distance between the first and second planar surfaces 542, 544. The facet joint finder 530 may also include a stop 548 extending radially outward from a portion of the shaft 532 immediately proximal the joint fording tip 538. The stop 548 prevents a reamer 550 which may be used in conjunction with the facet joint finder 530 from extending distally past the stop 548.

As shown in FIGS. 31 and 33, the reamer 550 extends longitudinally from a proximal end 552 to a distal end 554 and includes extending therethrough a lumen sized and shaped to receive the shaft 532 of the facet joint finder 530. The distal end 554 of the reamer 550 has, for example, a substantially circular distal face 556 including blades 558 extending therealong for removing soft tissue and creating a seating surface for receiving the head portion 490 of the implant 402.

As shown in FIGS. 34 and 35, the curette 560 includes a shaft 562 extending longitudinally from a proximal end 564 to a distal end 566 attached to an implant-shaped tip 568 and a lumen extending therethrough to accommodate a guide wire therein. As shown, the curette 560 may also be used in conjunction with the reamer 550 described above. Thus, the shaft 562 is sized and shaped to be slidably received within the lumen of the reamer 550. The implant-shaped tip 568 has a size and shape corresponding to the body 403 of the implant 402 to be inserted into the facet joint such that that the tip 568, when inserted into the facet joint, removes cartilage therefrom to accommodate insertion of the implant 402 therein. The curette 560 may also include a stop (not shown) extending radially outward from a portion of the shaft 562 proximal of the implant-shaped tip 568 such that when the curette is coupled with the reamer 550, the reamer 550 is prevented from moving distally past the stop.

Figure 36:
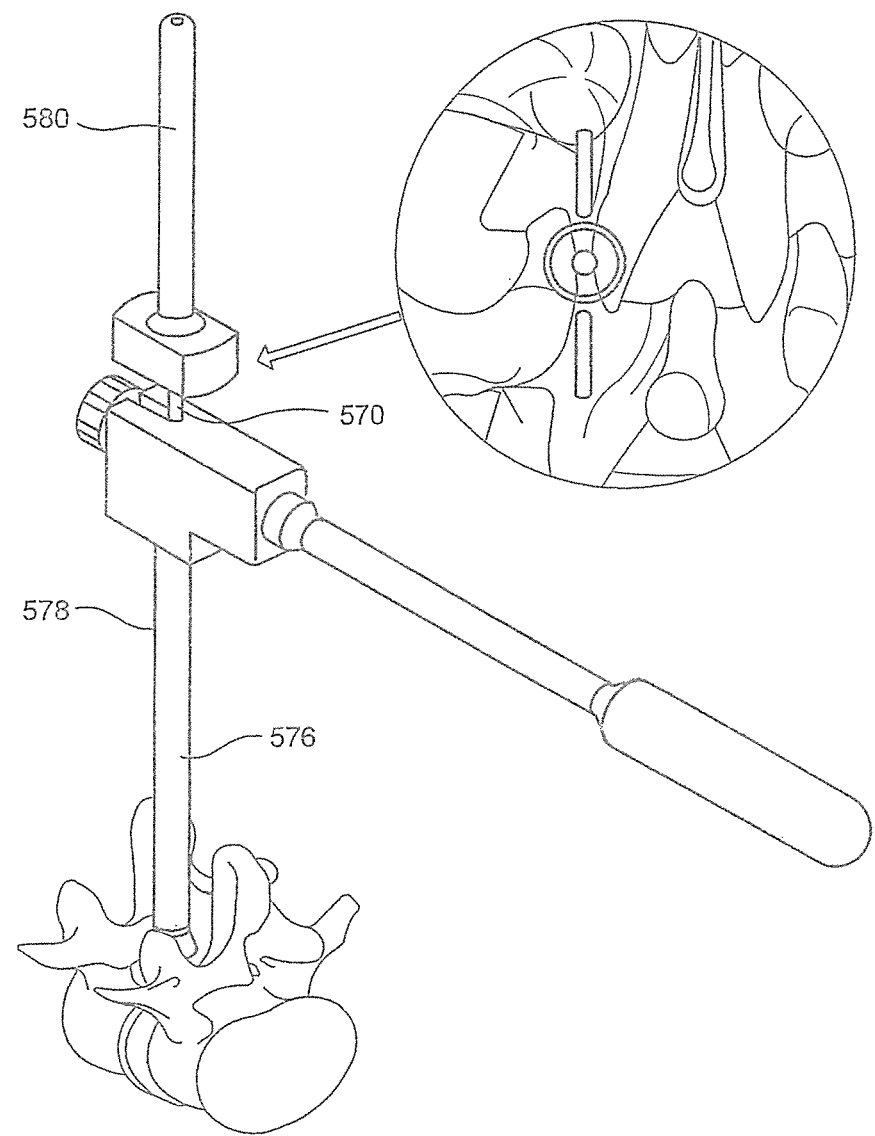
FIG. 36 shows a perspective view of a guide wire inserted into a joint via an aiming guide according to an exemplary surgical method of the present invention.
Figure 37:
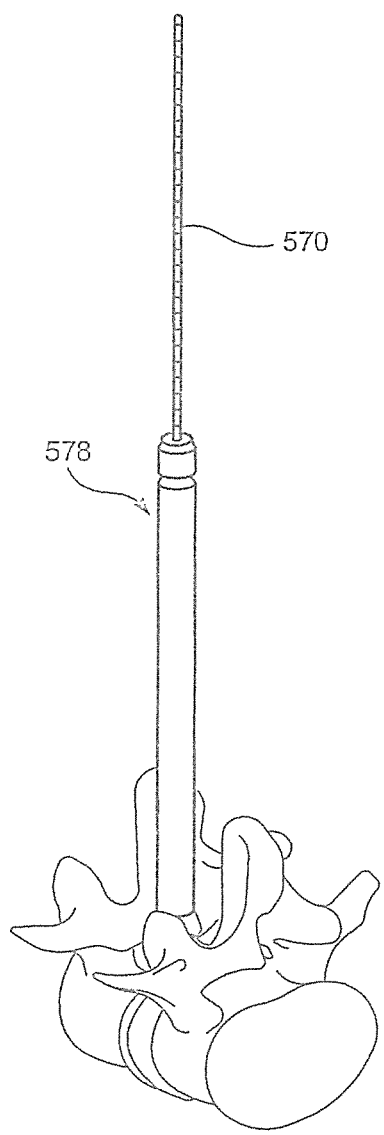
FIG. 37 shows a perspective view of a guide wire and shaft of the aiming guide of FIG. 36.
Figure 38:
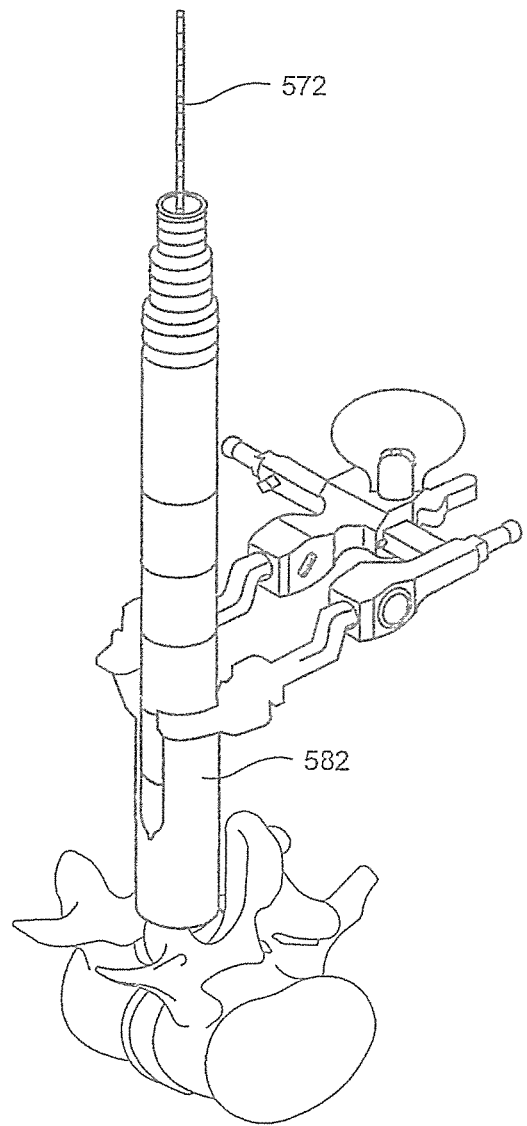
FIG. 38 shows a perspective view of a soft tissue retractor over the guide wire and aiming guide of FIG. 37.

FIGS. 36-43 show an exemplary surgical technique using the system 400. The surgical technique comprises inserting a guide wire 570 into the facet joint. In this exemplary embodiment, the guide wire 570 extends longitudinally to a distal end including a flat tip 572 and threads 574, as shown in FIG. 32, or teeth, as shown in FIG. 35, extending along a length of the guide wire 570 distally of the flat tip 572 to facilitate holding within the bone. In one exemplary embodiment, as shown in FIG. 36, the guide wire 570 is inserted into the joint using an aiming guide 576 including x-ray markers enabling visualization of the implant placement within the facet joint. The x-ray markers may include, for example, pins to indicate a width of the implant 402 to be inserted and a ring to show a size of the head portion 490. Once the x-ray markers indicate proper positioning, the distal end 572 the guide wire 570 is inserted through an aiming shaft 578 thereof and into the facet joint. As would be understood by those skilled in the art, a tamp 580 may be attached to the proximal end of the guide wire 570 to prevent the guide wire 570 from being inserted more than a desired distance (e.g., 15 mm) into the facet joint to prevent damage of neural structures. Once the guide wire has been inserted into the facet joint, an aiming handle may be removed from the aiming guide 576, as shown in FIG. 37, so that only the aiming shaft 578 remains about the guide wire 570. As shown in FIG. 38, a soft-tissue retractor 582 is then slid over the guide wire 570 and/or aiming shaft 578 to remove soft tissue surrounding the area in which the implant 402 is to be inserted.

According to another exemplary embodiment, as shown in FIG. 39, the guide wire 570 is placed within the facet joint via the facet joint finder 530. The joint finding tip 538 is inserted into the facet joint in which the implant 402 is to be inserted. Once positioned in the facet joint, the guide wire 570 is inserted through the shaft 532 of the facet joint finder 530 until the distal end 572 of the guide wire 570 is inserted into the facet joint. As described above, the distal end 572 should not be inserted more than a desired distance (e.g., 15 mm) into the joint to prevent damage to the neural structures. Once the guide wire 570 has been placed, as shown in FIG. 40, the reamer 550 is slid over the shaft 532 of the facet joint finder 530 until a distal end of the reamer 550 contacts the stop 548. The distal face 556 of the reamer 550 is used to create a surface for implant seating. The reamer 550 and the facet joint finder 530 may then be removed, leaving the guide wire 570 inserted in the facet joint. The soft tissue retractor 582 is then slid over the guide wire 570 to remove the soft tissue surrounding the implant area.

Once the guide wire 570 has been inserted into the facet joint and soft tissue has been removed using either of the methods described above, the curette 560 is slid over the guide wire 570 until the implant-shaped tip 568 is inserted into the facet joint to remove the cartilage in the facet joint, creating optimal conditions for bony fusion. If the surrounding bone has not been reamed already during the guide wire 570 placement, the reamer 550 may be slid over the shaft 562 of the curette 560 so that the distal face 556 may create a surface for implant seating. Once the cartilage has been removed, the curette 560 and/or the reamer 550 may be removed, leaving the guide-wire 570 inserted in the facet joint.

Figures 41, 42:
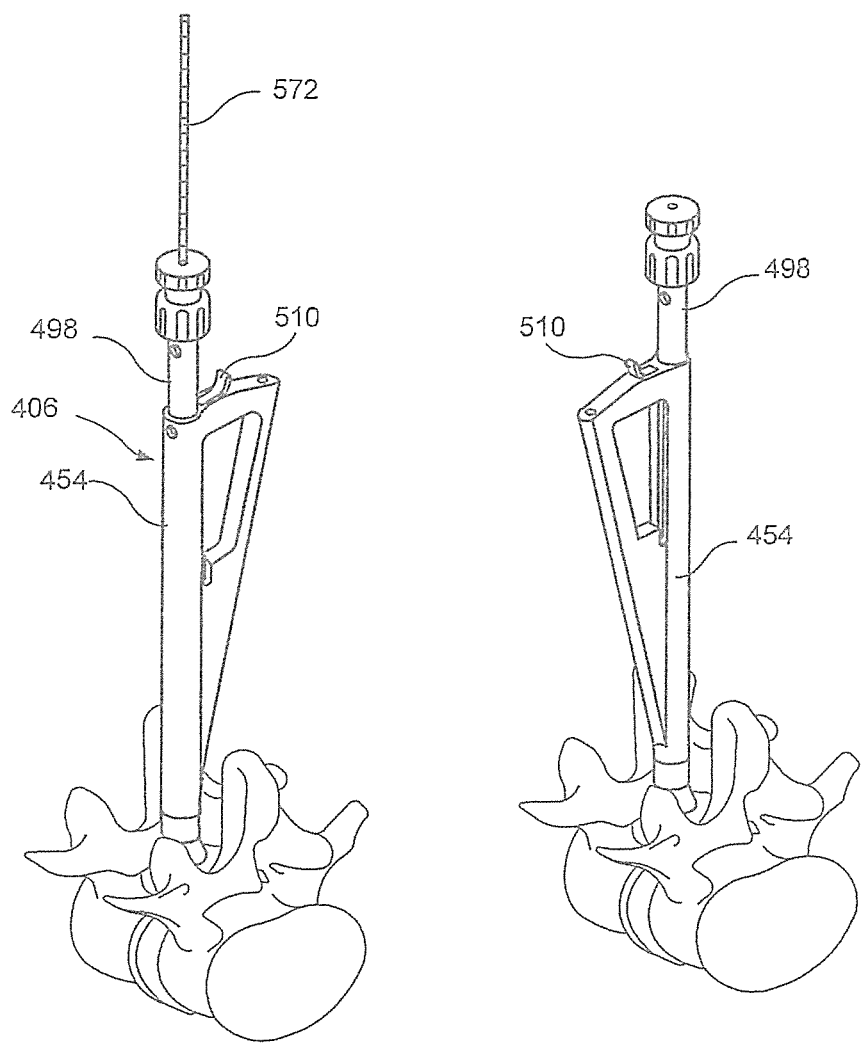
FIG. 41 shows a perspective view of an implant holder inserting an implant into the joint according to the method of FIG. 36.
FIG. 42 shows a perspective view of a body of the implant holder rotated about a shaft thereof according to the method of FIG. 36.

The user may then pack the first and second holes 480, 481 of the implant 402 with bone graft material. Once the holes 480, 481 have been filled with bone graft material, the implant 402 may be coupled to the implant holder 406. In particular, the implant holder 406, in the implant receiving configuration, is positioned over the implant 402 such that the head portion 490 of the implant 402 is received between jaw members 460a, 460b of the shaft 498. As discussed above, the implant holder 406 may be locked in the implant receiving configuration via the locking mechanism 508. Once the implant holder 406 is positioned over the implant 402 as desired, however, the user pulls the release lever 510 of the locking mechanism 508, to slide the body 454 of the implant holder 406 distally over the shaft 498 until the implant holder is locked in the closed configuration and the head portion 490 of the implant 402 is gripped between the jaw members 460a, 460b, as shown in FIG. 41. Using the implant holder 406, the implant 402 is then inserted into the facet joint by sliding the implant holder 406 over the guide wire 507. Upon insertion of the implant 402 into the facet joint, the guide wire may be removed.

As described above, the central channel 472 of the body 454 and the shaft 498 received therein are aligned with the longitudinal axis 4L of the central opening 424 of the implant 402 while the guide channel 474 of the implant holder 406 is aligned with one of the first and second axes 4A, 4B of the first and second openings 410, 412. In situations in which the guide channel 474 is aligned with the first opening 410 (i.e., the locking tab 502 of the locking mechanism 508 engages the first opening 507a of the locking hole 506 in the shaft 498), an awl may be inserted through the guide channel 474 and into the first opening 410 along the first axis 4A to create a hole in the first vertebra of the facet joint. The bone fixation element 408 may then be inserted through the guide channel 474 and into the first opening 410 such that a shaft thereof extends into the hole formed in the first vertebra and a head thereof engages a threading extending along an interior of the first opening 410. The user then pulls the release lever 510 of the lock mechanism 508 to disengage the locking tab 502 from the first opening 507a of the locking hole 506 such that the body 454 of the implant holder 406 may be rotated around the shaft 498, as shown in FIG. 42, until the locking tab 502 engages the second opening 507b of the locking hole 506, aligning the guide channel 474 with the second opening 412 of the implant 402.

Figure 43:
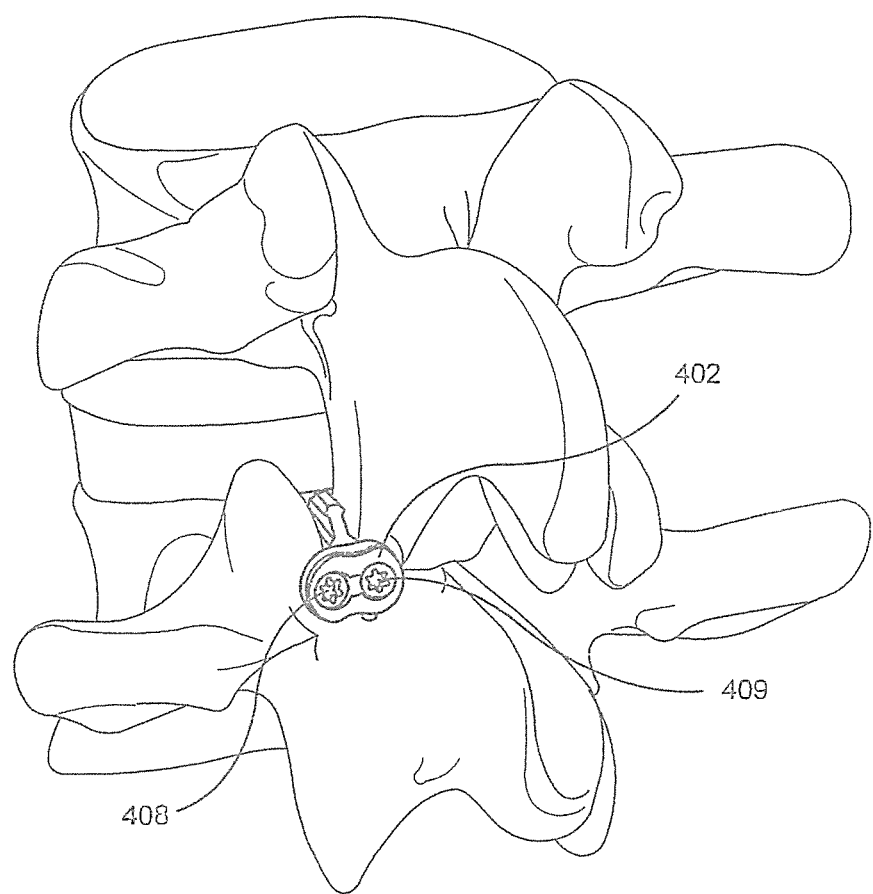

Similarly to the first opening 410, an awl may be used to form a hole in the second vertebra of the facet joint via the guide channel 474 and the second bone fixation element 409 may be inserted therethrough such that a shaft thereof extends into the second vertebra and a head thereof engages a threading extending along an interior of the second opening 412. Although the exemplary embodiment specifically describes a situation in which the guide channel 474 is initially aligned with the first opening 410 of the implant 402, it will be understood by those of skill in the art that the guide channel 474 may initially be aligned with the second opening 412 such that the bone fixation element 409 is inserted through the second opening 412 and into the second vertebra prior to insertion of the bone fixation element 408 through the first opening 410 and the first vertebra. Once the first and second bone fixation elements 408, 409 have been inserted through the first and second openings 410, 412, respectively, the implant holder 406 may be disengaged from the implant 402 and removed from the body, as shown in FIG. 43. The implant holder 406 may be removed by pulling the release lever 510 to move the implant holder to the implant receiving configuration to disengage the implant 402. Alternatively, the implant holder 406 may be disassembled by removing the end cap 516 from the proximal end 512 of the shaft 498 so that the body 454 may be slidably removed from the shaft 498. Once the body 454 has been removed, the jaw members 460a, 460b of the shaft 498 revert to their biased, open configuration such that the implant 402 is released from therebetween. Proper positioning of the implant 402 and the bone fixation elements 408, 409 may be ensured by visually inspecting the implant 402 and/or viewing x-ray images showing the positioning of the implant 402 in the facet joint.

Figure 44:
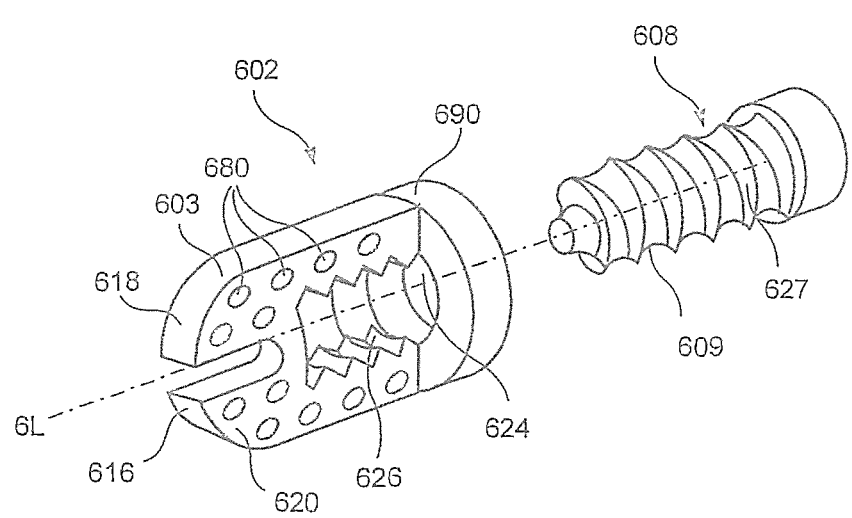
FIG. 44 shows a perspective view of an implant according to another exemplary embodiment of the present invention.
Figures 48, 49:
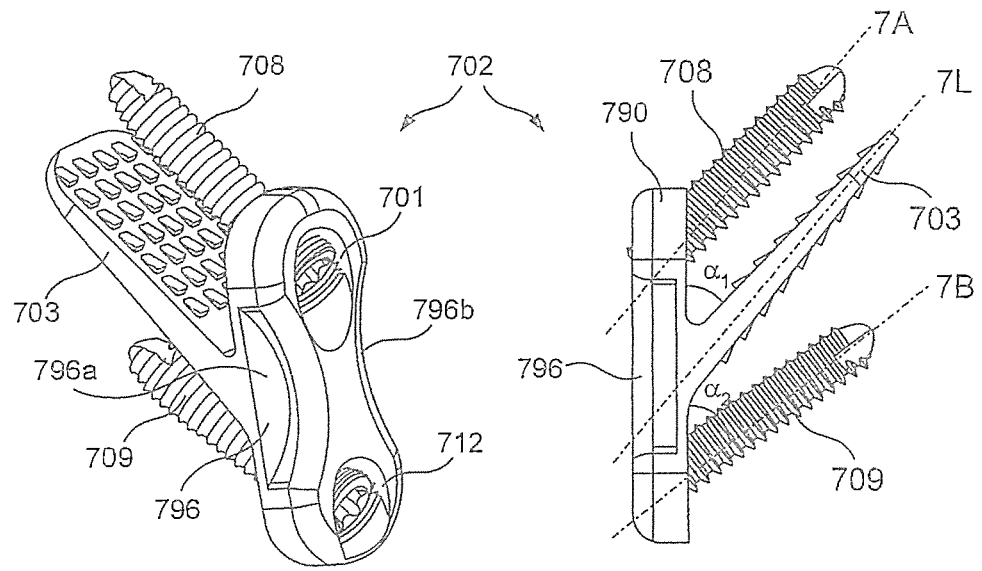
FIG. 48 shows a first perspective view of the implant of FIG. 45 with bone fixation elements inserted therethrough.
FIG. 49 shows a second perspective view of the implant of FIG. 48.
Figures 50, 51:
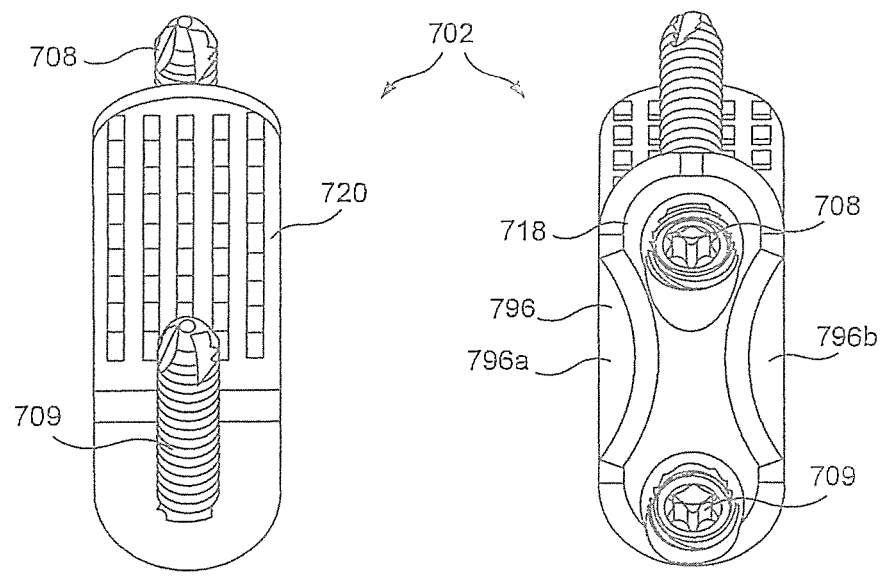
FIG. 50 shows a third perspective view of the implant of FIG. 48.
FIG. 51 shows a fourth perspective view of the implant of FIG. 48.

As shown in FIG. 44, an implant 602 may be substantially similar to the implants 202, 302 and 402, described above, comprising a body 603 extending distally from a head portion 690. The body 603 may be wedge-shaped, similarly to the implant 202. Alternatively, the body 603 may be substantially similar to the bodies 303, 403 including first and second planar surfaces 618, 620 having first portions 618a, 620a substantially parallel to one another and second portions 618b, 620b tapering toward one another to a distal end 616 thereof to facilitate insertion into a facet joint. The implant 602 includes a central opening 624 extending longitudinally through the head portion 690 and the body 603 along a longitudinal axis 6L. The implant 602, however, does not include first and second openings extending therethrough at an angle relative to the longitudinal axis 6L. Rather, a proximal portion of the central opening 624 is sized and shaped to receive a bone fixation element 608 therein. The proximal portion of the central opening 624 may include a threading 626 extending therealong to engage a threading 627 along a shaft 609 of the bone fixation element 608. A diameter of a shaft is larger than a distance between the first and second planar surfaces 618, 620 of the implant 602 such that the proximal portion of the central opening 624 is laterally open to an exterior thereof. Thus, the bone fixation element 608 may be inserted into along the longitudinal axis 6L into the central opening 624 to fix the implant 602 within the facet joint. In particular, the threads 627 along the shaft 609 will engage the surrounding bone to fix the implant 602 therein. Similarly to the head 290, the head 690 is of a larger width and may act as a stop for preventing the head portion 690 from being inserted into the facet joint. Similarly to the holes on the other embodiments that are for promoting bony fusion, for example, holes 180, 480, the body 603 also comprises a plurality of openings 680 extending therethrough from the first surface 618 to the second surface 620.

FIGS. 45-64 depict a system according to another embodiment of the invention including an implant 702 configured for use with an insertion instrument 802. As will be described in greater detail hereinafter, the exemplary system described hereafter is configured for use in cervical spine fixation procedures.

The exemplary implant 702 may be substantially similar to the implants 102, 202, described above. Similarly to the implant 102, the implant 702 has a body 703 extending distally from a head portion 790. The body 703 may be substantially wedge-shaped, tapering from a first end 714 to a second end 716 along a longitudinal axis 7L. The longitudinal axis 7L of the body 703 extends at a non-perpendicular angle from a plane housing the head portion 790. In an exemplary embodiment, an angle a1 between the head portion 790 and the longitudinal axis 7L is approximately 450, although any other angle may be employed without deviating from the scope of the invention. For example, the angle a1 could be any angle between 30° to 90°. The body 703 may further comprise a plurality of ribs 722 projecting from each of first and second surfaces 718, 720 of the body 703 to facilitate engagement with first and second adjoining vertebra. The ribs 722 extend along the surfaces 718, 720 from the first end 714 to the second end 716. The ribs 422 further include teeth 792 or a jagged edge extending therealong to enhance a grip between the implant 702 and the surrounding tissue to prevent the implant 702 from being inadvertently pulled out of a cervical joint into which it has been inserted. As would be understood by those skilled in the art, the teeth 792 are angled with peaks 794 thereof pointing toward the-first end 714 to increase a pull-out resistance of the implant 702. It is noted that although the exemplary embodiment is depicted with five columns of ribs 422, any number and orientation of the ribs 422 may be used without deviating from the scope of the invention. In an exemplary embodiment, a width of the head portion 790 may be approximately 8 mm, a height may be approximately 17.5 mm and a thickness may be approximately 2.2 mm, although any other measurements may be used without deviating from the scope of the invention. Furthermore, the second end 716 of the body 703 may be approximately 0.7 mm in thickness although any other measurement may be used to conform to the requirements of a particular procedure.

The implant 702 further includes first and second openings 710, 712 extending through the head portion 790 to receive bone fixation elements (e.g., bone screws) 708, 709 therethrough.

The first opening 710 extends along a first axis 7A, which is substantially parallel to the longitudinal axis 4L, such that the first bone screw 708 inserted through the first opening 710 extends along the first axis 7A which, when the implant 702 is in a desired position aims the first bone screw 708 along a desired path into a first vertebra of a facet joint. The second opening 712 extends along a second axis 7B angled with respect to the plane housing the body 703 at an angle $\alpha 2$ greater than the angle $\alpha 1$. In an exemplary embodiment, the angle $\alpha 2$ may be approximately 55°, although any other angle may be used without deviating from the scope of the invention. As those skilled in the art will understand, the angular orientation of the longitudinal axes 7A and 7B are selected such that, when the implant 702 is in the desired position, first and second bone screws 708, 709 extend into first and second adjoining vertebrae along desired paths. The head portion 790 of the implant 702 may also include recesses 796 each having a slot 796a, 796b along opposing portions of a periphery thereof for engaging a portion of an implant holder 802, as described in greater detail with respect to earlier embodiments.

FIGS. 52-64 depict an exemplary implant holder 802 used to insert the implant 702 into the facet joint and guide the bone screws 708, 709 into the first and second openings 710, 712, respectively. The implant holder 802 is formed substantially similarly to the implant holder 406 but comprises a handle 804 on a proximal portion thereof to aid in handling and manipulation thereof. The implant holder 802 includes a guide body 806 extending along a longitudinal axis 8L from a proximal end 808 to a distal end 810. The guide body comprises a locking channel 812 extending longitudinally therethrough substantially aligned with the longitudinal axis 8L from a proximal end 814 to a distal end 816, which is proximate to the distal end 810 of the guide body 806. The body 806 further comprises the first screw channel 818 and a second screw channel 824 extending therethrough from respective proximal ends 820, 826 to respective distal ends 822, 828. In an exemplary embodiment, the first screw channel 818 extends at an angle to the longitudinal axis 8L such that a longitudinal axis 8A of the first screw channel 818 intersects a longitudinal axis 8B of the second screw channel 824.

Figure 52:
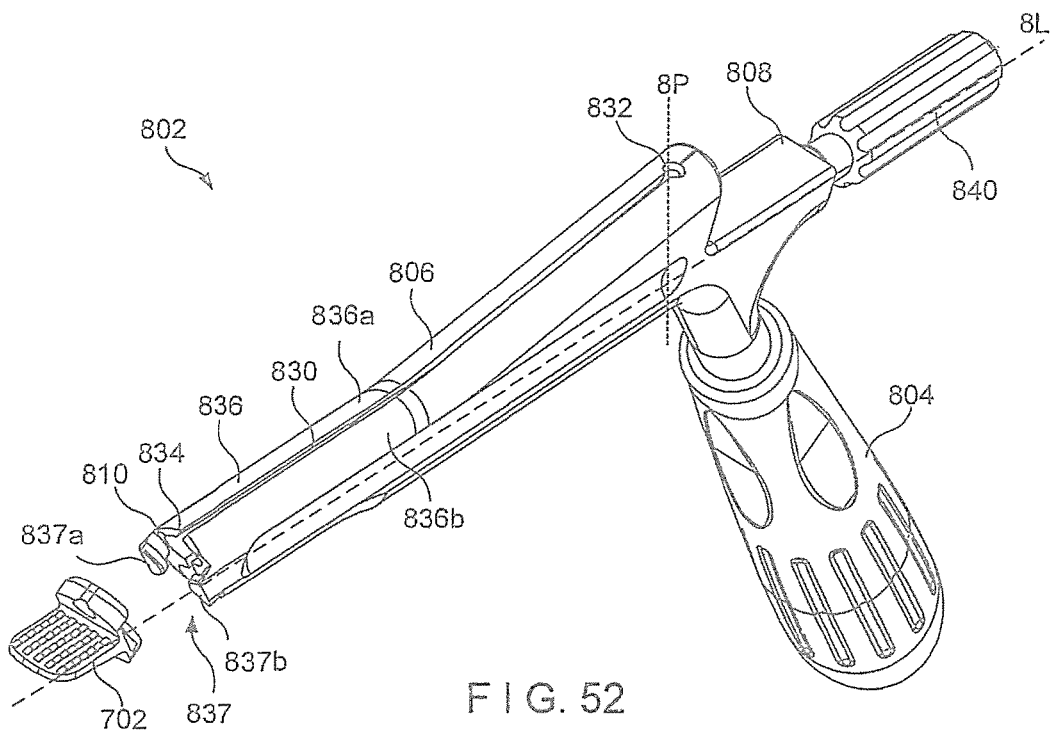
FIG. 52 shows a first perspective view of an insertion instrument used to guide the implant of FIG. 45 to a target position in the body.
Figure 53:
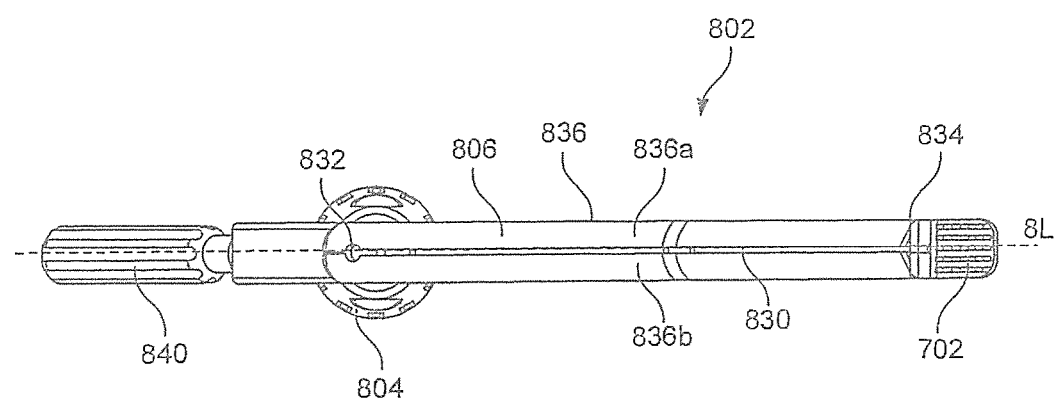
FIG. 53 shows a plan view of the insertion instrument of FIG. 52.

As shown more clearly in FIGS. 52-53, an upper surface of the body 806 comprises a longitudinal slot 830 extending from a proximal end having an increased width portion 832 to a distal end 834 open to the distal end 810 of the body 806. The slot 830 defines compliant arms 836 positioned on either side of the slot 830. First and second compliant arms 836a, 836b are pivotally moveable relative to each other about an axis 8P defined by the increased width portion 832. The first and second compliant arms 836a, 836b combine to form a jaw 837 at the distal end 834. The jaw 837 has a first jaw member 837a and a second jaw member 837b. In an operative configuration, the slot 830 is compressed to move the arms 836a, 836b toward one another and thereby move the jaw members 837a, 837b from a first size and dimension for insertion of the implant 702 into the jaw 837 to a second size and dimension for grasping and holding the implant 702 in the jaw 837.

Figure 54:
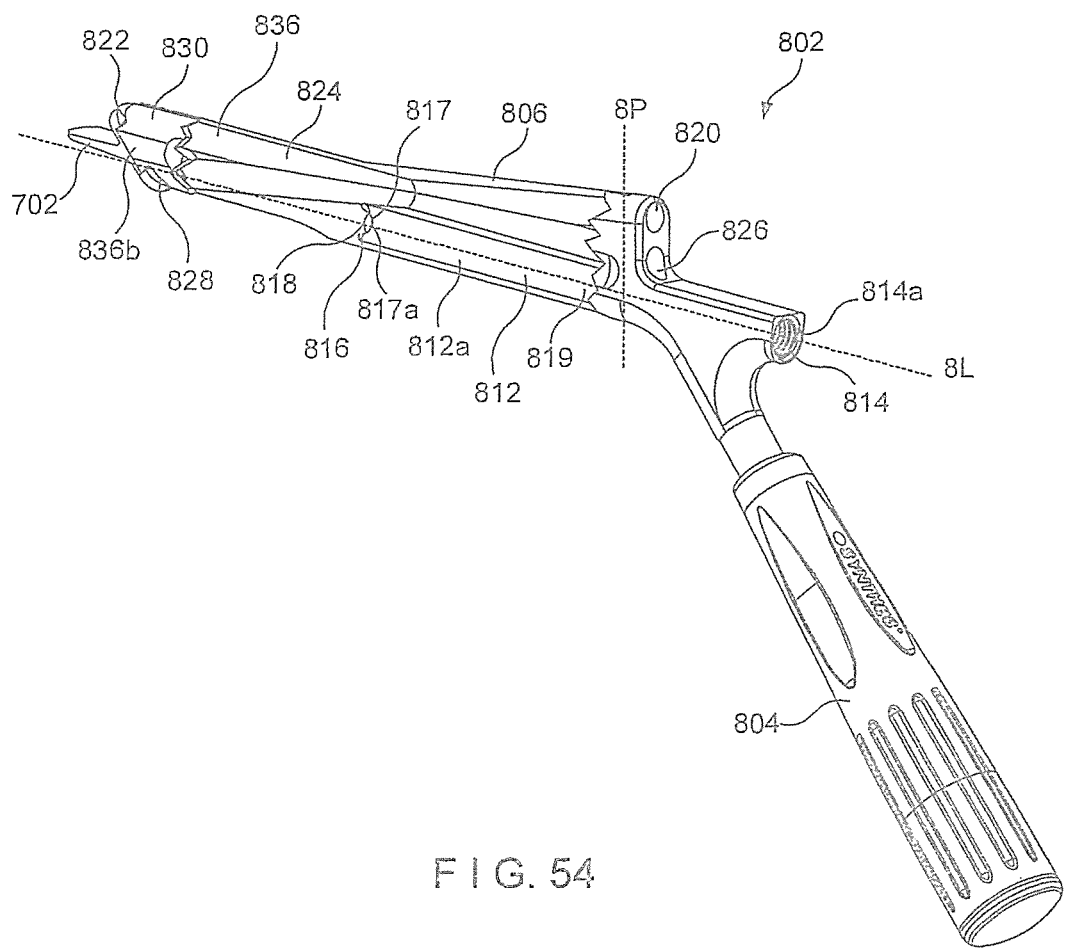
FIG. 54 shows a second perspective view of an insertion instrument of FIG. 52 with a partial cut away section.

The locking channel 812 extends parallel to the second screw channel 824 and parallel to the longitudinal axis 8L. As shown in FIG. 54, the proximal end 814 includes a threaded opening 814a extending into the locking channel 812. The locking channel 812 extends along a longitudinal axis 8L and is substantially cylindrical between the proximal end 814 and the increased width portion 832. From the increased width portion 832 to the distal end 816, the cylindrical shape of the locking channel 812 is divided into first and second channel portions 812a, 812b by the slot 830. The first and second channel portions 812a, 812b are half cylinders formed in the first and second compliant arms 836a, 836b, respectively.

As shown in FIGS. 54-56 and FIG. 59, the distal end 816 of the locking channel 812 has a locking bolt receiver 817 for receiving a locking bolt 840. The locking bolt receiver 817 has a cone-shape that tapers from a side wall 819 in a direction from its widest point at the distal end 816 to a proximally located narrowest point. That is, the locking bolt receiver 817 extends from the side wall 819 defining the locking channel 812 in a direction from the distal end 816 towards the proximal end 814 of the locking channel 812. The locking bolt receiver 817 is divided into first and second portions 817a, 817b by the slot 830. The first portion 817a of the locking bolt receiver 817 is formed in the first compliant arm 836a. The second portion 817b of the locking bolt receiver 817 is formed in the second compliant arm 836b. Planar surfaces 817c, 817d of the first and section portions 817a, 817b, respectively, face each other across the slot 830.

Figures 55, 56, 57:
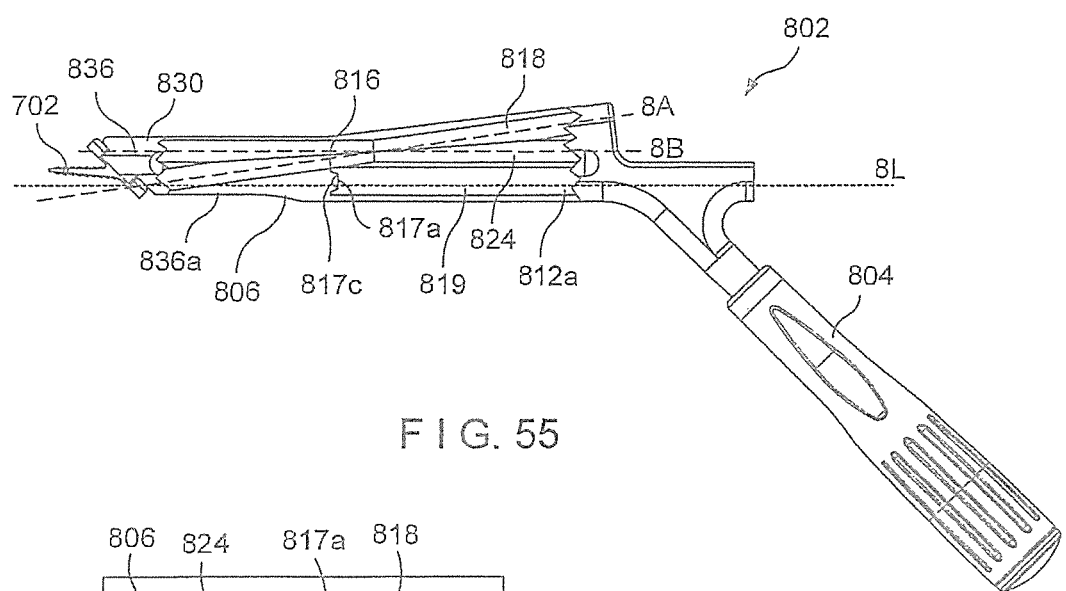
FIG. 55 shows a first partial cross-sectional view of the insertion instrument of FIG. 52.
FIG. 56 shows a first zoomed partial cross-sectional view of the insertion instrument of FIG. 52 in a first operative configuration.
FIG. 57 shows a second zoomed partial cross-sectional view of the insertion instrument of FIG. 52 in the first a second operative configuration.
Figure 58:
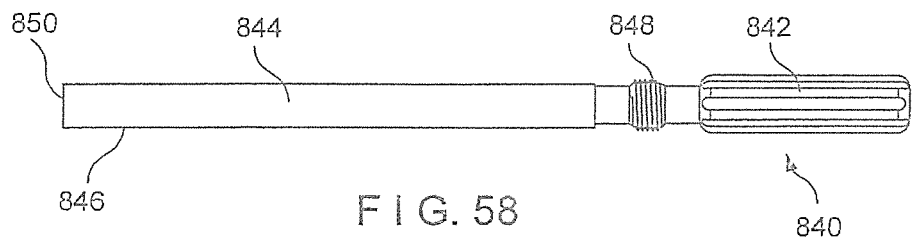
FIG. 58 shows a plan view of a locking bolt for use with the insertion instrument of FIG. 52.

FIGS. 56-60 show the locking bolt 840. The locking bolt 840 has a handle 842 in a proximal region from which a shaft 844 extends to a distal end 846 of the locking bolt 840. The handle 842 is knurled, grooved, etc., for ease of gripping by a user. In a region immediately distal to the handle 842, the shaft narrows and then widens again to a constant diameter section for the remainder of its length. In the narrow section, a threading 848 is formed. The threading 848 is configured to threadedly engage the thread formed in the threaded opening 814a for releasably coupling the locking bolt 840 to the locking channel 812. FIG. 57 shows a cone-shaped recess 850 formed in the distal end 846. The cone-shaped recess 850 is defined by an internal surface shaped to complement the outer surface of the cone-shaped locking bolt receiver 817.

Figure 59:
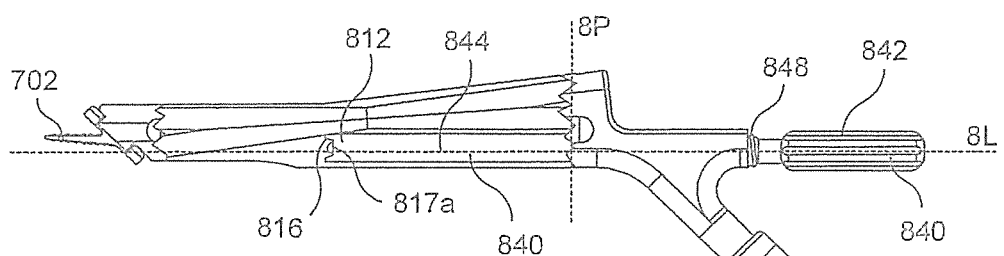
FIG. 59 shows a partial cross-sectional of the insertion instrument of FIG. 52 with the locking bolt of FIG. 58 in a first operative position.
Figure 60:
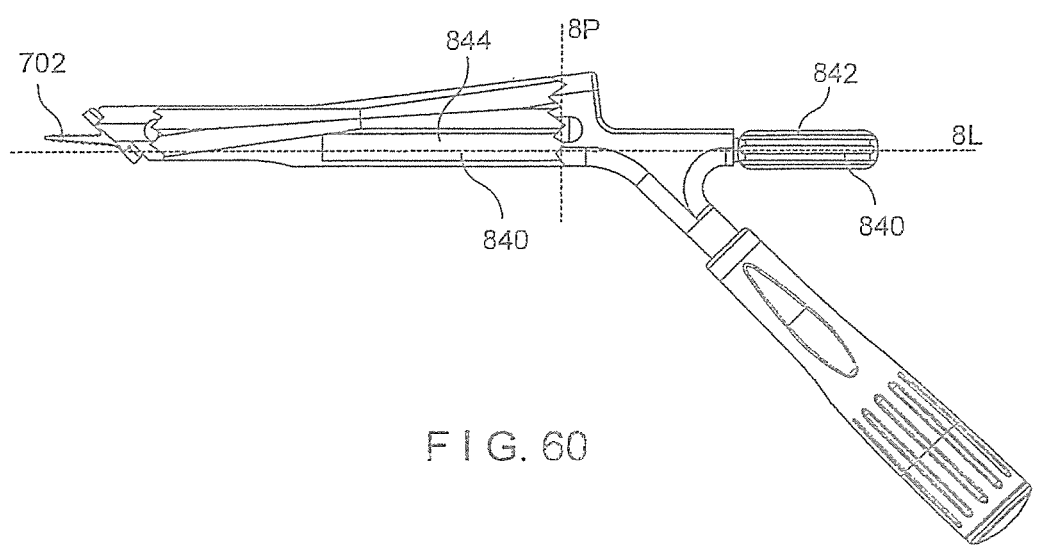
FIG. 60 shows a partial cross-sectional view of the locking bolt of FIG. 58 in a second operative position with the insertion instrument of FIG. 52.

The process by which the implant 702 is locked in the instrument 802 for insertion into a target position will now be described with reference to FIGS. 52 to 60. FIG. 52 shows an implant 702 being aligned with the instrument 802. In FIG. 52 the instrument 802 is in an open configuration. To fix the implant 702 in the instrument 802, the jaw 837 is first engaged with the recesses 796. Due to compliant nature of the arms 836a, 836b and the distance between the jaw members 837a, 837b, the jaw members 837a, 837b partially engage with the slots 796a, 796b to temporarily hold the implant 702 in the instrument. FIGS. 56 to 60 show how the locking bolt 840 is engaged with the locking bolt receiver 817 to transition the instrument 802 from the open configuration to the locked or gripping configuration in which the implant 702 is firmly held by the instrument 802 by the jaw 837. The locking bolt 840 is positioned through the locking channel 812 by inserting the shaft 844 into the threaded opening 814a and pushing the handle 842 until the threading 848 abuts the threaded opening 814a. The handle 842 is then rotated to engage the threading 848 with the thread of the threaded opening 814a. After a couple of rotations of the handle 842, the distal end 846 of shaft 844 has advanced towards the distal end 816 and locking bolt receiver 817 of the locking channel 812. FIGS. 56, 57 and 59 show the distal end 846 shortly before it engages with the locking bolt receiver 817. As shown by FIG. 60, the handle 842 continues to be rotated by a user until a point is reached where it can no longer be rotated, indicating that the implant 702 is firmly held. At this point, the inner cone 850 has engaged and slid over the outer cone of the locking bolt receiver 817 causing the distance between the planar surfaces 817c, 817d of the portions 817a, 817b to decrease. Since the portions 817a and 817b are part of the compliant arms 836a and 836b, this has the effect of narrowing the slot 830 and thereby reducing the distance between the jaw members 837a, 837b. As a consequence the jaw members 837a, 837b have been moved to a holding configuration where they have become firmly engaged in their respective slots 796a, 796b to firmly grip the implant 702 for guiding the implant 702 into a target position. As described in greater detail with respect to earlier embodiments, the implant 702 is secured to the insertion instrument 802 prior to insertion thereof into the body.

Figure 61:
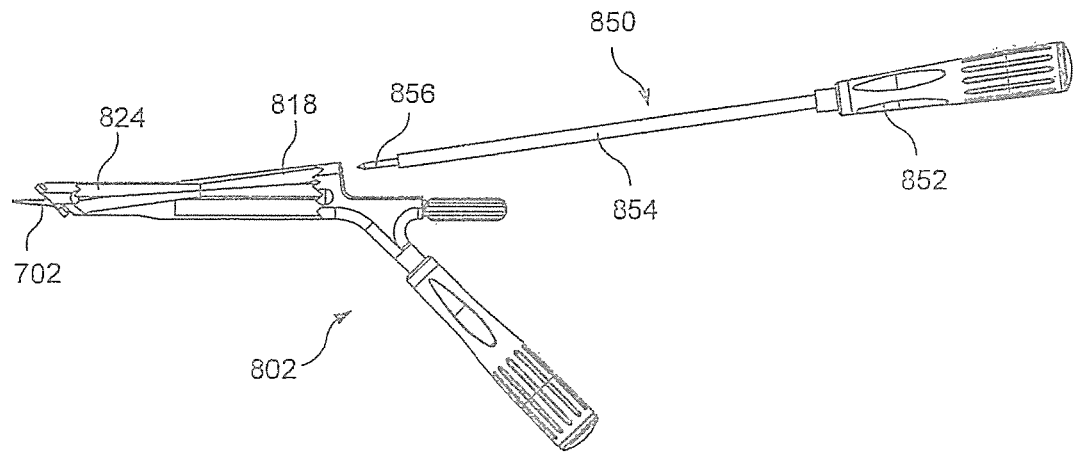
FIG. 61 shows an awl for use with the insertion instrument of FIG. 52 in a first operative position.
Figure 62:
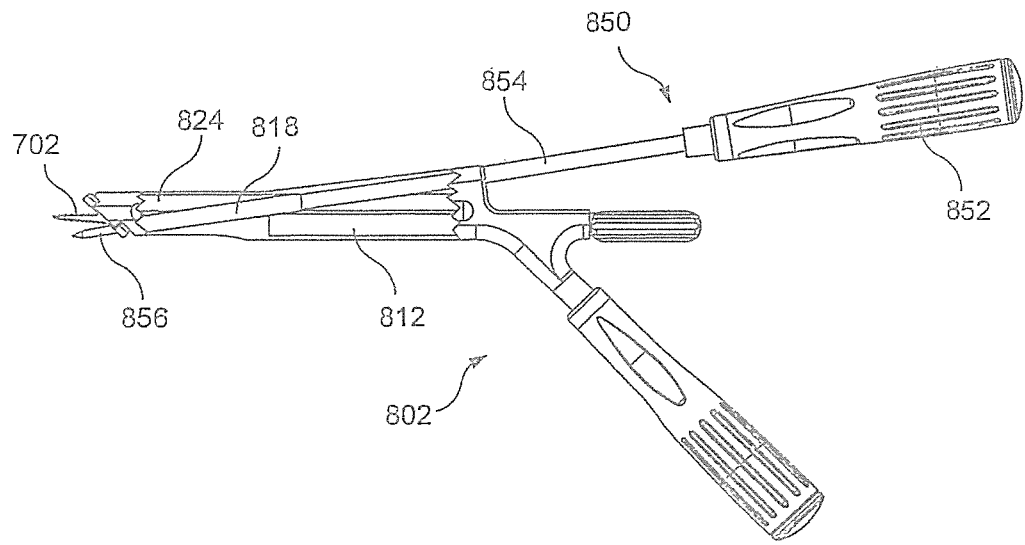
FIG. 62 shows the awl of FIG. 61 in a second operative position.

The insertion instrument 802 and implant 702 are guided to a target position adjacent target cervical vertebrae. As shown in FIGS. 61-62, an awl 850 known in the art is then inserted through each of the first and second channels 818, 824 and through each of the first and second openings 710, 712 to break the bone cortex and prepare the bone hole for the bone screws 708, 709. Specifically, as those skilled in the art will understand, the awl 850 extends from a proximal end comprising a handle 852 and along a shaft 854 to a sharpened portion 856 at a distal end, wherein a diameter of the shaft 854 substantially conforms to a diameter of the first and second channels 818, 824 and a diameter of the sharpened portion 856 substantially conforms to dimensions of the first and second bone screws 708, 709.

Figure 63:
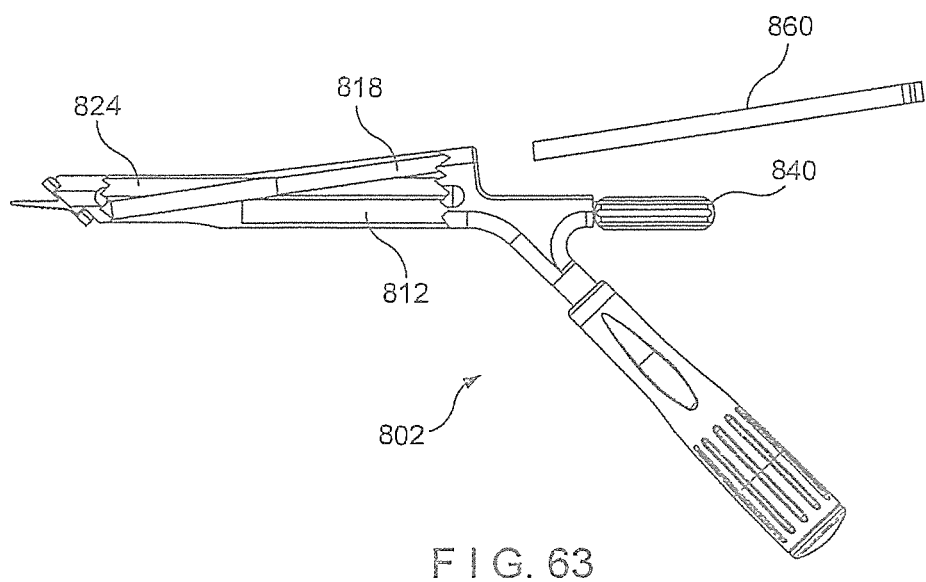
FIG. 63 shows a guide sleeve for use with the insertion instrument of FIG. 52 in a first operative position.
Figure 64:
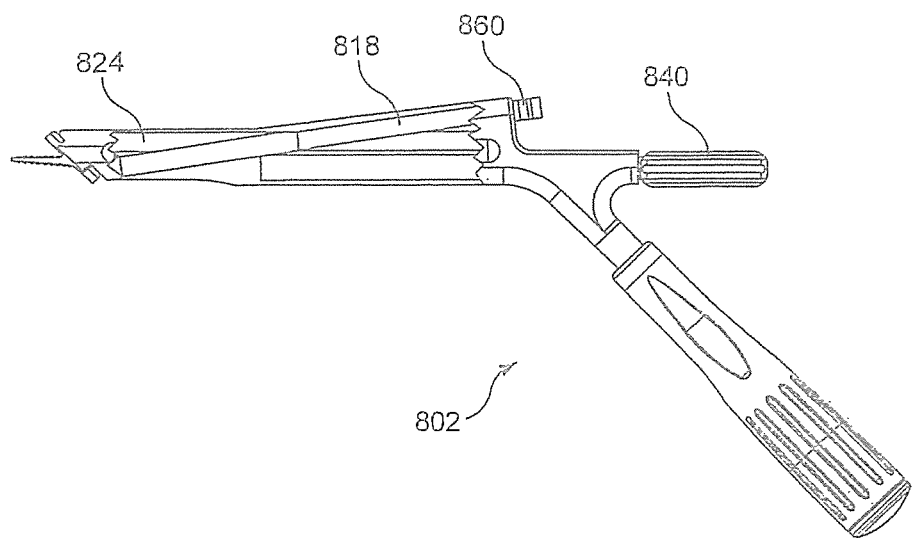
FIG. 64 shows the guide sleeve of FIG. 63 in a second operative position.
Figure 66:
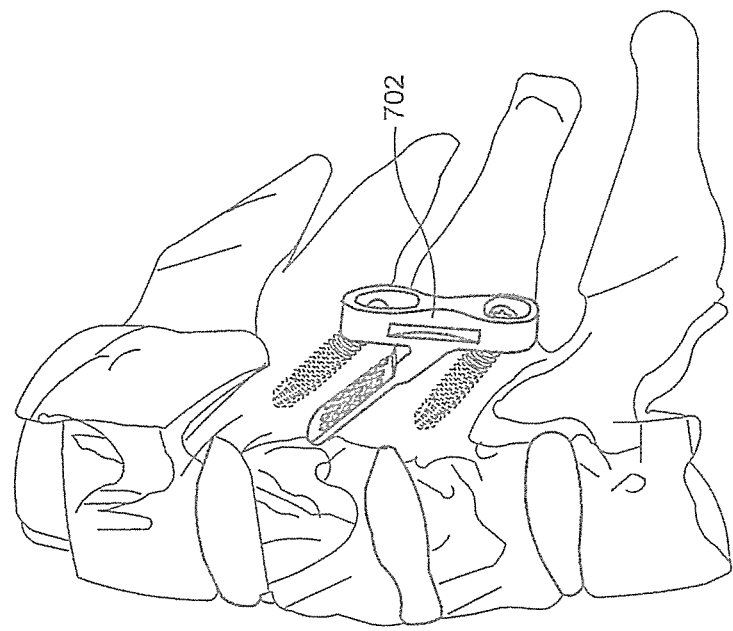
FIG. 66 shows a side view of the 3D computer model of FIG. 65.
Figure 65:
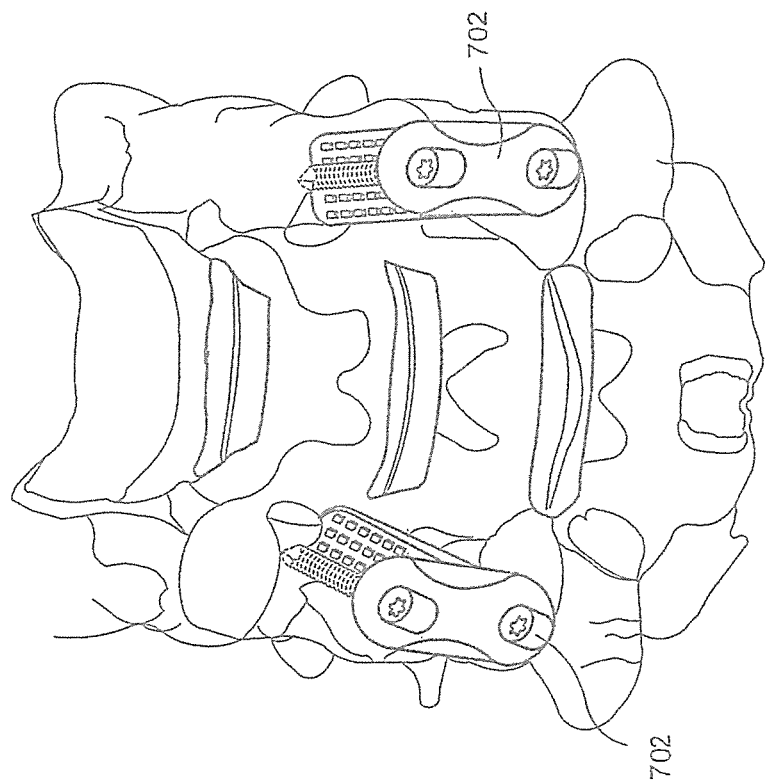
FIG. 65 shows a perspective view of a 3D computer model illustrating a portion of a cervical spine with first and second implants of FIG. 45 in situ.

As shown in FIGS. 63-64, a guide sleeve 860 is inserted into the first channel 818 to bridge an area where the first and second channels 818, 824 intersect. The guide sleeve 860 eliminates the risk of a bone screw inserted through the first channel 818 irretrievably falling off a screwdriver into the second channel 824 and vice versa. In accordance with an exemplary method according to the invention, the guide sleeve 860 is inserted into the first channel 818 to guide the insertion of the second bone screw 709 through the second opening 712 of the implant 702. Once the second bone screw 709 has been inserted, the guide sleeve 860 is removed and inserted into the second channel 824 to guide insertion of the first bone screw 708 into the first opening 710 of the implant 702. The first and second bone screws 708, 709 are then inserted into the implant 702 using a driving mechanism (not shown) known in the art. Once the first and second bone screws 708, 709 have been inserted to their respective target positions, the locking bolt 840 is unscrewed from the locking channel 812 and withdrawn proximally. The locking channel 812 returns to its original configuration due to the compliant nature of the arms 836a, 836b and thereby the slot 830 expands and the jaw transitions to the open configuration in which the implant 702 is loosely held. The implant 702 is then released and the insertion instrument 802 removed from the body leaving the implant 702 in position in the cervical spine as shown by FIGS. 65 and 66.

Figure 67:
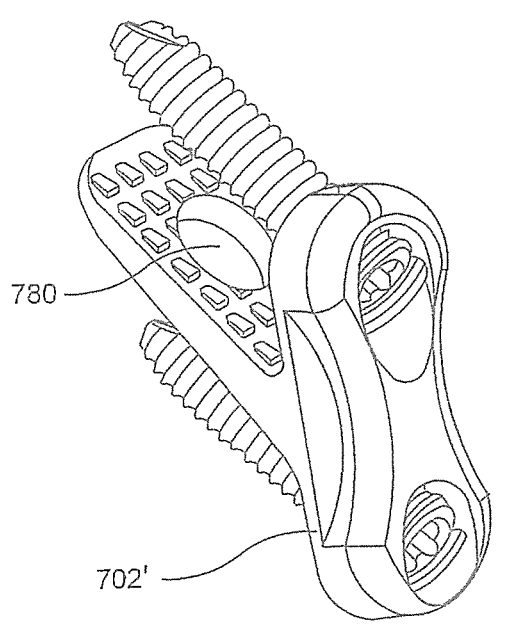
FIG. 67 shows a perspective view of an implant according to a still further exemplary embodiment of the invention.
Figure 68:
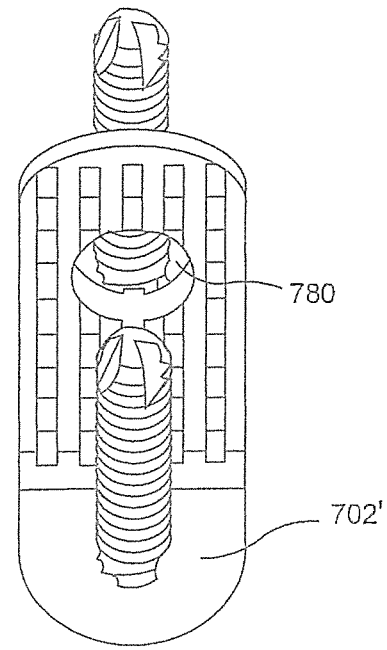
FIG. 68 shows a front view of the implant of FIG. 67.
Figure 69:
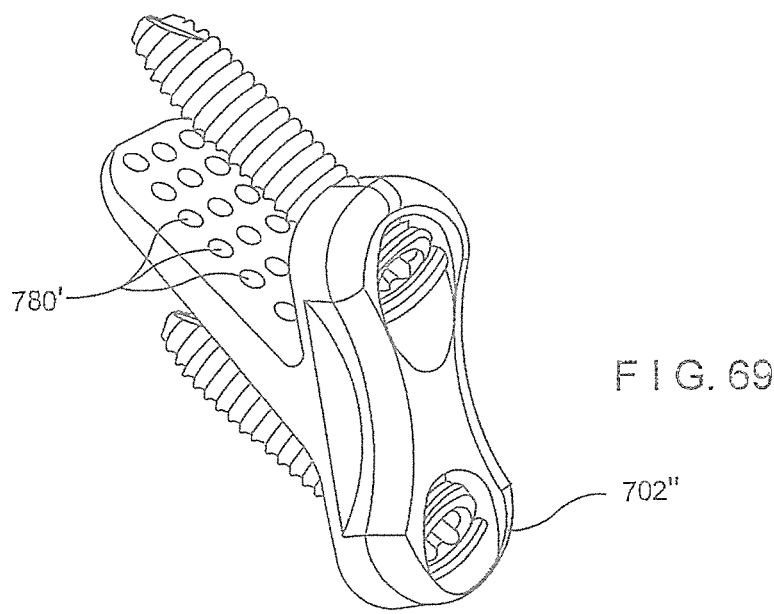
FIG. 69 shows a perspective view of an implant according to a yet still further exemplary embodiment of the invention.

FIGS. 67 and 68 show a further embodiment of the invention including an implant 702'. The implant 702' is substantially the same as the implant 702 with the exception of a hole 780 formed therein. FIG. 69 shows a still further embodiment of the invention including an implant 702", the implant features a plurality of holes 780' formed therein. FIG. 69 shows the implant 702" without the friction enhancing elements 792 of the implant 702, which can of course be provided as one of skill in the art would understand. As described in greater detail with respect to earlier embodiments, the hole 780 and plurality of holes 780' have the same purpose and function as the holes 480, 481.

Figure 70:
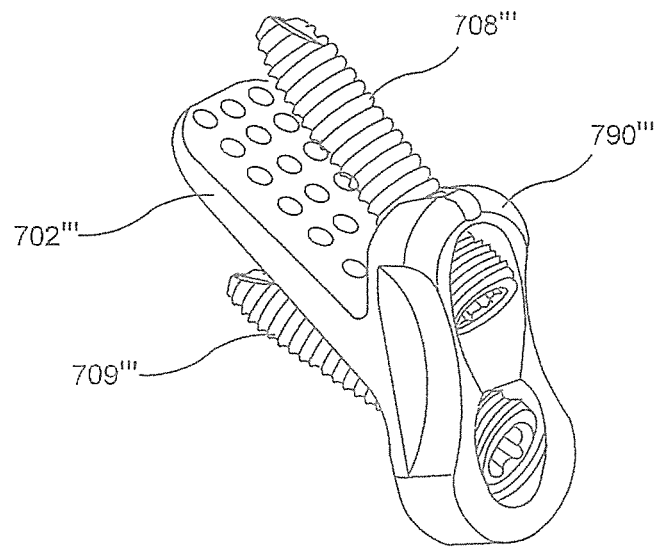
FIG. 70 shows a perspective view of an implant according to yet still another exemplary embodiment of the invention.
Figure 71:
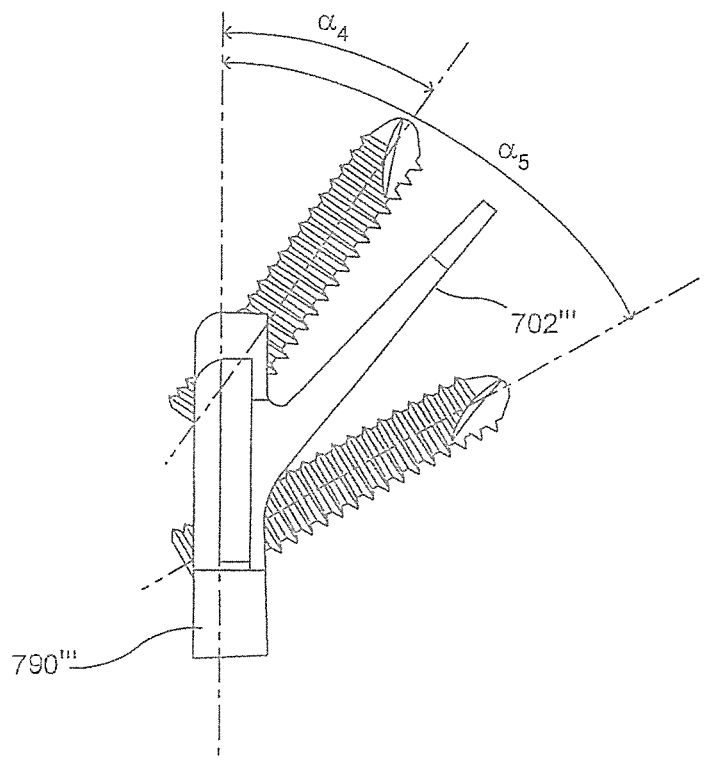
FIG. 71 shows a side view of the implant of FIG. 70.

FIGS. 70 and 71 show yet another embodiment of the invention including an implant 702". The implant 702" is substantially the same as the implants 702, 702', 702" with the exception that a head portion 790" thereof is smaller in comparison to the head section 790 described for the implant 702. As a consequence of the smaller head portion 790", screw holes of the implant 702" are angled such that screws 708", 709" inserted therethrough enter into the respective parts of the facet joints. With respect to the head portion 790", the first screw 708" is angled at α4 and the second screw 709" is angled at α5 relative to the head portion 790". The angle α4 has a range of 20° to 90° and the angle as has a range of 40° to 120°.

Figure 72A:
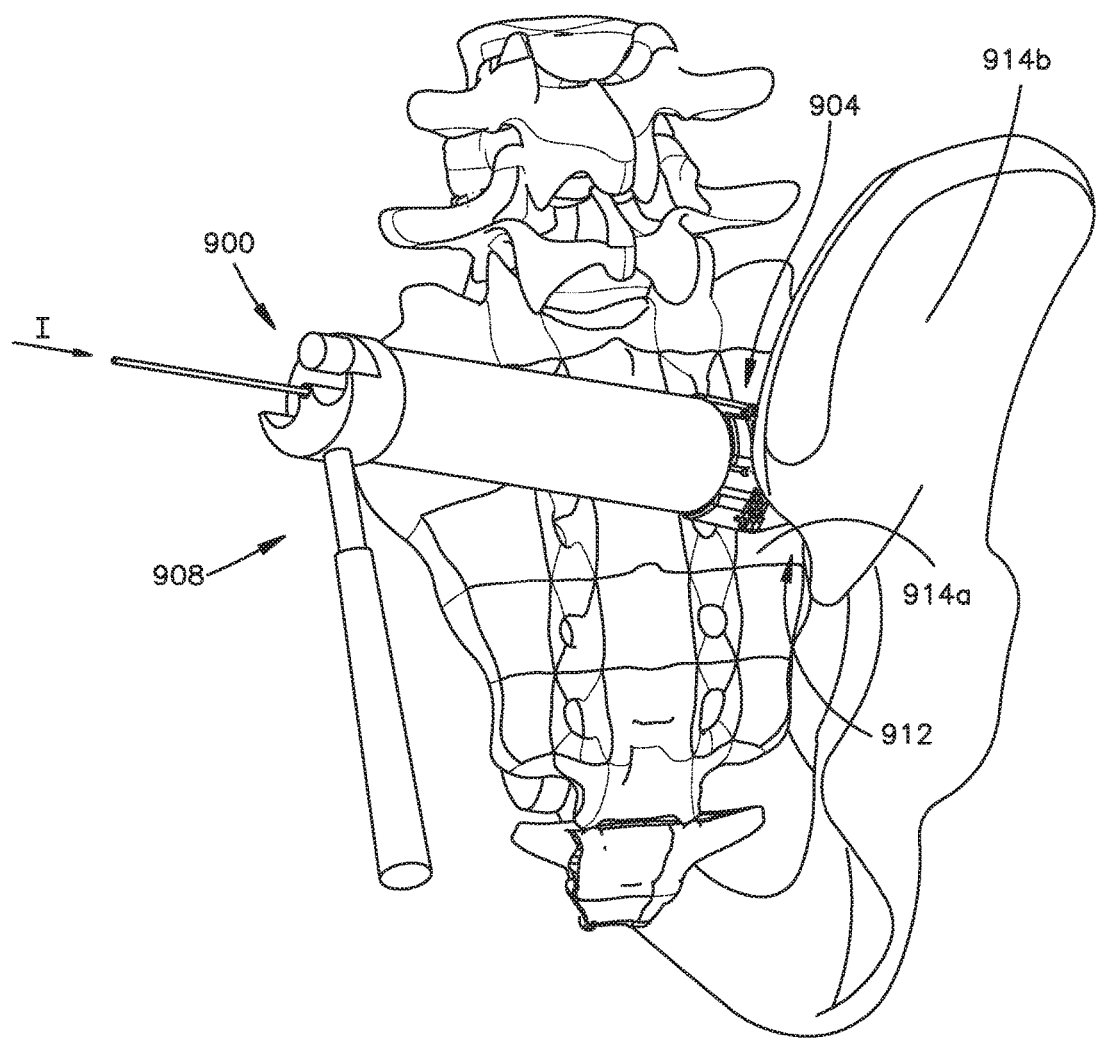
FIG. 72A is a perspective view of an implant system in accordance with another embodiment, the implant system including an insertion instrument and an interbody implant that is configured to be inserted into a sacro-iliac joint.

Now referring to FIGS. 72A and 72B, an implant system 900 includes an interbody implant 904 and an insertion instrument 908 coupled to the interbody implant and configured to insert the interbody implant into a sacro-iliac joint 912 defined between a first bone such as the sacral bone 914a and a second bone such as the iliac bone 914b. As shown in FIG. 72A, the interbody implant 904 is configured to be inserted into the sacro-iliac joint along an insertion direction I. As shown in FIG. 72B, the interbody implant 904 can be coupled to the insertion instrument 908 using a form fit connection to thereby prevent the interbody implant 904 from inadvertently disengaging from the insertion instrument 908. While the implant 904 is described as being configured to be inserted into a sacro-iliac joint it should be appreciated that the implant 904 can be sized and configured to be inserted into any joint or interbody space, as desired. Further, it should be appreciated, that the insertion instrument 908 can be configured to couple to any type of implant and is not limited to the implant 904.

As shown in FIGS. 73A-73F, the interbody implant 904 can be substantially wedge shaped and can include an implant body 916 having a proximal end 920 and a distal end 924 spaced from the proximal end 920 along the insertion direction I. The implant 904 can further include a head portion 928 that extends from the proximal end 920 of the implant body 916 along a proximal direction that is opposite the insertion direction I. The implant body 916 can be sized and configured to be inserted into the sacro-iliac joint 912 and the head portion 928 can be configured to receive at least one such as two bone fixation elements to thereby fix the implant 904 within the sacro-iliac joint 912. It should be appreciated, however, that the implant 904 can be configured to be inserted into any joint defined between any two bones.

Figure 73A:
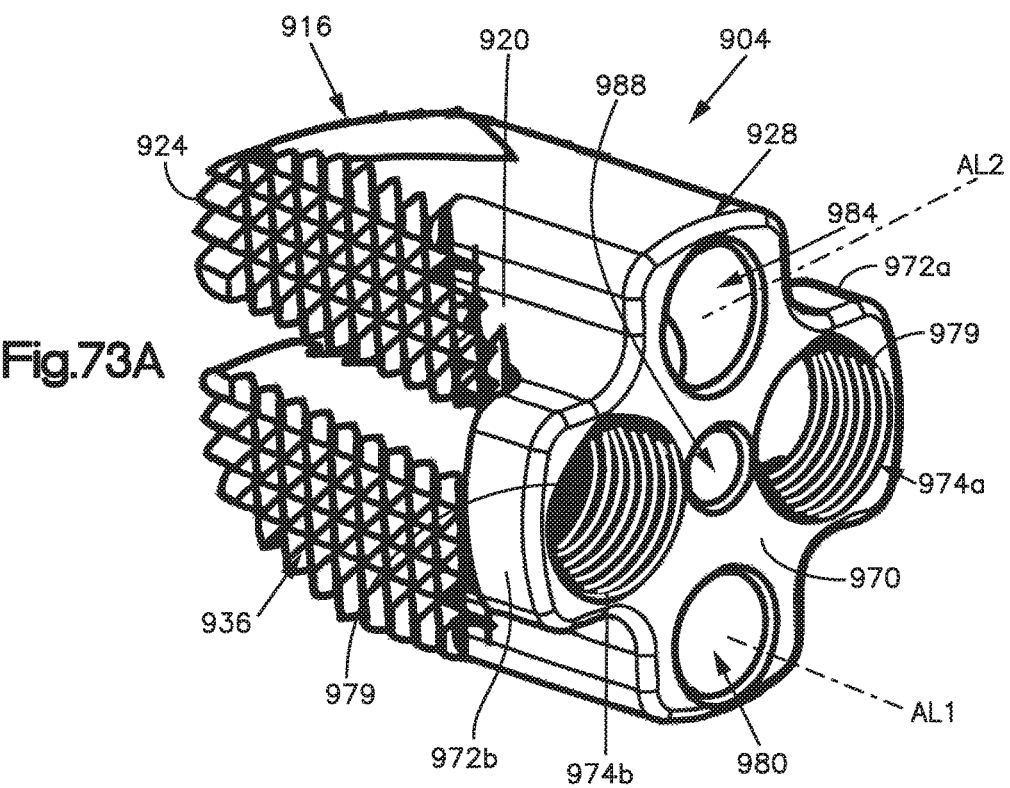
FIG. 73A is a front perspective view of the interbody implant shown in FIG. 72B, the interbody implant including a wedge shaped implant body having a distal end and a proximal end, and a head portion that extends from the proximal end of the implant body.
Figure 73B:
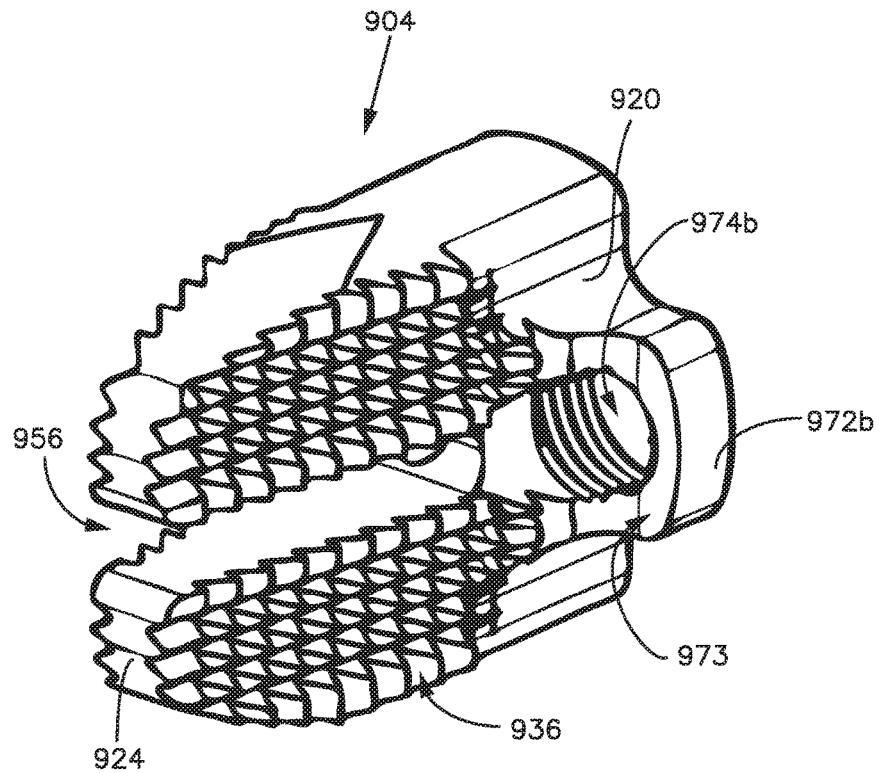
FIG. 73B is a rear perspective view of the interbody implant shown in FIG. 73A.
Figure 73C:
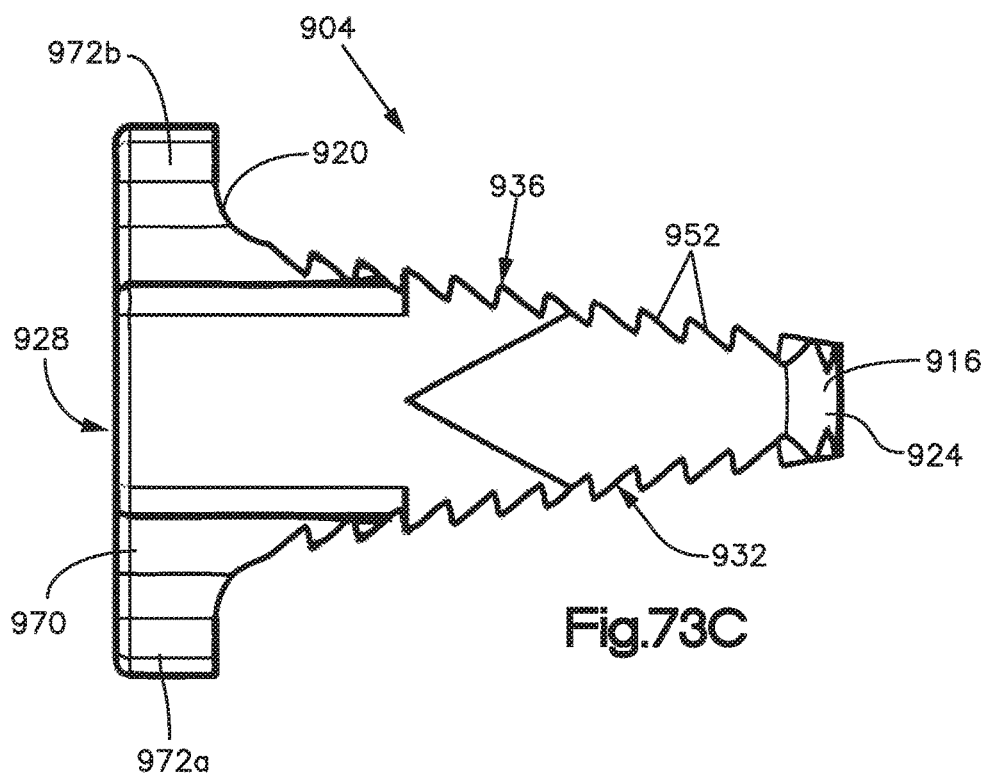
FIG. 73C is a top plan view of the interbody implant shown in FIG. 73A.
Figure 73D:
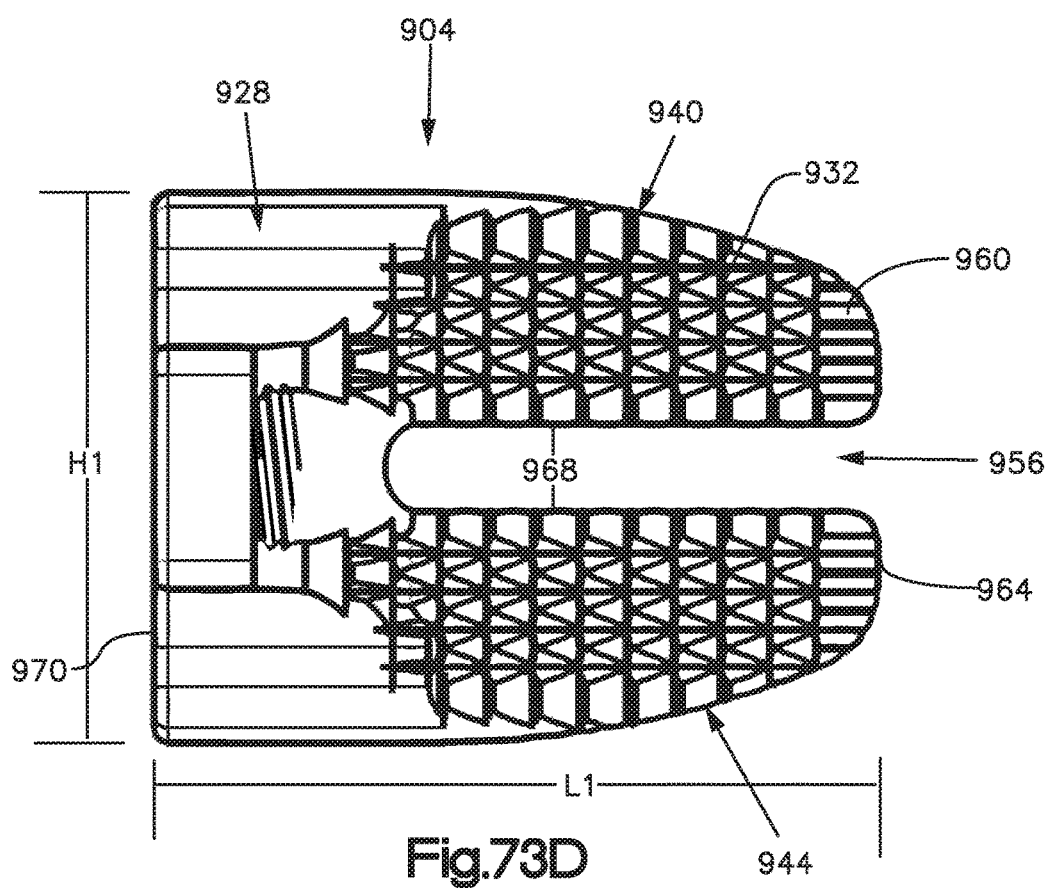
FIG. 73D is a side elevation view of the interbody implant shown in FIG. 73A.

As shown in FIG. 73A-73E, the implant body 916 defines a first bone or iliac engagement surface 932 and a second bone or sacral engagement surface 936 that are each substantially planar and extend from the proximal end 920 to the distal end 924 of the implant body 916. The iliac engagement surface 932 can be sized and configured to abut the iliac bone 914b when the implant 904 is inserted into the sacro-iliac joint 912, and the sacral engagement surface 936 can be sized and configured to abut the sacral bone 914a when the implant 904 is inserted into the sacro-iliac joint 912. The implant body 916 can further include third and fourth side surfaces 940 and 944 that connect the iliac and sacral engagement surfaces 932 and 936. As shown in FIG. 73D, the third and fourth side surfaces 940 and 944 taper as they extend along the insertion direction. It should be appreciated, however, that the third and fourth surfaces 940 and 944 can be parallel along the entire length of the implant body 916, as desired.

As shown in FIG. 73C, at least one of the iliac engagement surface 932 and the sacral engagement surface 936 converges toward the other of the iliac engagement surface 932 and the sacral engagement surface 936 as it extend along a direction from the proximal end 920 to the distal end 924 (such as the insertion direction I). In the illustrated embodiment, both the iliac engagement surface 932 and the sacral engagement surface 936 converge toward each other as they extend from the proximal end 920 to the distal end 924. That is, the iliac engagement surface 932 and the sacral engagement surface 936 extend from the proximal end 920 to the distal end 924 at an angle with respect to the longitudinal axis to define a tapered wedge-shape. It should be appreciated that while in the illustrated embodiment the entire iliac engagement surface 932 and the entire sacral engagement surface 936 converges toward the other, in some embodiments, only a portion of the iliac engagement surface 932 and/or the sacral engagement surface 936 can converge toward the other, if desired. Further, it should be appreciated that in some embodiments, the sacral engagement surface 936 and iliac engagement surface 932 can be parallel to each other, as desired.

Figure 73E:
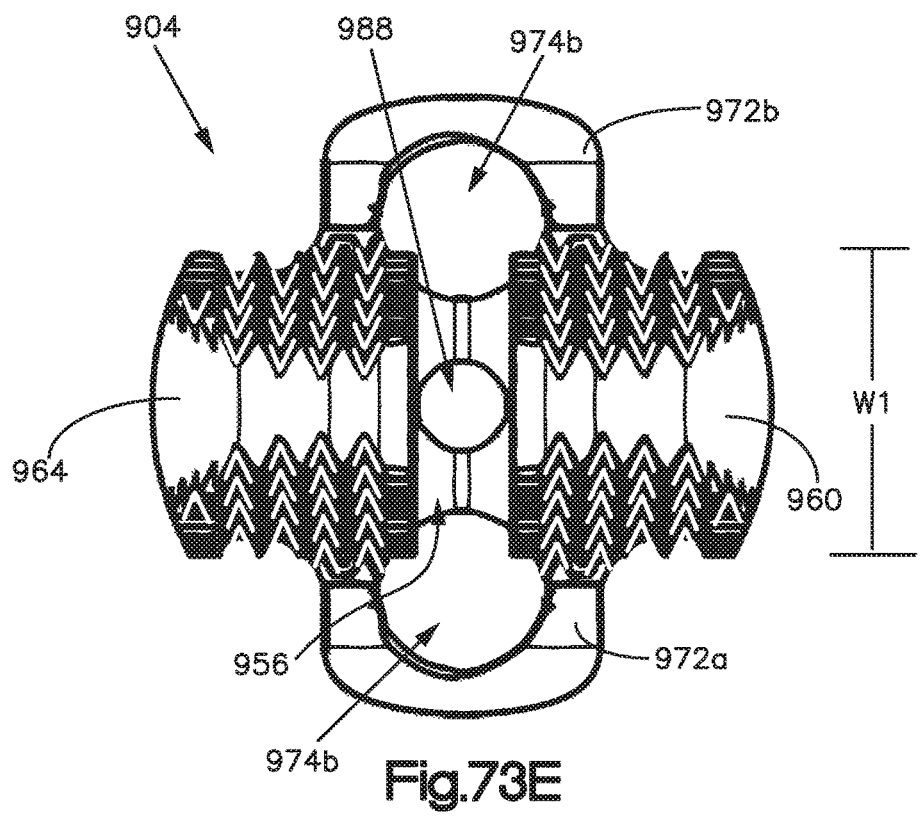
FIG. 73E is a rear elevation view of the interbody implant shown in FIG. 73A, the head portion and the implant body each having a guide wire receiving channel that are configured to receive a guide wire.

As shown in FIGS. 73C-73E, the implant body 916 can define a first width $W_1$ such as a maximum width that is measured at the proximal end 920 that is between about 7 mm and about 14 mm and is preferably about 10 mm. The implant body 916 can define a second width $W_2$ measured at the distal end 924 that is between about 1.5 mm and about 4.5 mm and is preferably about 2.5 mm. The implant body 916 can have a length $L_1$ measured from the proximal end 920 to the distal end 924 that is between about 18 mm and about 30 mm and is preferably about 22 mm, and can have a maximum height $H_1$ measured from the third side surface 940 to the fourth side surface 944 that is between about 15 mm and about 25 mm and is preferably about 19 mm. It should be appreciated, however, that the implant body can have any dimensions as desired.

Figure 78:
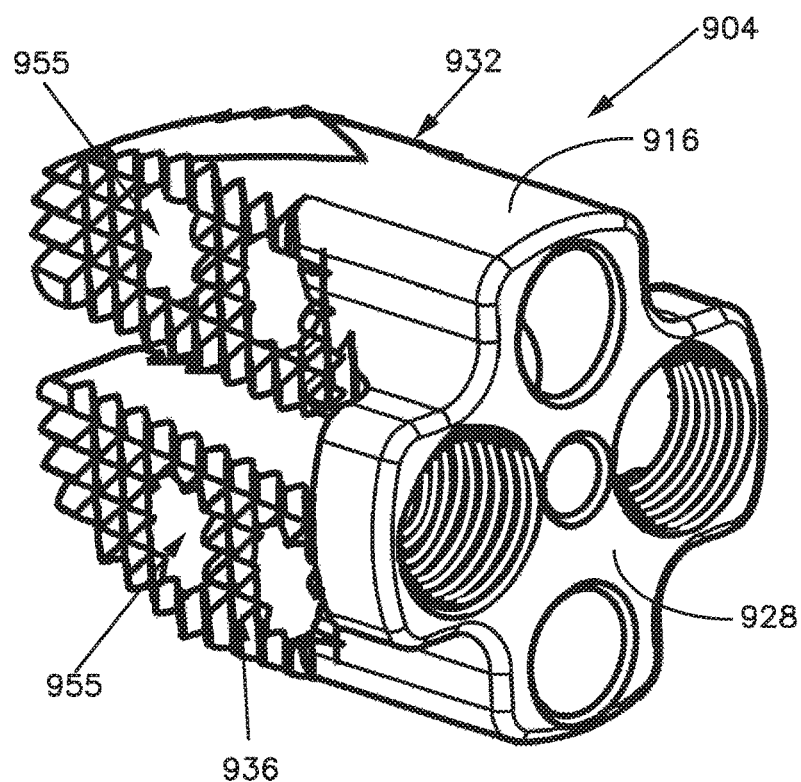
FIG. 78 is a front perspective view of the interbody implant shown in FIG. 73A including an implant body having a plurality of bony-ingrowth channels.

As shown in FIG. 73C, the iliac and sacral engagement surfaces 932 and 936 can include a plurality of teeth 952 that are configured to engage the iliac and sacral bones 914a and 914b when the implant 904 is inserted into the joint 912 so as to prevent migration of the implant 904. Further, the iliac and sacral engagement surfaces 932 and 936 can be roughened and/or treated with a coating to facilitate boney ingrowth. The implant 904 can also include a plurality of boney in-growth channels that extend through the implant body 916 from the iliac engagement surface 932 to the sacral engagement surface 920, such as boney in-growth channels 955 shown in FIG. 78 to promote bony growth therethrough, increasing stability after fusion.

As shown in FIGS. 73D and 73E, the implant body 916 can further include a guide wire receiving channel 956 that extends therethrough along the insertion direction I from the proximal end 920 to the distal end 924 such that the guide wire channel of the head portion is coaxial with the guide wire channel 956 of the implant body 916. The guide wire channel 956 can be configured to receive a guide wire such as a K-wire, or any other like device as desired so as to guide the implant 904 toward the sacro-iliac joint 912. In the illustrated embodiment, the implant body 916 includes a first body portion 960 and a second body portion 964 that is separated from the first body portion 960 along a direction that is perpendicular to the insertion direction I such that a gap 968 is defined between the first and second body portions 960 and 964 along at least a portion such as along the entire length of the implant body 916 from the proximal end 920 to the distal end 924. As shown in FIG. 73D, the gap 968 defines the guide wire channel 956 of the implant body 916. It should be appreciated, however, that the implant body 916 can be configured as a single body portion having a guide wire channel extending through the single body portion.

With continued reference to FIGS. 73A-73H, the head portion 928 extends from the proximal end 920 of the implant body 916 along the proximal direction and includes a head body 970 having a width $W_3$ measured along a direction that is perpendicular to the insertion direction that is greater than that of the proximal end 920 of the implant body 916 such that the head body 970 defines a first projection 972a that extends beyond the iliac engagement surface 932 and a second projection 972b that extends beyond the sacral engagement surface 936. That is the width $W_3$ is greater than the width $W_1$ of the implant body 916. Both the first and second projections 972a and 972b define abutment surfaces 973 that can provide surfaces that abut outer surfaces of the iliac and sacral bones 914a and 914b to thereby act as a stop so as to prevent the head portion 928 from being inserted into the sacro-iliac joint 912. In the illustrated embodiment, the head portion 928 defines a cross-shape, though it should be appreciated that the head portion can define any shape as desired. Further, it should be appreciated, that the head portion 928 can be configured so as to be void of the abutment surfaces 973, as desired. The head portion 928 can further define a length $L_2$ that is between about 2 mm and about 6 mm and is preferably about 3.5 mm. It should be appreciate, however, that the head portion can have any length as desired.

Figure 73F:
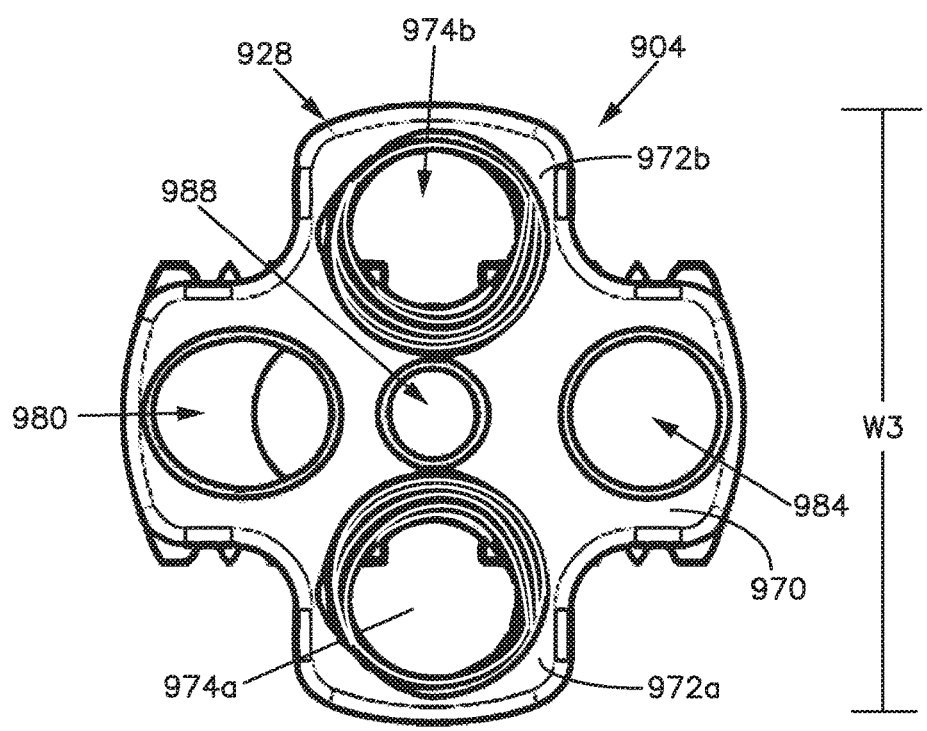
FIG. 73F is a front plan view of the interbody implant shown in FIG. 73A, the head portion of the implant body including first and second bone fixation receiving channels and first and second locking channels, the first locking channel defining a first locking central axis, and the second locking channel defining a second locking central axis that is angular offset with respect to the first locking central axis.
Figure 73G:
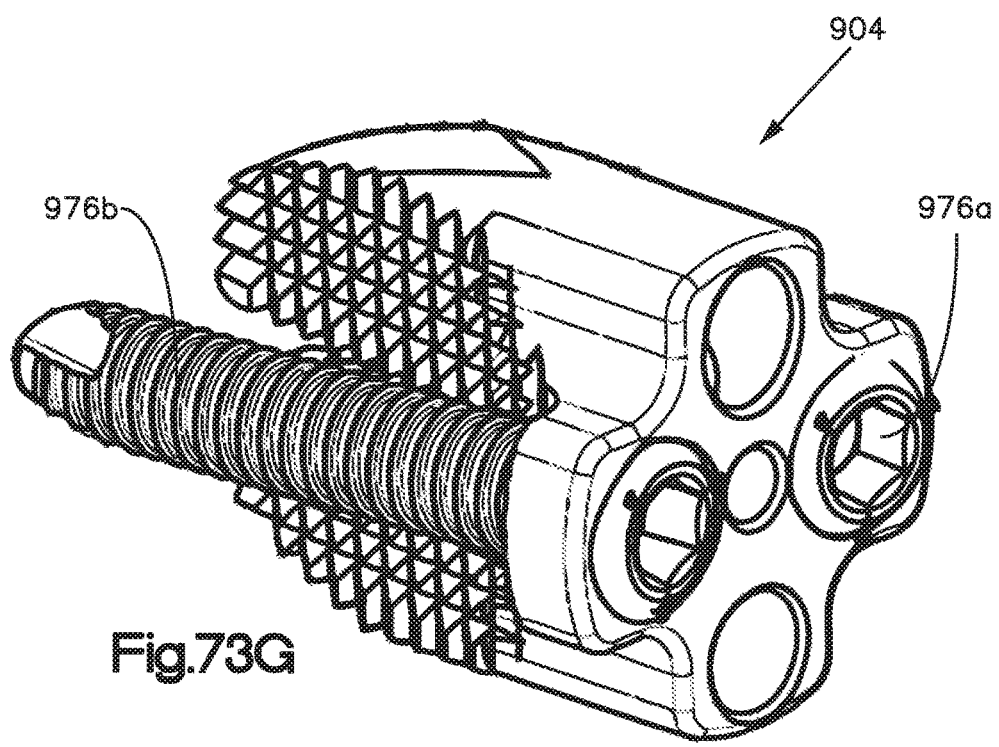
FIG. 73G is a front perspective view of the interbody implant shown in FIG. 73A having first and second bone fixation elements inserted through the first and second bone fixation element receiving apertures.
Figure 73H:
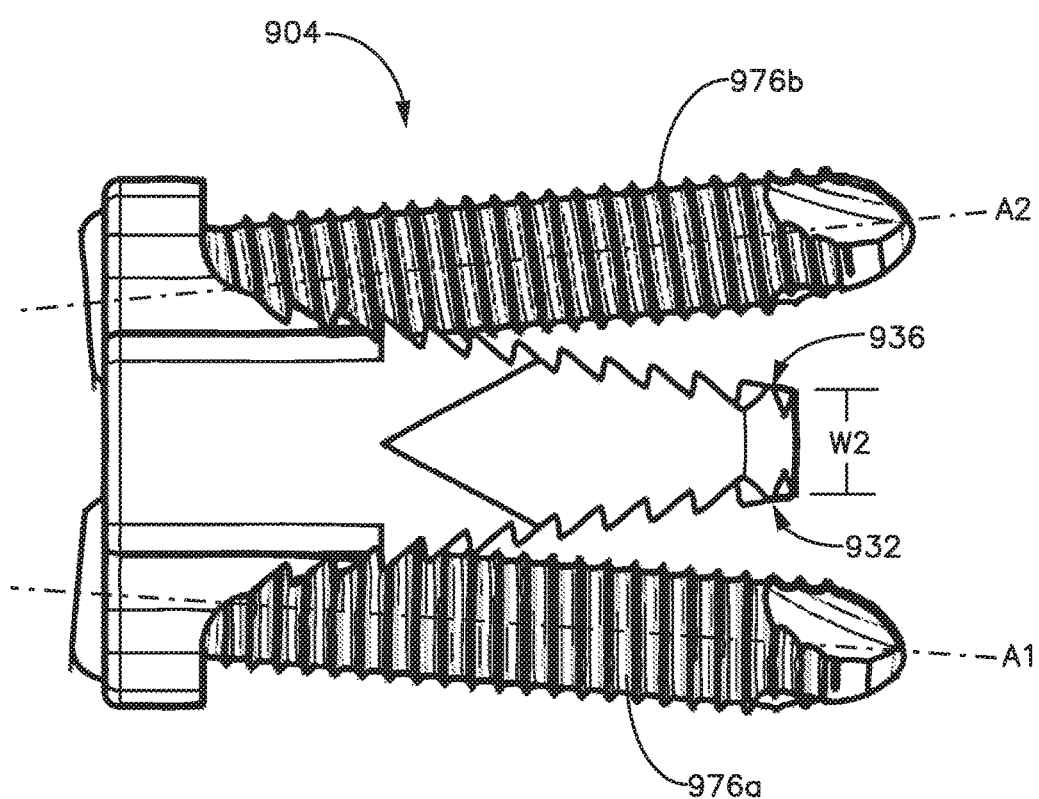
FIG. 73H is a side elevation view of the interbody implant shown in FIG. 73G showing the first and second bone fixation elements diverging as they extend along a direction from the proximal end to the distal end.

As shown in FIGS. 73C and 73E-73H, the head portion 928 further includes a first bone fixation element receiving aperture 974a that extends through the head body 970 along a first central axis $A_1$, and a second bone fixation element receiving aperture 974b that extends through the head body 970 along a second central axis $A_2$. As shown in FIGS. 73G and 73H, the first and second bone fixation element receiving apertures 974a and 974b are configured such that when the implant body 916 is received within the sacro-iliac joint 912, the first bone fixation element receiving aperture 974a is configured to receive a first bone fixation element 976a along the first central axis $A_1$ so as to align the first bone fixation element 976a with one of the sacral bone 914a or the iliac bone 914b and the second bone fixation element receiving aperture 974b is configured to receive a second bone fixation element 976b along the second central axis $A_2$ so as to align the second bone fixation element 976b with the other of the sacral bone 914a or the iliac bone 914b. It should be appreciated, that while the head portion 928 is illustrated as having two bone fixation element receiving apertures 974, the head portion 928 can have any number of bone fixation element receiving apertures 974 as desired. For example, the head portion 928 can have four bone fixation element receiving apertures.

The first and second bone fixation element receiving apertures 974a and 974b can be aligned along a first direction that is perpendicular to the insertion direction and can extend through the first and second projections 972a and 972b, respectively, of the head body 970 such that the first and second central axes $A_1$ and $A_2$ diverge as they extend along a direction from the proximal end 920 to the distal end 924 of the implant body 916. As shown in FIGS. 73G and 73H, the bone fixation element receiving apertures 974a and 974b are positioned relative to the implant body 916 such that the first axis $A_1$ of the first bone fixation element receiving aperture 974a diverges from the iliac engagement surface 932 and the second axis $A_2$ of the second bone fixation element receiving aperture 974b diverges from the sacral engagement surface 936. Therefore the first and second bone fixation elements 976a and 976b will diverge from the iliac and sacral engagement surfaces 932 and 936, respectively, when they are inserted into the first and second bone fixation element receiving apertures 974a and 974b. It should be appreciated, however, that the first and second bone fixation element receiving apertures 974a and 974b can extend through any portion of the head body 970 and that the first and second axes $A_1$ and $A_2$ can converge toward the engagement surfaces 932 and 936, as desired.

As shown in FIG. 73A, the first and second bone fixation element receiving apertures 974a and 974b can include internal threads 979 that are configured to mate with external threads of the bone fixation elements 976a and 976b when the bone fixation elements 976a and 976b are fully inserted in the channels 974a and 974b. It should be appreciate, however, that the apertures 974a and 974b can be void of threads 979, as desired.

As shown in FIGS. 73A and 73F, the head portion 928 further includes a first locking channel 980 that extends into the head body 970 along a first locking central axis $A_{L1}$ and a second locking channel 984 that extends into the head body 970 along a second locking central axis $A_{L2}$ that is angularly offset with respect to the first locking central axis $A_{L1}$. The first and second locking channels 980 and 984 are configured to receive first and second locking members of the insertion instrument 908 to thereby couple the implant 904 to the insertion instrument 908.

As shown in FIG. 73F, the first and second locking channels 980 and 984 are spaced from each other along a second direction that is perpendicular to both the first direction and the insertion direction I. The first locking channel 980 is oriented such that the first locking central axis $A_{L1}$ is parallel to the insertion direction I and the second locking channel 984 is oriented such that the second locking central axis $A_{L2}$ extends toward the first locking central axis $A_{L1}$. It should be appreciated, however, that in some embodiments, the second locking central axis $A_{L2}$ can be parallel to the insertion direction I and the first locking central axis $A_{L1}$ can extend toward the second locking central axis $A_{L2}$. Further, it should be appreciated, that rather than extend toward the other central axis, the angularly offset or otherwise oblique central axis can extend away from the other central axis or along any direction that is angularly offset with respect to the other central axis.

With continued reference to FIG. 73F, the first and second locking channels 980 and 984 can be cylindrical in shape as illustrated. It should be appreciated, however, that the first and second locking channels 980 and 984 can have any shape as desired. For example, the first and second locking channels 980 and 984 can be block shaped or irregularly shaped.

As shown in FIGS. 73F and 73E, the head portion 928 can further include a guide wire channel 988 that extends through the head body 970 along the insertion direction I and is coaxial or otherwise in-line with the guide wire channel 956 of the implant body 916. As shown, the guide wire channel 988 extends through the head body 970 between the first and second bone fixation element receiving apertures 974a and 974b and between the first and second locking channels 980 and 984. The guide wire channel 988 can be cylindrically shaped as illustrated or can have any shape as desired. The guide wire channel 988 is configured to receive a guide wire such as a K-wire or any other like device, as desired, so as to guide the implant 904 toward the sacro-iliac joint 912 during insertion of the implant 904.

Figure 74A:
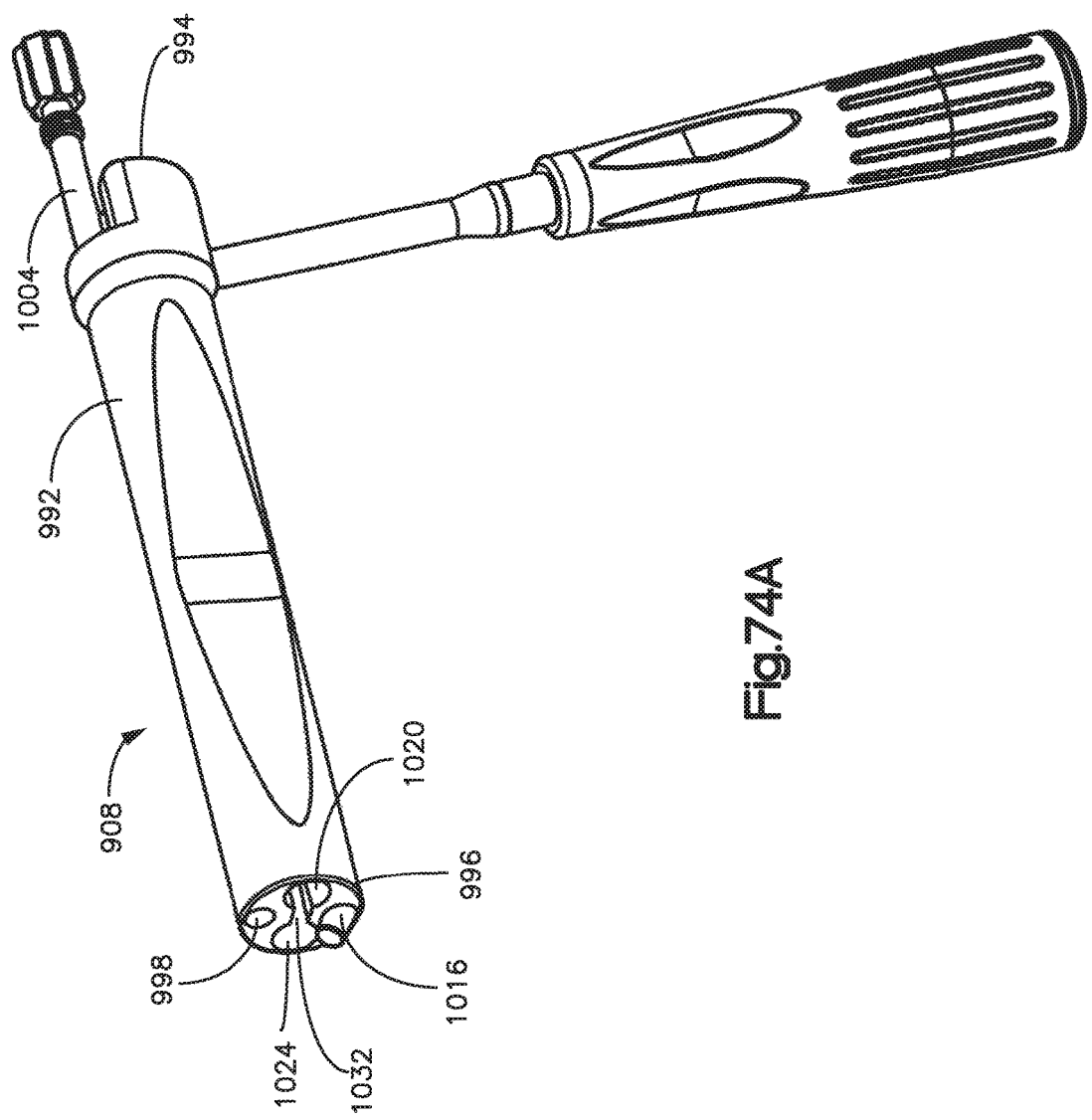
FIG. 74A is a perspective view of the insertion instrument shown in FIG. 72B, the insertion instrument including a guide body having a distal end and a proximal end, a channel that extends through at least a portion of the guide body along a central channel axis, a first locking member that extends from the distal end along a first member central axis that is angularly offset with respect to the central channel axis, and a second locking member that is movable within the channel between an unlocked position and a locked position.

Now in reference to FIGS. 74A-74B and 75A-75C, the insertion instrument 908 can be configured to insert an implant such as the implant 904 into a joint such as the sacro-iliac joint 912 defined between first and second bone parts. As shown in FIG. 74A, the insertion instrument 908 can include a guide body 992 that defines a proximal end 994 and a distal end 996 that is spaced from the proximal end 994 along a first direction such as the insertion direction I, and a handle 993 that extend from the guide body 992 and is configured to be gripped by a user of the instrument 908. The guide body 992 can be elongate along the first direction and cylindrical in shape. It should be appreciated, however, that the guide body 992 can have any shape as desired. For example, the guide body 992 can be oblong in cross-section.

Figure 75A:
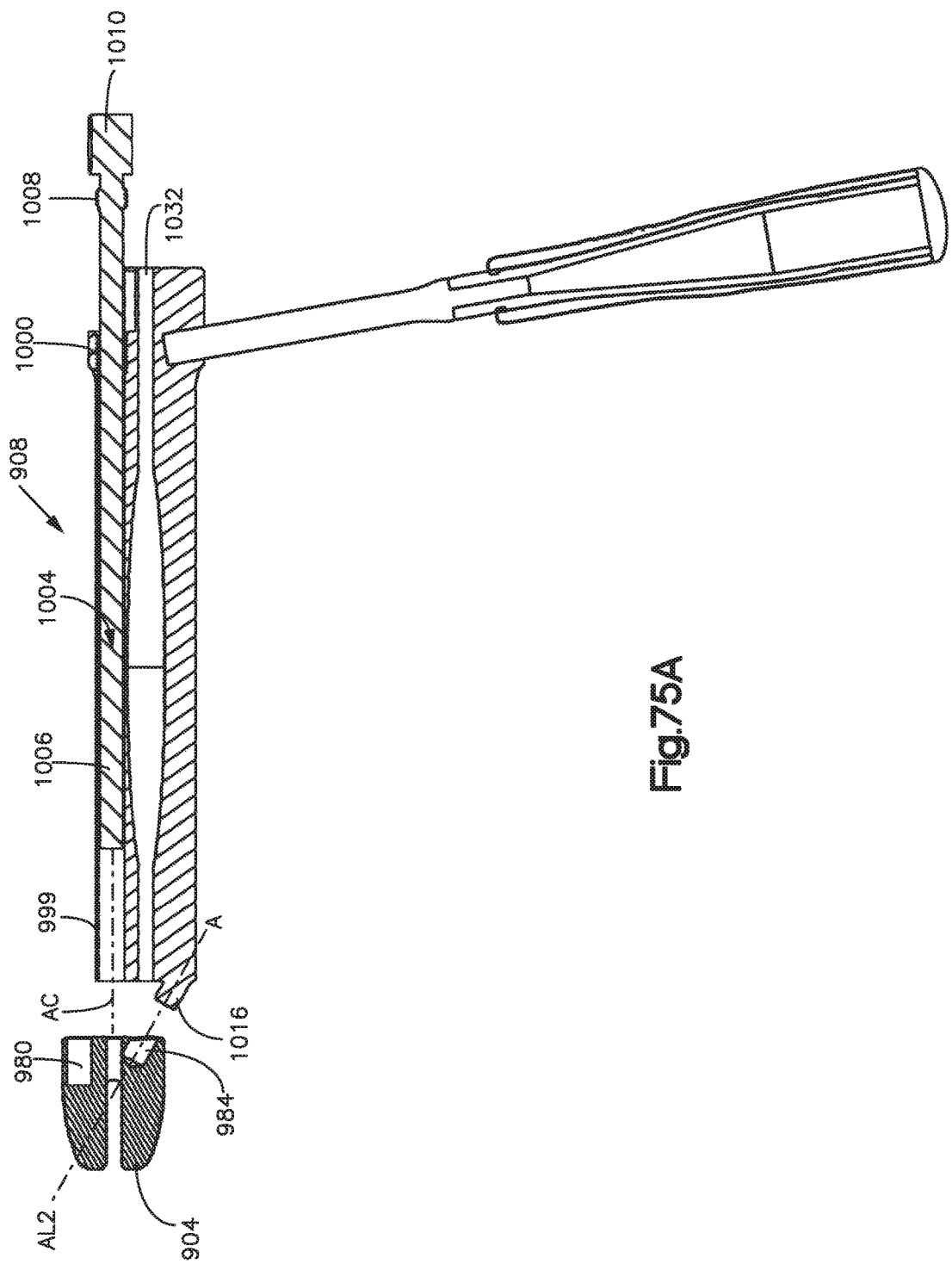
FIG. 75A is a side cross-sectional view of the insertion instrument shown in FIG. 74A being coupled to a the interbody implant shown in FIG. 73A.
Figure 75E:
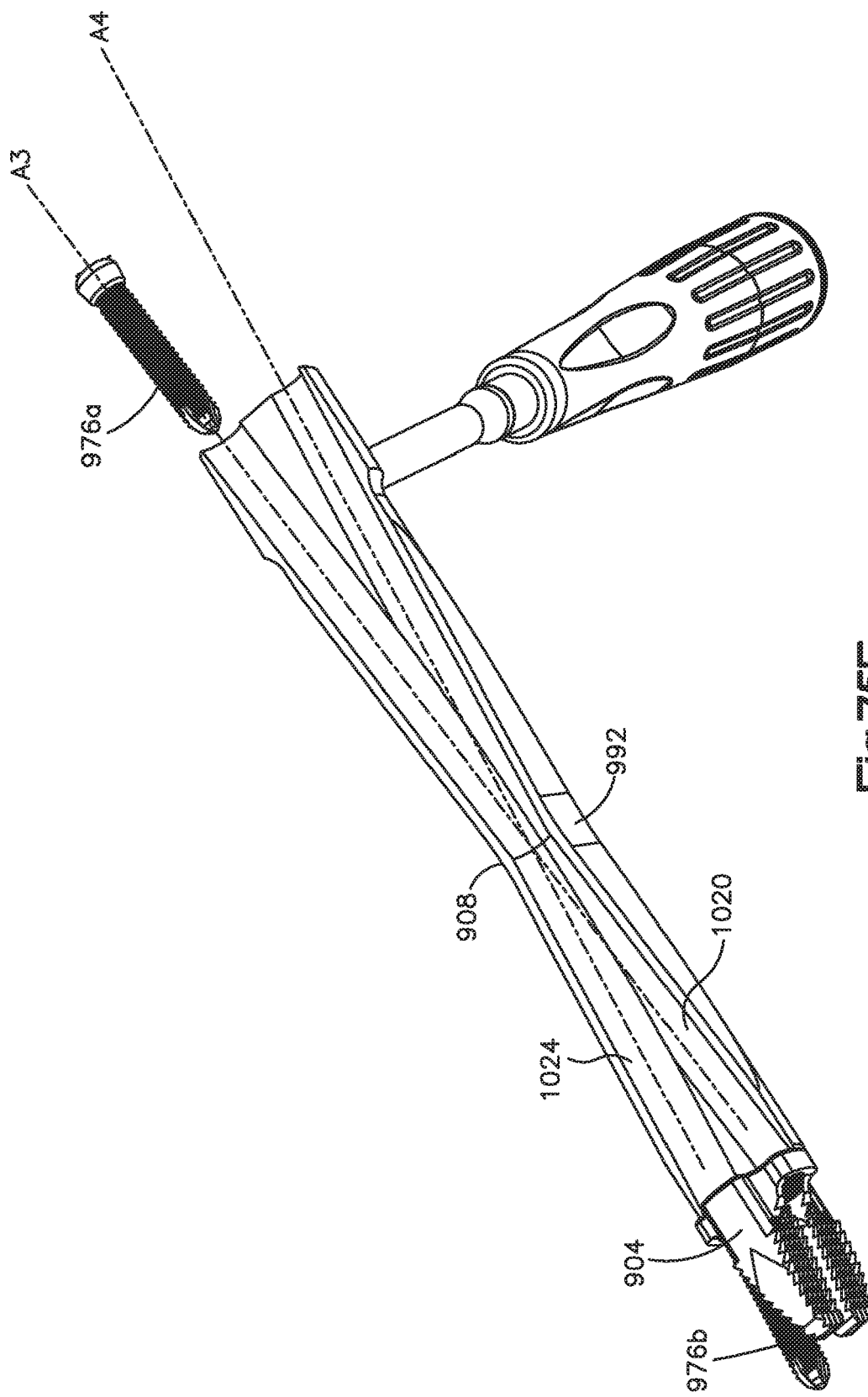
FIG. 75E is a perspective view of the insertion instrument shown in FIG. 75D with a first bone fixation element inserted into the second bone fixation element receiving aperture of the interbody implant.

As shown in FIGS. 74A and 75A-75C, the guide body 992 can have a channel 998 that extends through at least a portion of the guide body 992 along a central channel axis $A_C$ and extends out the distal end 996. The channel 998 is configured to receive a locking member such that the locking member can translate or otherwise move within the channel 998. In the illustrated embodiment, the channel 998 extends from the proximal end 994 through to the distal end 996 and the central channel axis $A_C$ is parallel to the first direction. As shown in FIG. 75A, the channel 998 can include a thread 1000 proximate to the proximal end 994 of the guide body 992. The thread 1000 can be configured to mate with the thread of a locking member to thereby fix the position of the locking member relative to the channel 998.

As shown in FIGS. 74A and 75A-75F, the insertion instrument 908 can further include a first locking member 1004 that is movable within the channel 998 of the guide body 992 between an unlocked position and a locked position. As shown in FIGS. 75A and 75B, the first locking member 1004 extends further from the distal end 996 when in the locked position than when in the unlocked position such that the first locking member engages or is otherwise received by the first locking channel 980 of the interbody implant 904. Therefore, the channel 998 of the guide body 992 is configured to be aligned with the first locking channel 980 of the implant 904 such that the channel central axis $A_C$ is coaxial with the first locking central axis $A_{L1}$ and so that the first locking member 1004 can move into the first locking channel 980 when moved from the unlocked position to the locked position. It should be appreciated, that when in the unlocked position a distal end of the first locking member 1004 can be proximal to the distal end 996 of the guide body 992 or distal to the distal end 996.

The first locking member 1004 can be a rod 1006 that is elongate along the first direction and can include a thread 1008 proximate to a proximal end of the rod 1006. When the first locking member 1004 is moved toward the locked position, the thread 1008 of the first locking member 1004 will be adjacent to the thread 1000 of the channel 998. Rotation of the first locking member 1004 will then cause the thread 1008 to mate with the thread 1000 and cause the first locking member 1004 to incrementally move toward the locked position and also fix the position of the first locking member 1004 relative to the channel 998. It should be appreciated, that the first locking member 1004 can have other engagement features that are configured to fix the position of the first locking member 1004 relative to the channel 998. For example, the first locking member 1004 can have a snap, bayonet, or frictional feature configured to fix the position of the first locking member 1004.

As shown in FIG. 74A, the first locking member 1004 can further include a handle or knob 1010 that extends proximally from the proximal end of the rod 1006. The handle or knob 1010 can be gripped by a user to thereby move the first locking member 1004 and/or rotate the first locking member 1004. The knob 1010 can define a shoulder 1012 that is configured to abut the proximal end of the guide body 992 when the first locking member 1004 is in the locked position.

As shown in FIGS. 74A and 75A-75C, the insertion instrument 908 can further include a second locking member 1016 that extends from the distal end 996 of the guide body 992 along a second member central axis $A_M$ that is angularly offset with respect to the central channel axis $A_C$. The second locking member 1016 can be configured to be aligned with and subsequently received by the second locking channel 984 of the implant 904. Therefore, the second member central axis $A_M$ is configured to be coaxial with the second locking central axis $A_{L2}$. As shown, the second locking member 1016 extends toward the first locking member 1004 when the first locking member 1004 is in the locked position.

In the illustrated embodiment, the second locking member 1016 is monolithic with the guide body 992 and is substantially cylindrical. It should be appreciated, however, that the second locking member 1016 can have any configuration as desired. For example, the second locking member 1016 can be block or irregularly shaped, or the second locking member 1016 can be moveable within a channel defined by the guide body 992. Therefore it should be appreciated, that either the first, the second or both of the locking members 1004 and 1016 can be movable with respect to the guide body 992.

To couple the implant 904 to the insertion instrument 908, the second locking member is inserted into the second locking channel 984 of the implant 904. When inserted, the channel 998 of the guide body 992 is configured to be aligned with the first locking channel 980 of the implant 904 such that the channel axis $A_C$ is coaxial with the first locking central axis $A_{L1}$ and movement of the first locking member 1004 from the unlocked position to the locked position causes the first locking member 1004 to be inserted into the first locking channel 980 of the implant 904 to thereby couple the implant 904 to the insertion instrument 908.

As shown in FIGS. 74A and 74B, and FIGS. 75D-75F, the guide body 992 can further include a first bone fixation element receiving channel 1020 that extends from the proximal end 994 through to the distal end 996 and a second bone fixation element receiving channel 1024 that extends from the proximal end 994 through to the distal end 996. The first and second bone fixation element receiving channels 1020 and 1024 are each configured to receive a bone fixation element so as to guide the bone fixation element toward the implant 904. In particular, the first and second bone fixation element receiving channels 1020 and 1024 define first and second central axes $A_3$ and $A_4$ that are configured to be coaxial with the first and second axes $A_1$ and $A_2$ of the first and second bone fixation element receiving channels 974a and 974b of the implant 904 when the implant 904 is coupled to the insertion instrument 908. Therefore, as first and second bone fixation elements are passed through the bone fixation element receiving channels 1020 and 1024 of the guide body 992, they will automatically be directed into and passed through the bone fixation element receiving channels 974a and 974b of the implant 904.

As shown in FIGS. 74B and 75D-75F, the first and second bone fixation element receiving channels 1020 and 1024 each extend at an angle with respect to a central axis of the guide body 992 such that first and second bone fixation element receiving channels 1020 and 1024 cross as they extend from the proximal end 994 to the distal end 996. For example, the first and second bone fixation element receiving channels 1020 and 1024 can extend at an angle that is between about 5° and about 15° and preferably at about 10°. It should be appreciated, however, that the first and second bone fixation receiving channels 1020 and 1024 can extend at any angle as desired. Further, it should be appreciated, that the bone fixation receiving channels 1020 and 1024 can be configured to receive an awl, drill bit or other device in addition to bone fixation elements so as to be able to prepare the sacral bone and iliac bone through the channels 1020 and 1024 and ensure suitable alignment of the prepared bone channels with the final bone fixation element positions. While the insertion instrument 908 is described as having first and second bone fixation element receiving channels 1020 and 1024 it should be appreciated, that the insertion instrument 908 can be configured to have any number of bone fixation element receiving channels as desired. For example, the insertion instrument 908 can be configured to have four bone fixation element receiving channels.

Figure 74B:
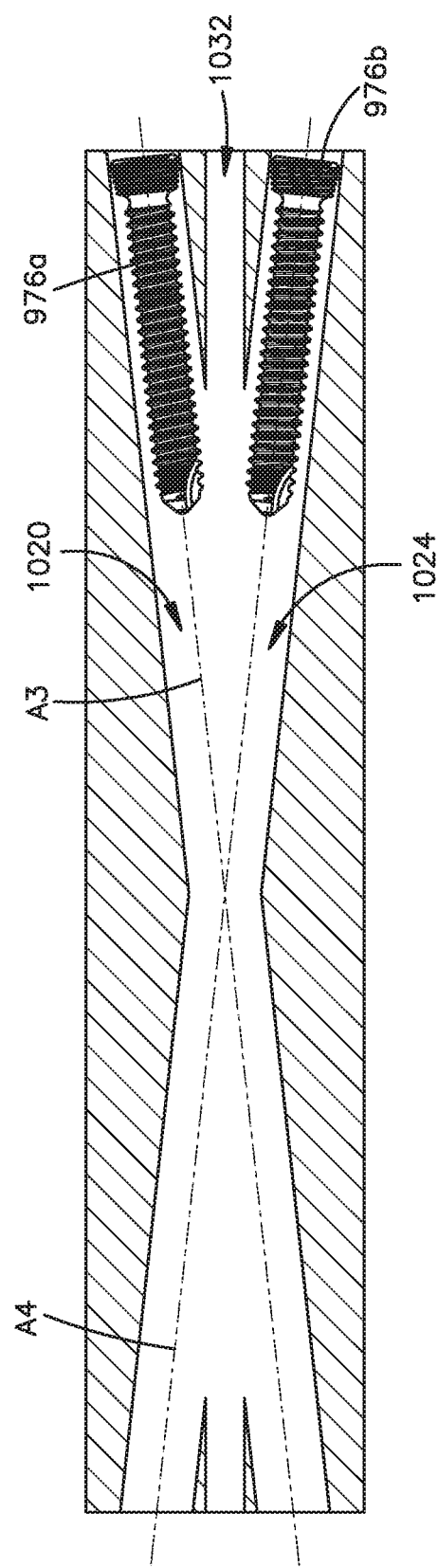
FIG. 74B is a bottom cross-sectional view of the insertion instrument shown in FIG. 74A illustrating first and second bone fixation element receiving channels that extend through the guide body of insertion instrument.

With continued reference to FIGS. 74A-74B and 75B-75C, the guide body 992 can further include a guide wire channel 1032 that extends from the proximal end 994 through to the distal end 996 along the insertion direction I. When the implant 904 is coupled to the insertion instrument 908 the guide wire channel 1032 of the guide body 992 can be aligned with or otherwise coaxial with the guide wire channels 956 and 988 of the implant body 916 and head portion 928 of the implant 904. The guide wire channel 1032 can be configured to receive a guide wire, such as a K-wire or other like device to thereby guide the instrument 908 toward the joint 912. As shown in FIG. 74B, the guide wire channel 1032 can extend through the bone fixation element receiving channels 1020 and 1024 at the point where they cross and can be substantially cylindrically shaped as illustrated. It should be appreciated, however, that the guide wire channel 1032 can extend through the guide body 992 such that it does not extend through the bone fixation element receiving channels 1020 and 1024. Further, it should be appreciated, that the guide wire channel 1032 can have any shape as desired. For example, the guide wire channel 1032 can have a substantially square shape in cross-section.

In operation, the implant 904 can be coupled to the insertion instrument 908 by positioning the implant 904 proximate to the distal end 996 of the guide body 992 such that the second locking member 1016 is aligned with the second locking channel 984 of the implant 904. The second locking member 1016 can then be inserted into the second locking channel 984 such that when inserted, the channel 998 of the guide body 992 is aligned with the first locking channel 980. By moving the first locking member 1004 within the channel 998 from the unlocked position to the locked position the distal end of the first locking member 1004 will engage the first locking channel to thereby couple the implant 904 to the insertion instrument 908. Rotation of the first locking member 1004 will cause the thread of the first locking member to mate with the thread of the channel 998 to thereby fix the first locking member 1004 in the locked position. When the implant 904 is coupled to the insertion instrument 908, the first and second bone fixation receiving channels 1020 and 1024 of the guide body 992 are aligned or otherwise coaxial with the first and second bone fixation receiving channels 974a and 974b of the implant and the guide wire channel 1032 of the guide body 992 is aligned or otherwise coaxial with the guide wire channel 988 of the head portion 928.

Figure 76D:
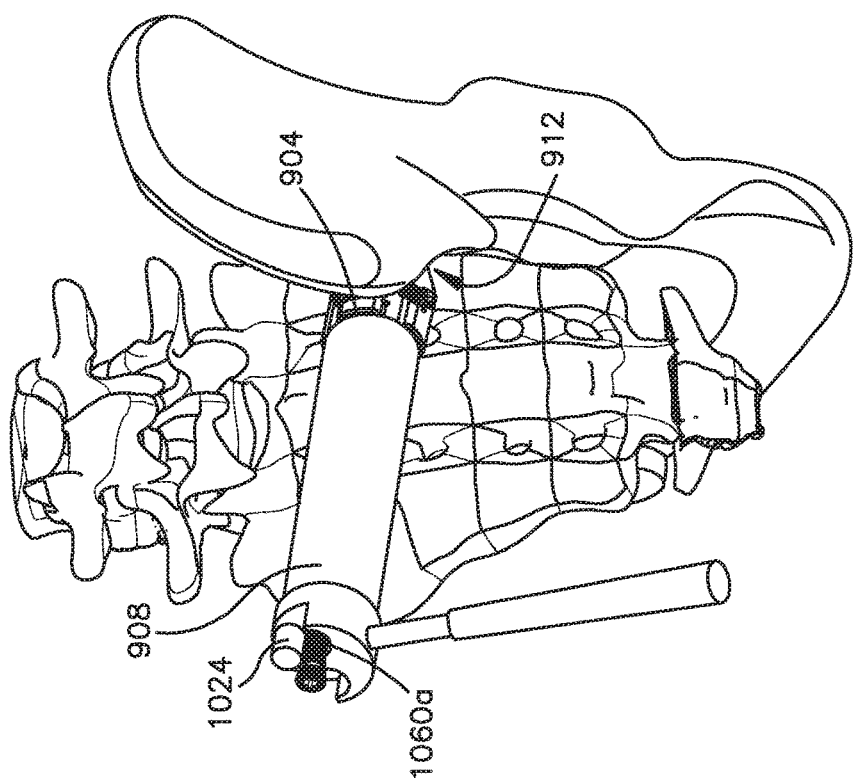
FIG. 76D is a perspective view of a first bone fixation element being inserted through a first bone fixation element receiving channel of the insertion instrument and toward the implant.

Now in reference to FIGS. 76A-76F, to insert the implant 904 now coupled to the insertion instrument 908 into an interbody space such as the sacro-iliac joint 912, a guide wire 1050 can be first inserted into the sacro-iliac joint 912 such that the guide wire extends out from the joint 912. Once inserted, a rasp 1054 can be guided along the guide wire 1050 toward the sacro-iliac joint 912, as shown in FIG. 76B. The rasp 2054 can be used to prepare the joint to match the geometry of the implant 904.

Figure 76C:
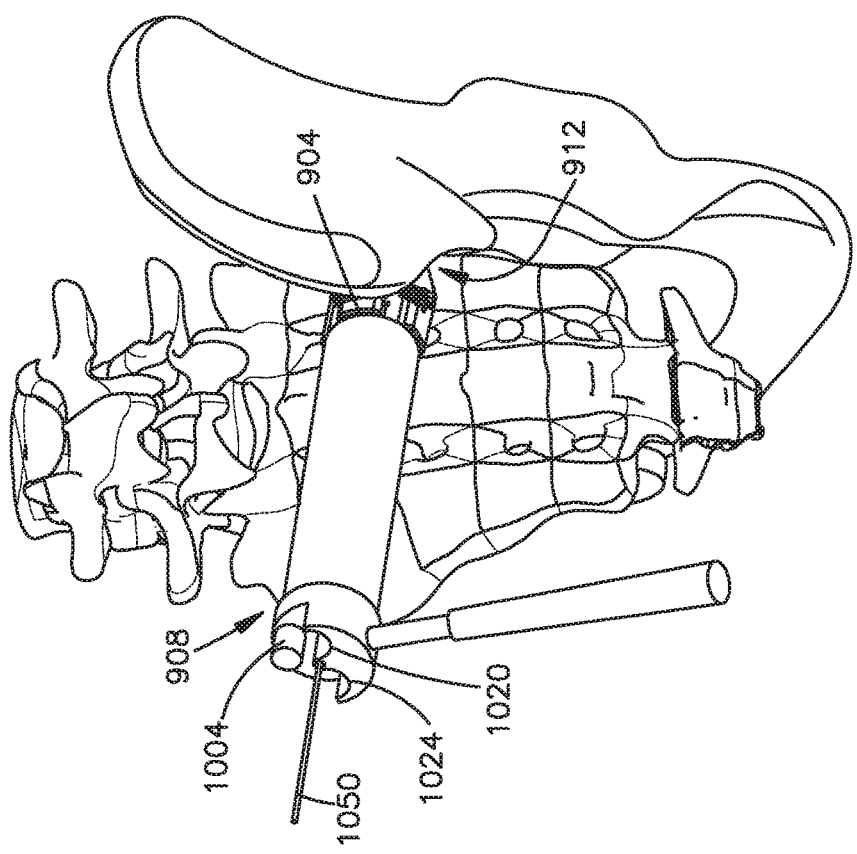
FIG. 76C is a perspective view of the insertion instrument coupled to the interbody implant and being guided along the guide wire so as to insert at least a portion of the implant into the sacro-iliac joint.

After the rasp 1054 is slid off of the guide wire 1050 the insertion instrument 908 can be guided along the guide wire 1050 until at least a portion of the implant 904 such as the implant body 916 is inserted into the sacro-iliac joint 912 as shown in FIG. 76C. In particular, the guide wire 1050 is slid through the guide wire channels 956, 988, and 1032 of the implant body 916, head portion 928 and guide body 992, respectively. The insertion instrument 908 can be tapped using a hammer to force the implant body 916 into the joint 912. The wedge shape of the implant body 916 will help ensure a press-fit of the implant body 916 within the joint 912.

Figure 76F:
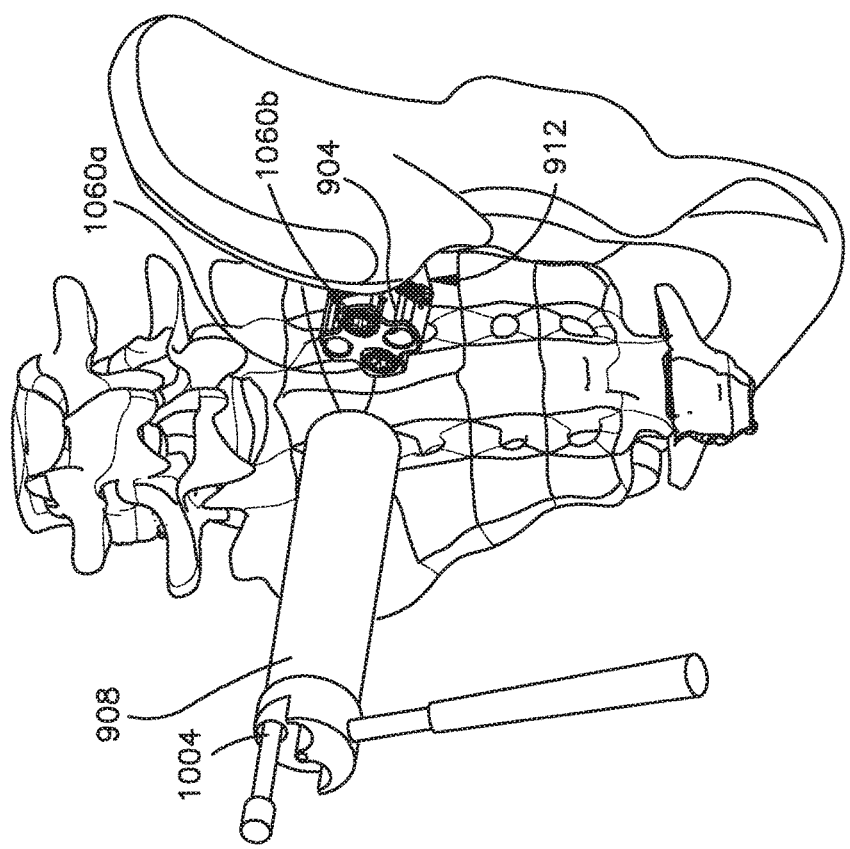
FIG. 76F is a perspective view of the insertion instrument decoupled from the implant.
Figure 76E:
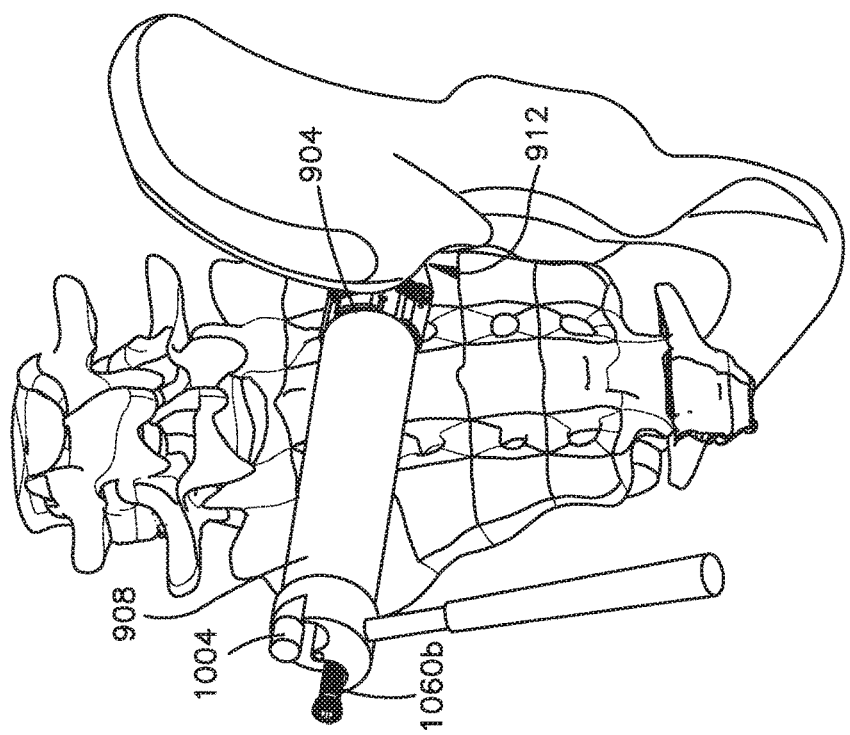
FIG. 76E is a perspective view of a second bone fixation element being inserted through a second bone fixation element receiving channel of the insertion instrument and toward the implant.

As shown in FIGS. 76D and 76E, a first bone fixation element 1060a can be passed through the first bone fixation element receiving channel 1020 of the insertion instrument 908 and into the first bone fixation element receiving channel 974a of the implant 904 so that the first bone fixation element 1060*a* engages a first bone that at least partially defines the sacro-iliac joint 912 to thereby fix the implant 904 to the first bone. As shown in FIG. 76E a second bone fixation element 1060*b* can be passed through the second bone fixation element receiving channel 1024 of the insertion instrument 908 and into the second bone fixation element receiving channel 974*b* of the implant 904 so that the second bone fixation element 1060*b* engages a second bone that at least partially defines the sacro-iliac joint 912 to thereby fix the implant 904 to the second bone. After the implant 904 has been fixed to the first and second bones, the first locking member 1004 can be moved to the unlocked position so as to decouple the insertion instrument 908 from the implant 904 as shown in FIG. 76F.

Figure 77:
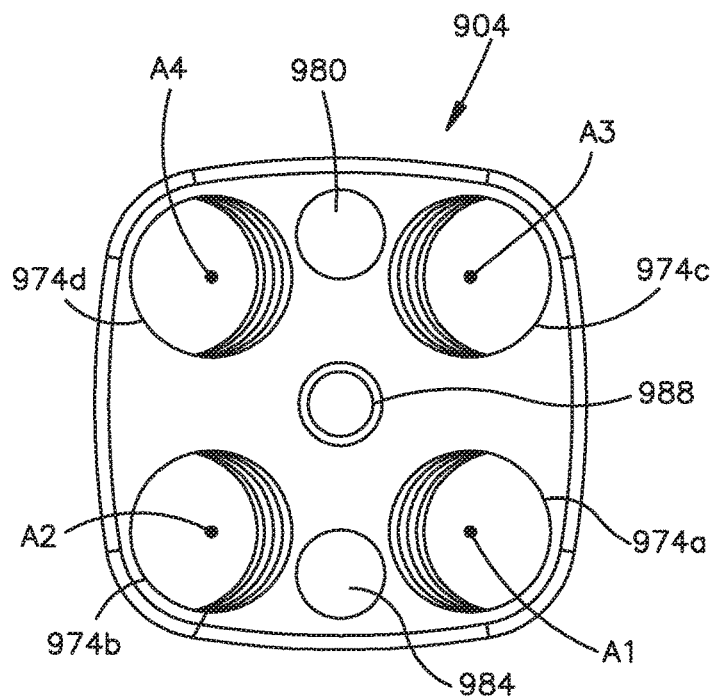
FIG. 77 is a front plan view of the interbody implant shown in FIG. 73A including a head portion having first, second, third, and fourth bone fixation element receiving apertures.

Now in reference to FIG. 77, the interbody implant 904 can be configured to have four bone fixation element receiving apertures. As shown in FIG. 77, the implant 904 can be configured such that the head portion 928 further includes third and fourth bone fixation element receiving apertures 974*c* and 974*d* that extend through the head body 970 along third and fourth central axes $A_3$ and $A_4$, respectively, such that when the implant body 916 is received within the sacro-iliac joint 912, the third and fourth bone fixation element receiving apertures 974*c* and 974*d* are configured to receive third and fourth bone fixation elements along the third and fourth axes $A_3$ and $A_4$, respectively, so as to align the third and fourth bone fixation elements with one of the sacral bone or the iliac bone.

As shown in FIG. 77, the third bone fixation element receiving aperture 974*c* is aligned with the first bone fixation element receiving aperture 974*a* along a first direction and the fourth bone fixation element receiving aperture 974*d* is aligned with the second bone fixation element receiving aperture 974*b* along a second direction that is substantially parallel to the first direction. The first, second, third, and fourth bone fixation element receiving apertures 974*a*-974*d* are positioned with respect to each other such that the first and second locking channels 980 and 984 are between the first and second bone fixation element receiving apertures 974*a* and 974*b* and between the third and fourth bone fixation element receiving apertures 974*c* and 974*d*. It should be appreciated, however, that the bone fixation element receiving apertures can have any position and configuration as desired.

The first, second, third, and fourth bone fixation element receiving apertures 974*a*-974*d* can be oriented such that at least one of the first and second central axes $A_1$ and $A_2$ is parallel to at least one of the third and fourth central axes $A_3$ and $A_4$. For example, in the illustrated embodiment the first and third central axes $A_1$ and $A_3$ are parallel and the second and fourth central axes $A_2$ and $A_4$ are parallel. It should be appreciated, however, that the central axes $A_1$-$A_4$ can have any orientations as desired. For example, in some embodiments, at least one of the first and third central axes $A_1$ and $A_3$ can be parallel to at least one of the second and fourth central axes $A_2$ and $A_4$.

Now in reference to FIGS. 79A-79E, an implant system 1200 can include interbody implant 1204 configured to be inserted along the insertion direction into the sacro-iliac joint and a rod 1208 configured to be secured to the interbody implant 1204. The interbody implant 1204 is similar to the interbody implant 904 and includes like structure unless otherwise described.

As shown in FIGS. 79B-79E the interbody implant 1204 can be substantially wedge shaped and can include an implant body 1216 having a proximal end 1220 and a distal end 1224 spaced from the proximal end 1220 along the insertion direction I. The implant 1204 can further include a head portion 1228 that extends from the proximal end 1220 of the implant body 1216 along a proximal direction that is opposite the insertion direction I. The implant body 1216 can be sized and configured to be inserted into the sacro-iliac joint 912 and the head portion 1228 can be configured to receive at least one such as two bone fixation elements to thereby fix the implant 1204 within the sacro-iliac joint 912. It should be appreciated, however, that the implant 1204 can be configured to be inserted into any joint defined between any two bones.

Figure 79A:
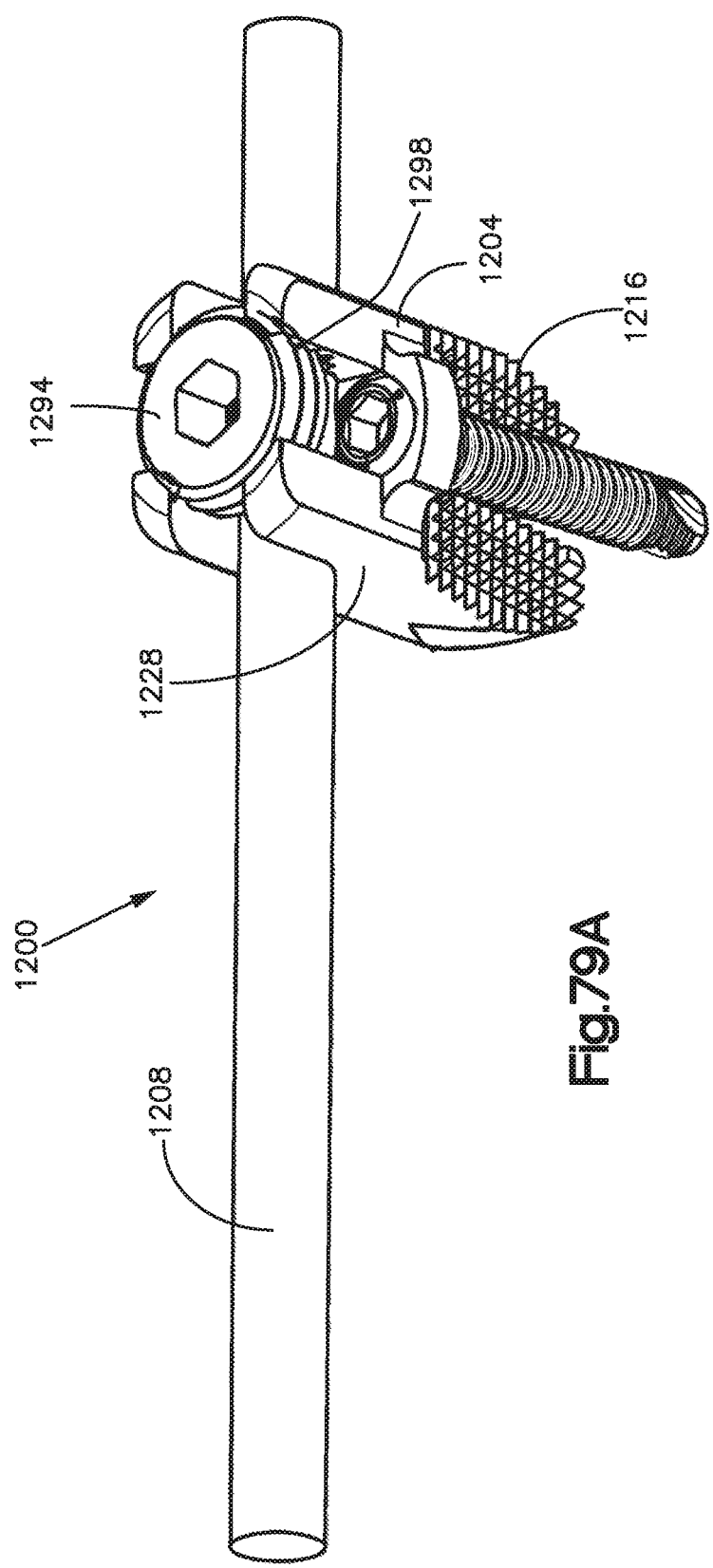
FIG. 79A is a perspective view of a system including an interbody implant in accordance with another embodiment and a rod, the implant including a head portion that defines a rod-receiving channel configured to receive a rod and a locking cap to thereby secure the rod within the rod-receiving channel.
Figure 79B:
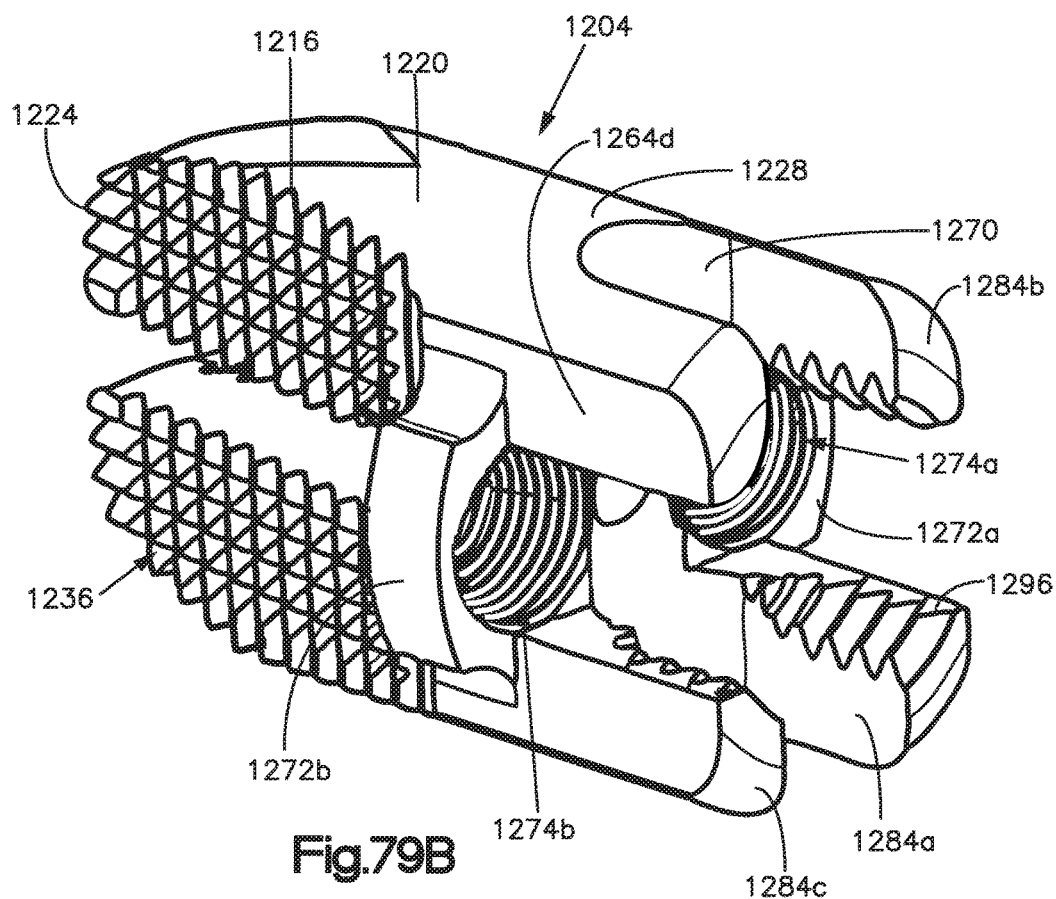
FIG. 79B is a perspective view of the interbody implant shown in FIG. 79A.
Figure 79C:
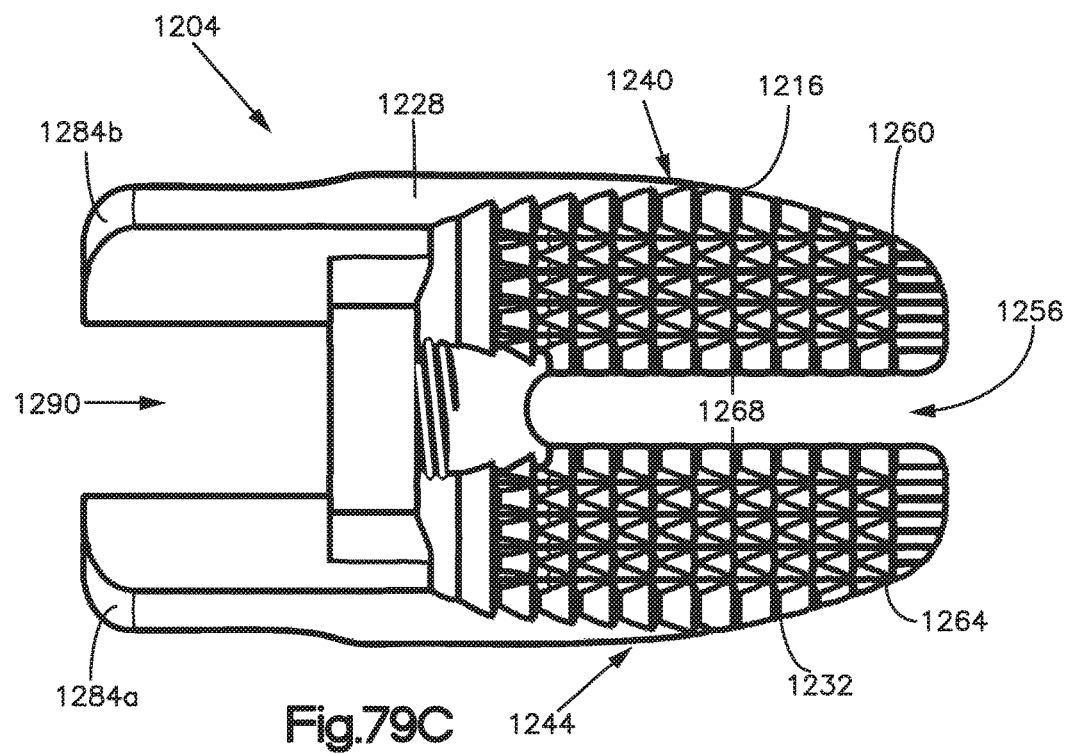
FIG. 79C is a side elevation view of the interbody implant shown in FIG. 79B.

As shown in FIG. 79B-79E, the implant body 1216 defines a first or iliac engagement surface 1232 and a second or sacral engagement surface 1236 that are each substantially planar and extend from the proximal end 1220 to the distal end 1224 of the implant body 1216. The iliac engagement surface 1232 can be sized and configured to abut the iliac bone 914*b* when the implant 1204 is inserted into the sacro-iliac joint 912, and the sacral engagement surface 1236 can be sized and configured to abut the sacral bone 914*a* when the implant 1204 is inserted into the sacro-iliac joint 912. The implant body 1216 can further include third and fourth side surfaces 1240 and 1244 that connect the iliac and sacral engagement surfaces 1232 and 1236. As shown in FIG. 79C, the third and fourth side surfaces 1240 and 1244 taper as they extend along the insertion direction I. It should be appreciated, however, that the third and fourth surfaces 1240 and 1244 can be parallel along the entire length of the implant body 1216, as desired.

Figure 79D:
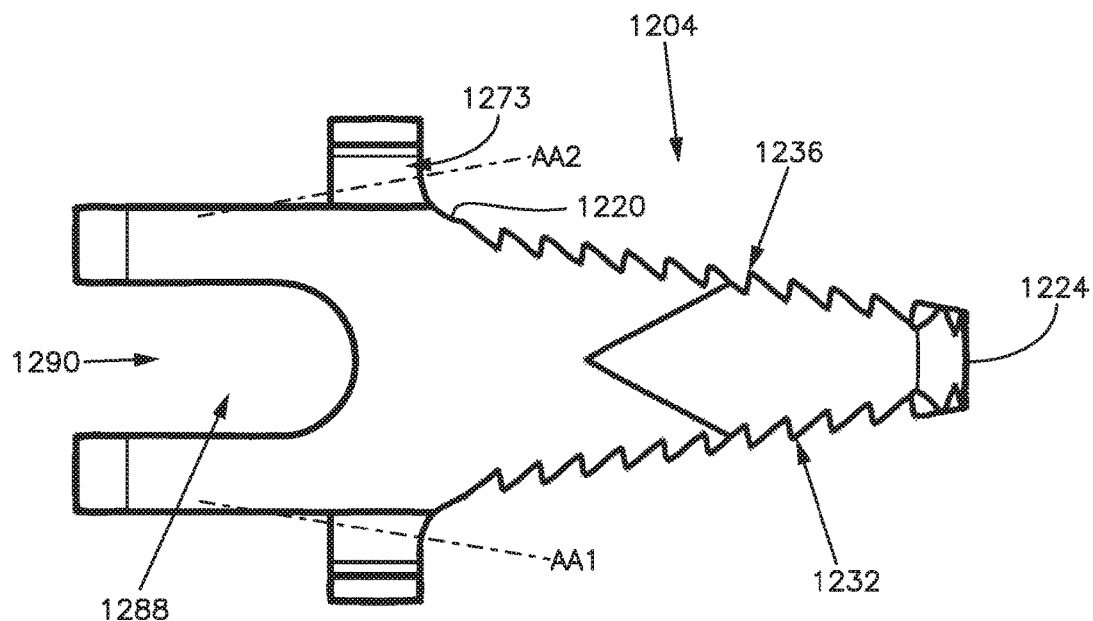
FIG. 79D is a top plan view of the interbody implant shown in FIG. 79B.

As shown in FIG. 79D, at least one of the iliac engagement surface 1232 and the sacral engagement surface 1236 converges toward the other of the iliac engagement surface 1232 and the sacral engagement surface 1236 as it extend along a direction from the proximal end 1220 to the distal end 1224 (such as the insertion direction I). In the illustrated embodiment, both the iliac engagement surface 1232 and the sacral engagement surface 1236 converge toward each other as they extend from the proximal end 1220 to the distal end 1224. That is, the iliac engagement surface 1232 and the sacral engagement surface 1236 extend from the proximal end 1220 to the distal end 1224 at an angle with respect to the longitudinal axis to define a tapered wedge-shape. It should be appreciated that while in the illustrated embodiment the entire iliac engagement surface 1232 and the entire sacral engagement surface 1236 converges toward the other, in some embodiments, only a portion of the iliac engagement surface 1232 and/or the sacral engagement surface 1236 can converge toward the other, if desired. Further, it should be appreciated that in some embodiments the sacral engagement surface 1236 and iliac engagement surface 1232 can be parallel to each other, as desired.

Figure 79E:
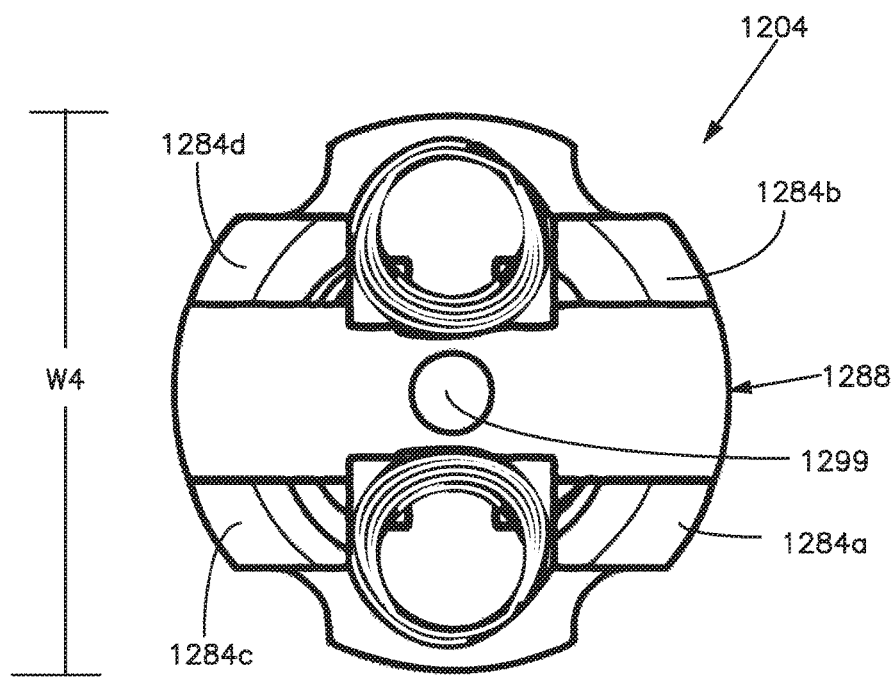
FIG. 79E is a front plan view of the interbody implant shown in FIG. 79B.

As shown in FIGS. 79C and 79E, the implant body 1216 can further include a guide wire receiving channel 1256 that extends therethrough along the insertion direction I from the proximal end 1220 to the distal end 1224 such that the guide wire channel of the head portion is coaxial with the guide wire channel 1256 of the implant body 1216. The guide wire channel 1256 can be configured to receive a guide wire such as a K-wire, or any other like device as desired so as to guide the implant 1204 toward the sacro-iliac joint 912. In the illustrated embodiment, the implant body 1216 includes a first body portion 1260 and a second body portion 1264 that is separated from the first body portion 1260 along a direction that is perpendicular to the insertion direction I such that a gap 1268 is defined between the first and second body portions 1260 and 1264 along at least a portion such as along the entire length of the implant body 1216 from the proximal end 1220 to the distal end 1224. As shown in FIG. 79C, the gap 1268 defines the guide wire channel 1256 of the implant body 1216. It should be appreciated, however, that the implant body 1216 can be configured as a single body portion having a guide wire channel extending through the single body portion.

With continued reference to FIGS. 79A-79E, the head portion 1228 extends from the proximal end 1220 of the implant body 1216 along the proximal direction and includes a head body 1270 having a width $W_4$ measured along a direction that is perpendicular to the insertion direction that is greater than that of the proximal end 1220 of the implant body 1216 such that the head body 1270 defines a first projection 1272*a* that extends beyond the iliac engagement surface 1232 and a second projection 1272*b* that extends beyond the sacral engagement surface 1236. Both the first and second projections 1272*a* and 1272*b* define abutment surfaces 1273 that can provide surfaces that abut outer surfaces of the iliac and sacral bones 914*a* and 914*b* to thereby act as a stop so as to prevent the head portion 1228 from being inserted into the sacro-iliac joint 912. In the illustrated embodiment, the head portion 1228 defines a cross-shape, though it should be appreciated that the head portion can define any shape as desired. Further, it should be appreciated, that the head portion 1228 can be configured so as to be void of the abutment surfaces 1273, as desired.

As shown in FIGS. 79D and 79E, the head portion 1228 further includes a first bone fixation element receiving aperture 1274*a* that extends through the head body 1270 along a first central axis $A_{A1}$, and a second bone fixation element receiving aperture 1274*b* that extends through the head body 1270 along a second central axis $A_{A2}$. As shown in FIG. 79A, the first and second bone fixation element receiving apertures 1274*a* and 1274*b* are configured such that when the implant body 1216 is received within the sacro-iliac joint 912, the first bone fixation element receiving aperture 1274*a* is configured to receive a first bone fixation element 976*a* along the first central axis $A_{A1}$ so as to align the first bone fixation element 976*a* with one of the sacral bone 914*a* or the iliac bone 914*b* and the second bone fixation element receiving aperture 1274*b* is configured to receive a second bone fixation element 976*b* along the second central axis $A_{A2}$ so as to align the second bone fixation element 976*b* with the other of the sacral bone 914*a* or the iliac bone 914*b*. It should be appreciated, that while the head portion 1228 is illustrated as having two bone fixation element receiving apertures 1274, the head portion 1228 can have any number of bone fixation element receiving apertures 1274 as desired. For example, the head portion 1228 can have four bone fixation element receiving apertures.

The first and second bone fixation element receiving apertures 1274*a* and 1274*b* can be aligned along a first direction that is perpendicular to the insertion direction and can extend through the first and second projections 1272*a* and 1272*b*, respectively, of the head body 1270 such that the first and second central axes $A_{A1}$ and $A_{A2}$ diverge as they extend along a direction from the proximal end 1220 to the distal end 1224 of the implant body 1216. As shown in FIG. 79D, the bone fixation element receiving apertures 1274*a* and 1274*b* are positioned relative to the implant body 1216 such that the first axis $A_{A1}$ of the first bone fixation element receiving aperture 1274*a* diverges from the iliac engagement surface 1232 and the second axis $A_{A2}$ of the second bone fixation element receiving aperture 1274*b* diverges from the sacral engagement surface 1236. Therefore the first and second bone fixation elements 976*a* and 976*b* will diverge from the iliac and sacral engagement surfaces 1232 and 1236, respectively, when they are inserted into the first and second bone fixation element receiving apertures 1274*a* and 1274*b*. It should be appreciated, however, that the first and second bone fixation element receiving apertures 1274*a* and 1274*b* can extend through any portion of the head body 1270 and the first and second axes $A_{A1}$ and $A_{A2}$ can converge toward the engagement surfaces 1232 and 1236, as desired.

With continued reference to FIGS. 79A-79E, the head portion 1228 further includes at least a first leg 1284*a* and a second leg 1284*b* that extend from the head body 1270 along the proximal direction. The first leg 1284*a* can be spaced from the second leg 1284*b* along a direction that is substantially perpendicular to the insertion direction such that a rod receiving channel 1288 is defined between the first and second legs 1284*a* and 1284*b*. In the illustrated embodiment, the head portion 1228 further includes a third leg 1284*c* and a fourth leg 1284*d* that extend from the head body 1270 along the proximal direction. As shown, the first, second, third, and fourth legs 1284*a*-1284*d* are spaced from each other so as to define the rod receiving channel 1288 and a locking cap channel 1290 configured to receive a locking cap 1294 along the insertion direction I. It should be appreciated, however, that the head portion can include first and second legs that define both the rod receiving channel and the locking cap channel.

As shown in FIGS. 79A and 79E, each of the legs 1284*a*-1284*c* defines an internal thread 1296 that is configured to mate with an external thread 1298 of the locking cap 1294 when the locking cap 1294 is received within the locking cap channel 1290. The locking cap 1290 can be configured to secure the rod within the rod receiving channel 1288 so as to couple the rod to the implant 1204.

As shown in FIG. 79E, the head portion 1228 can further include a guide wire channel 1299 that extends through the head body 1270 along the insertion direction I and is coaxial or otherwise in-line with the guide wire channel 1256 of the implant body 1216. As shown, the guide wire channel 1299 extends through the head body 1270 between the first and second bone fixation element receiving apertures 1274*a* and 1274*b*. The guide wire channel 1299 can be cylindrically shaped as illustrated or can have any shape as desired. The guide wire channel 1299 is configured to receive a guide wire such as a K-wire or any other like device, as desired so as to guide the implant 1204 toward the sacro-iliac joint 912 during insertion of the implant 904.

Figure 80:
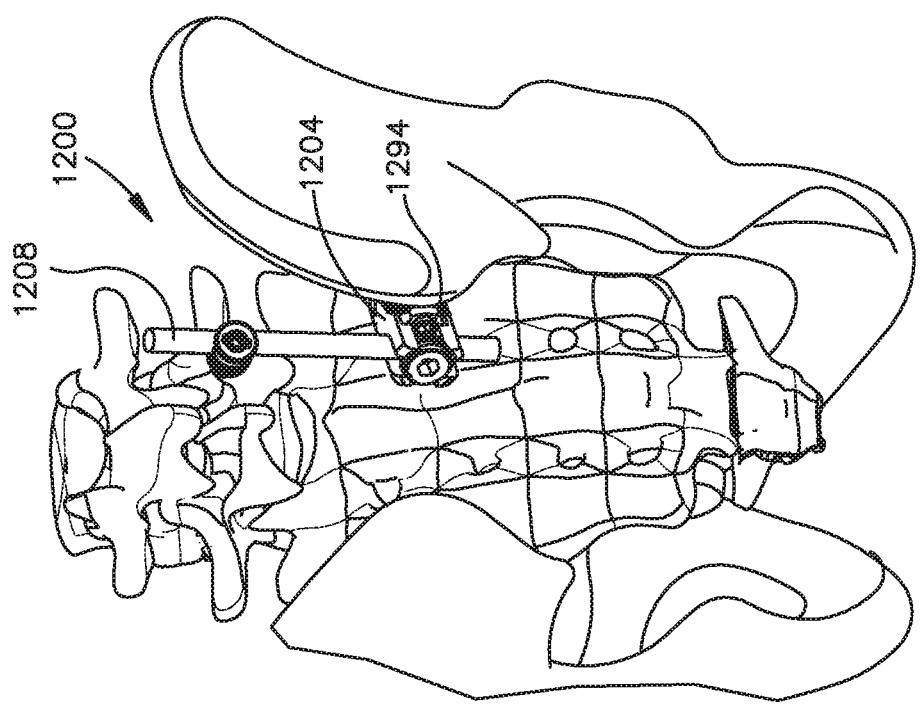
FIG. 80 is a perspective view of the interbody implant of FIG. 79A positioned in a sacro-iliac joint and coupled to a spinal rod that is also coupled to a pedicle screw.

As shown in FIG. 80, the system 1200 can include an implant 1204 and the rod 1208 can be configured as a spinal rod that is coupled to at least one such as a plurality of vertebra via respective pedicle screws. Therefore, the system 1200 can further include at least one such as a plurality of pedicle screws. In such a system the surgical method can further include the steps of inserting the spinal rod 1208 into the rod receiving channel 1288 and then inserting the locking cap 1294 into the locking cap channel 1290 to thereby secure the spinal rod 1208 within the rod receiving channel 1288.

Figure 81:
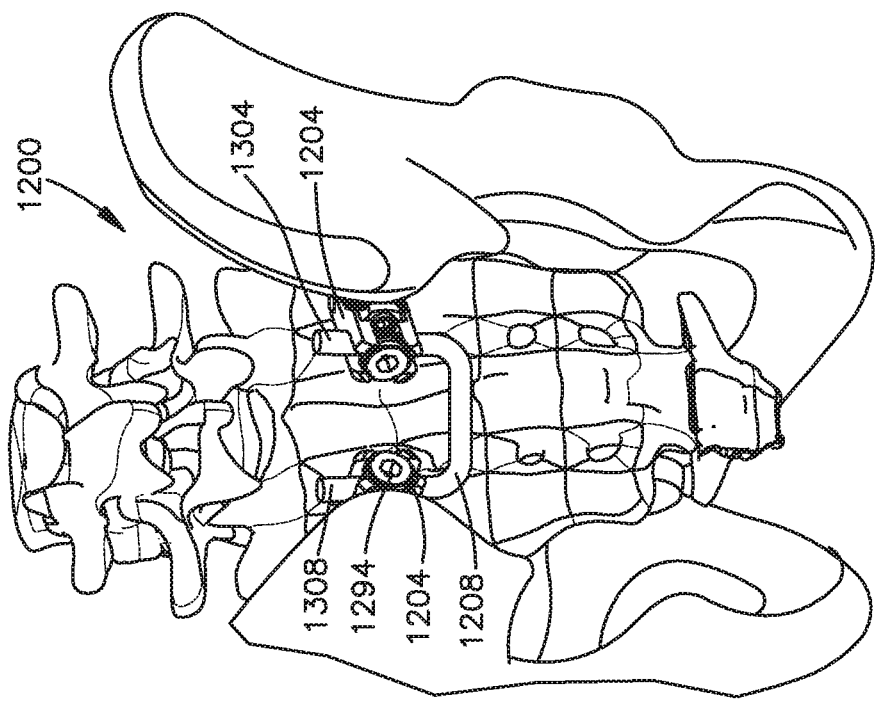
FIG. 81 is a perspective view of first and second interbody implants shown in FIG. 79A positioned in first and second sacro-iliac joints and coupled together with a rod configured as a bridge.

As shown in FIG. 81, the system 1200 can include first and second implants 1204 each inserted into a respective sacro-iliac joint 912, and the rod 1208 can be configured as a bridging rod having a first side 1304, a second side 1308, and a crossbar 1312 that connects the first side 1304 to the second side 1308. As shown in FIG. 81, the first side 1304 is configured to be received by the rod receiving channel 1288 of the first implant 1204 and the second side 1308 is configured to be received by the rod receiving channel 1288 of the second implant 1204. Such a system can be configured to apply compression between two implants 1204 and can include the steps of compressing a sacral fracture, inserting the rod 1208 into the rod receiving channels 1288 of the implants 1204 and inserting locking caps into the locking cap channels 1290 of the implants 1204 to thereby secure the rod 1208 within the rod receiving channel 1288.

It should be appreciated, that any of the instruments and implants disclosed can be provided as a kit along with any of the rods disclosed, and/or one or more pedicle screws and bone fixation elements. Moreover, it should be appreciated that structure from each implant can be incorporated into any of the implants. For example, the implant 1204 can be configured to have four bone fixation element receiving apertures as shown in FIG. 77 and can be further configured to have the first and second locking channels of the implant 904.

It will be apparent to those skilled in the art that various modifications and variations can be made in the structure and the methodology of the present invention, without departing from the spirit or the scope of the invention. Thus, it is intended that the present invention cover the modifications and the variations of this invention provided that they come within the scope of the appended claims and their equivalents.

What is claimed:

1. An implant configured to be inserted into a sacro-iliac joint along an insertion direction, the sacro-iliac joint being defined between a sacral bone and an iliac bone, the implant comprising:
    an implant body having a proximal end and a distal end spaced from the proximal end along the insertion direction, the implant body defining an iliac engagement surface sized and configured to abut the iliac bone when the implant is inserted into the sacro-iliac joint, and a sacral engagement surface that is opposite the iliac engagement surface along a first direction, perpendicular to the insertion direction, the sacral engagement surface sized and configured to abut the sacral bone when the implant is inserted into the sacro-iliac joint, wherein at least one of the iliac engagement surface and the sacral engagement surface converges toward the other of the iliac engagement surface and the sacral engagement surface as it extends along a direction from the proximal end to the distal end; and
    a head portion that extends from the proximal end of the implant body, the head portion including:
        a head body that has a width measured along the first direction that is perpendicular to the insertion direction, the width being greater than a width of the proximal end the implant body along the first direction such that the head body defines a first projection that extends beyond the iliac engagement surface and a second projection that extends beyond the sacral engagement surface;
        a first bone fixation element receiving aperture that extends through the head body along a first central axis such that when the implant body is received within the sacro-iliac joint, the first bone fixation element receiving aperture is configured to receive a bone fixation element along the first central axis so as to align the bone fixation element with one of the sacral bone or the iliac bone;
        a second bone fixation element receiving aperture that is aligned with the first bone fixation element receiving aperture along the first direction and that extends through the head body along a second central axis such that, when the implant body is received within the sacro-iliac joint, the second bone fixation element receiving aperture is configured to receive a bone fixation element along the second central axis so as to align the bone fixation element with another one of the sacral bone and the iliac bone;
        a first locking channel that extends into the head body along a first locking central axis; and
        a second locking channel that extends into the head body along a second locking central axis that is angularly offset with respect to the first locking central axis, wherein the first and second locking channels are aligned along a second direction that is perpendicular to both the first direction and the insertion direction, the first and second locking central axes extend between the iliac engagement surface and the sacral engagement surface, and one of the first and second locking central axes extends towards the other one of the first and second locking central axes.

2. The implant of claim 1, wherein the head portion further includes third and fourth bone fixation element receiving apertures that extend through the head body along third and fourth central axes such that when the implant body is received within the sacro-iliac joint, the third and fourth bone fixation element receiving apertures are configured to receive third and fourth bone fixation elements along the third and fourth axes, respectively, so as to align each of the third and fourth bone fixation elements with one of the sacral bone and the iliac bone.

3. The implant of claim 2, wherein the third bone fixation element receiving aperture is aligned with the first bone fixation element receiving aperture along the second direction and the fourth bone fixation element receiving aperture is aligned with the second bone fixation element receiving aperture along the second direction.

4. The implant of claim 1, wherein the head portion further includes a guide wire channel that extends through the head body along the insertion direction.

5. The implant of claim 4, wherein the guide wire channel extends through the head body between the first and second bone fixation element receiving apertures and between the first and second locking channels.

6. The implant of claim 4, wherein the guide wire channel extends through the head body between the first and second bone fixation receiving apertures.

7. The implant of claim 4, wherein the implant body includes a guide wire receiving channel that extends therethrough along the insertion direction such that the guide wire channel of the head portion is coaxial with the guide wire channel of the implant body.

8. The implant of claim 7, wherein the implant body includes a first body portion and a second body portion separated from the first body portion along a direction that is perpendicular to the insertion direction such that a gap is defined between the first and second body portions.

9. The implant of claim 1, wherein the implant body defines a first width at the proximal end that is between about 7 mm and about 14 mm and a second width at the distal end that is between about 1.5 mm and about 4.5 mm.

10. A system comprising:
    the sacral-iliac joint implant of claim 1; and
    an insertion instrument configured to insert the sacral-iliac joint implant into the sacral-iliac joint, the insertion instrument comprising:
        a guide body that defines a proximal end and a distal end that is spaced from the proximal end along the insertion direction, the guide body defining a channel that extends through at least a portion of the guide body along a central channel axis and extends out the distal end;
a first locking member movable within the channel of the guide body between an unlocked position and a locked position, wherein the first locking member extends further from the distal end when in the locked position than when in the unlocked position
a second locking member that extends from the distal end of the guide body along a second member central axis that is angularly offset with respect to the central channel axis, the second locking member being configured to be received by the second locking channel of the sacral-iliac joint implant; and
wherein when the second locking member is inserted into the second locking channel of the sacral-iliac joint implant, the channel of the guide body is configured to be positioned coaxial with respect to the first locking channel of the sacral-iliac joint implant such that movement of the first locking member from the unlocked position to the locked position causes the first locking member to be inserted into the first locking channel to thereby couple the sacral-iliac joint implant to the insertion instrument.

11. The system of claim 10, wherein the guide body further includes a guide wire channel that extends from the proximal end through to the distal end, the guide wire channel being configured to receive a guide wire to thereby guide the instrument toward the joint.

12. The system of claim 11, wherein the guide body further includes a first bone fixation element receiving channel that extends from the proximal end through to the distal end, the first bone fixation element receiving channel being configured to be coaxial with the first bone fixation receiving aperture of the implant, and a second bone fixation element receiving channel that extends from the proximal end through to the distal end, the second bone fixation element receiving channel being configured to be coaxial with the second bone fixation element receiving aperture of the implant.

13. The implant of claim 1, wherein the at least one of the iliac engagement surface and the sacral engagement surface converges toward the other of the iliac engagement surface and the sacral engagement surface as it extends from the head to the distal end.

14. The implant of claim 13, wherein the entire iliac engagement surface and the entire sacral engagement surface converge towards one another.

15. The implant of claim 1, wherein the implant body has a width along the first direction from the iliac engagement surface to the sacral engagement surface that is greater than a width of each of the first and second locking channels along the first direction.

16. The implant of claim 1, wherein the first central axis of the first bone fixation element receiving aperture is aligned with the second central axis of the second bone fixation element receiving aperture along the first direction.

17. The implant of claim 1, wherein:
the first locking channel extends from a first opening in a surface of the head body; and
the second locking channel extends from a second opening in a surface of the head body.

18. A sacral-iliac joint implant, comprising:
an implant body having a proximal end and a distal end spaced from the proximal end along an insertion direction, the implant body defining an iliac engagement surface sized and configured to abut an iliac bone when the implant is inserted into a sacro-iliac joint, and a sacral engagement surface sized and configured to abut a sacral bone when the implant is inserted into the sacro-iliac joint, wherein at least one of the iliac engagement surface and the sacral engagement surface converges toward the other of the iliac engagement surface and the sacral engagement surface as it extends along a direction from the proximal end to the distal end; and
a head portion that extends from the proximal end of the implant body, the head portion including a head body having a width measured along a first direction that is perpendicular to the insertion direction, the width being greater than a width of the proximal end the implant body along the first direction such that the head body defines a first projection that extends beyond the iliac engagement surface and a second projection that extends beyond the sacral engagement surface, the head portion defining:
a first bone fixation element receiving aperture that extends through the head body along a first central axis such that, when the implant body is received within the sacro-iliac joint, the first bone fixation element receiving aperture is configured to receive a first bone fixation element along the first central axis so as to align the first bone fixation element with the sacral bone;
a second bone fixation element receiving aperture that extends through the head body along a second central axis such that when the implant body is received within the sacro-iliac joint, the second bone fixation element receiving aperture is configured to receive a second bone fixation element along the second central axis so as to align the second bone fixation element with the iliac bone;
a first locking channel that extends into the head body along a first locking central axis that is parallel with the insertion direction; and
a second locking channel that extends into the head body along a second locking central axis that is at an oblique angle with the insertion direction.

19. The implant of claim 18, wherein the first and second bone fixation element receiving apertures extend through the first and second projections of the head portion, respectively.

20. The implant of claim 18, both the first and second projections define abutment surfaces that are configured to abut outer surfaces of the iliac and sacral bones to thereby act as a stop so as to prevent the head portion from being inserted into the sacro-iliac joint.

21. The implant of claim 18, wherein the head portion defines a cross-shape.

22. The implant of claim 18, wherein:
the first locking channel extends from a first opening in a surface of the head body; and
the second locking channel extends from a second opening in a surface of the head body.

* * * * *